United States Patent
Vanderhoff et al.

(10) Patent No.: US 6,544,503 B1
(45) Date of Patent: Apr. 8, 2003

(54) PROCESS FOR THE PREPARATION OF AQUEOUS DISPERSIONS OF PARTICLES OF WATER-SOLUBLE POLYMERS AND THE PARTICLES OBTAINED

(75) Inventors: John W. Vanderhoff, Bethlehem, PA (US); Cheng Xun Lu, Somerset, NJ (US); Clarence C. Lee, Lilburn, GA (US); Chi-Chun Tsai, Lawrenceville, GA (US)

(73) Assignees: C. R. Bard, Inc., Murray Hill, NJ (US); Lehigh University, Bethlehem, PA (US)

( * ) Notice: Subject to any disclaimer, the term of this patent is extended or adjusted under 35 U.S.C. 154(b) by 0 days.

(21) Appl. No.: 09/563,037

(22) Filed: May 1, 2000

Related U.S. Application Data

(63) Continuation of application No. 08/989,888, filed on Dec. 12, 1997, now Pat. No. 6,214,331, which is a continuation-in-part of application No. 08/659,770, filed on Jun. 6, 1996, now abandoned, which is a continuation-in-part of application No. 08/466,676, filed on Jun. 6, 1995, now abandoned.

(51) Int. Cl.$^7$ .......................... A61K 31/74; A61K 47/48
(52) U.S. Cl. .................. 424/78.17; 424/489; 424/423; 424/422
(58) Field of Search .................. 514/772.1, 772.2, 514/772.3, 772.4, 54, 23, 58, 59, 60; 523/113; 604/502; 424/78.17, 489, 423, 422

(56) References Cited

U.S. PATENT DOCUMENTS

| | | | |
|---|---|---|---|
| 4,107,288 A | 8/1978 | Oppenheim et al. | 424/22 |
| 4,124,705 A | 11/1978 | Rothman et al. | 424/180 |
| 4,147,767 A | 4/1979 | Yapel, Jr. | 424/22 |
| 4,713,446 A | 12/1987 | DeVore et al. | 530/356 |
| 4,963,367 A | 10/1990 | Ecanow | 424/485 |
| 5,007,940 A * | 4/1991 | Berg | 523/113 |
| 5,041,292 A | 8/1991 | Feijen | 424/484 |
| 5,099,013 A | 3/1992 | Balazs et al. | 536/55.1 |
| 5,116,387 A * | 5/1992 | Berg | 523/113 |
| 5,126,140 A * | 6/1992 | Ito et al. | 523/113 |
| 5,128,326 A * | 7/1992 | Balazs et al. | 514/54 |
| 5,201,764 A | 4/1993 | Kelman et al. | 623/6 |
| 5,264,214 A | 11/1993 | Rhee et al. | 424/422 |
| 5,304,595 A | 4/1994 | Rhee et al. | 525/54.1 |
| 5,328,955 A | 7/1994 | Rhee et al. | 525/54.1 |
| 5,334,640 A | 8/1994 | Desai et al. | 524/56 |
| 5,376,375 A | 12/1994 | Rhee et al. | 424/423 |
| 5,380,536 A | 1/1995 | Hubbell et al. | 424/497 |
| 5,395,620 A | 3/1995 | Huc et al. | 424/499 |
| 5,639,796 A * | 6/1997 | Lee | 523/113 |
| 5,792,478 A * | 8/1998 | Lawin et al. | 523/113 |
| 6,096,018 A * | 8/2000 | Luzio et al. | 604/500 |
| 6,184,266 B1 * | 2/2001 | Ronan et al. | 523/113 |
| 6,207,180 B1 * | 3/2001 | Ottoboni et al. | 514/772.3 |
| 6,214,331 B1 * | 4/2001 | Vanderhoff et al. | 514/772.1 |

FOREIGN PATENT DOCUMENTS

| | | |
|---|---|---|
| EP | 0 256 293 A2 | 2/1988 |
| EP | 0 256 293 A3 | 2/1988 |
| EP | 0 507 604 A2 | 10/1992 |
| EP | 0 281 809 B1 | 8/1993 |
| EP | 0 555 980 A1 | 8/1993 |
| EP | 0 402 031 B1 | 12/1993 |
| GB | 2 151 244 A | 7/1985 |
| WO | WO 91/01721 | 2/1991 |
| WO | WO 93/13136 | 7/1993 |

* cited by examiner

Primary Examiner—Thurman K. Page
Assistant Examiner—Liliana Di Nola-Baron
(74) Attorney, Agent, or Firm—Kilpatrick Stockton LLP

(57) ABSTRACT

The invention is a process for the preparation of crosslinked water-swellable polymer particles. First, an aqueous polymer solution containing a water-soluble polymer having at least one functional group or charge, is combined with aqueous medium. The aqueous polymer solution is then mixed under moderate agitation with an oil medium and an emulsifier to form an emulsion of droplets of the water-soluble polymer. A crosslinking agent capable of crosslinking the functional groups and/or charges in the water-soluble polymer is then added to the emulsion to form crosslinked water-swellable polymer particles. The invention also includes the particles formed by the process and aqueous dispersions containing the particles which are useful for administering to an individual. The particles of the invention are useful for implantation, soft tissue augmentation, and scaffolding to promote cell growth.

15 Claims, No Drawings

PROCESS FOR THE PREPARATION OF AQUEOUS DISPERSIONS OF PARTICLES OF WATER-SOLUBLE POLYMERS AND THE PARTICLES OBTAINED

RELATED APPLICATIONS

This application is a continuation of Ser. No. 08/989,888, U.S. Pat. No. 6,214,331 B1, filed Dec. 12, 1997 which is a continuation-in-part of U.S. patent application Ser. No. 08/659,770, filed Jun. 6, 1996 now abandoned, which is a continuation-in-part of U.S. patent application Ser. No. 08/466,676, filed Jun. 6, 1995, now abandoned.

BACKGROUND OF THE INVENTION (A) Field of the Invention

This invention relates to the preparation of aqueous dispersions of water-swellable polymer particles and to the particles obtained from such a process.

(B) Description of the Prior Art

Aqueous dispersions of water-soluble polymer particles are difficult to manufacture. It is particularly difficult to control particle size and shape and to make such particles reproducibly. Aqueous dispersions of water-soluble polymer particles that have been available prior to this invention are, in general, not satisfactory. Previously, such particles are generally prepared by adding a crosslinking agent to an aqueous polymer solution under agitation. Agitation serves to break down the crosslinking polymer to give the desired particle size. To break down the crosslinked and crosslinking polymers, sufficient mechanical stress to cause shearing and disruption of particle integrity is required. This level of mechanical stress can only be achieved by applying vigorous agitation. This concurrent agitation-crosslinking method gives an undesirably broad distribution of particle sizes and shapes, and produces undesirable particle fragments. Additionally, there is substantial variability in the resulting particle populations between production runs.

A particularly undesirable aspect of the heterogeneous particle population produced by this method is that it is difficult or impossible to "clean up" or fractionate the heterogeneous population to yield a homogeneous population of particles having the same size and shape. A homogeneous population of particles is particularly desirable where the particles are to be delivered by injection through a narrow guage syringe needle.

Other processes for preparing aqueous dispersions of crosslinked water-soluble polymer particles involve methods that are of a proprietary nature. However, such particles are either not available in the quantities to meet commercial demand, their physical parameters are not suitable for a particular application, or their properties cannot be varied systematically. Moreover, a full range of polymer compositions and sizes has not been available.

Water-soluble particles have various utilities. There are three basic types of water-based polymers:

(a) solution polymers. These polymers comprise dispersions of individual polymer molecules. The viscosity of the solution depends upon the molecular weight and concentration of the polymer; the higher the molecular weight and concentration, the higher is the viscosity of the solution. The viscosity of the solution limits the use of these solution polymers to low molecular weights and low concentrations. This is especially true where the use involves delivery of particles via injection through a narrow gauge syringe needle.

(b) latexes. These polymers comprise colloidal dispersions of polymer particles, each of which comprises hundreds or thousands of polymer molecules. The viscosity of the latex depends upon the interactions between the colloidal particles and is independent of the molecular weight of the polymer. Thus, latexes often combine low viscosities with high polymer concentrations. Moreover, the mechanism and kinetics of emulsion polymerization favor the preparation of high-molecular-weight polymers with rapid rates of polymerization. Aqueous dispersions of crosslinked water-soluble polymers can be prepared by inverse emulsion or inverse suspension polymerization of monomer mixtures containing a crosslinking monomer, e.g., a mixture of acrylamide and methylene-bis-acrylamide. However, this method is limited to polymers that can be prepared by radical chain polymerization, which excludes natural water-soluble polymers. There remains a need to prepare particles of water-soluble polymers that are derived from natural sources.

(c) Water-reducible or water-dispersible polymers. These polymers have a degree of dispersion intermediate between that of solution polymers and that of latexes. The viscosity of these intermediate samples depends upon the relative degrees of solution polymer and latex polymer character. As with the latexes, this method is limited to polymers that can be prepared by radical chain polymerization.

Polysaccharides are naturally occurring biopolymers that exist in a highly viscous liquid state in animal tissues, where they readily react with proteins to from glycosaminoglycans or proteoglycans.

Biocompatible and non-biodegradable particles that are non-cytotoxic, non-carcinogenic, non-inflammatory, non-pyrogenic, and non-immunogenic are needed to provide a solution to the long felt and unfulfilled need for an improved composition useful for implants; soft tissue augmentation to treat congenital abnormalities, acquired defects, and cosmetic defects; and tissue scaffolding to promote cell growth.

Homogeneous populations of such particles would be particularly useful for soft tissue augumentation by surgical implantation or, preferably, delivery to the desired site by conventional injection through a narrow gauge syringe needle.

It would be particularly desirable to use such particles to treat urinary incontinence and vesicoureteral reflux, for correction of wrinkles and other skin defects, or to serve as a general augmention or replacement composition or as a scaffold material in soft or hard tissues such as breast, lip, penis, bone, cartilage, and tendon.

U.S. Pat. No. 4,124,705 to Rothman, et al. (hereinafter "Rothman") discloses hydrophilic, water-insoluble particles having a particle size between 0.1 and 300 micrometers which are composed of a polysaccharide or polysaccharide derivative such as starch, glycogen, or dextrins. The particles are crosslinked into a three-dimensional network by $\alpha(1\rightarrow4)$glucosidic linkages. This network is degraded in the body through hydrolyzation of the $\alpha(1\rightarrow4)$glucosidic linkages by $\alpha$-amylase to form water-soluble fragments.

The Rothman particles are produced by bead polymerization in which a solution of the polysaccharide is dispersed to droplet form in an inert liquid, such as octanol, which may contain an emulsion stabilizer, such as Gafac® PE 510. A crosslinking agent, for example, a di- or multi-epoxides or a dicarboxylic acid, is then added to the reaction mixture. The octanol used in the Rothman process is a polar solvent which is miscible with the aqueous solution of the polysaccharide.

The Rothman particles are administered intravascularly in aqueous solutions, such as glucose, sorbitol, or saccharose, to block the finer blood vessels leading to a particular part of the body. This prevents the tissue in that part of the body, for example, a tumor, from receiving necessary oxygen and nutrients and inhibits growth of the tissue. The particles may also be administered with a diagnostic or therapeutic agent, allowing the agent to be trapped within or without of the effected tissue for brief periods of time.

European patent application 256,293 to Mitsubishi discloses water-insoluble, crosslinked, polyvinyl alcohol particles in the shape of spheres having an average particle size from 20 to 1,000 micrometers. The particles are produced by dispersing a solution of polyvinyl alcohol and a salt in an organic solvent, such as a hydrocarbon, to form a gel which is then reacted with a crosslinking agent, such as a dialdehyde, diepoxide, glycidyl ether, and epihalohydrin. Suitable salts are sodium chloride, sodium sulfate or any other salt capable of coagulating and precipitating polyvinyl alcohol. A dispersion stabilizer, such as a cellulose or sorbitan derivative, may be added to the reaction mixture. Mitsubishi further discloses that the crosslinked polyvinyl alcohol particles are suitable for packing materials in chromatography.

European patent application 555,980 to Nisshinbo discloses crosslinked, spherical particles of water-soluble polymers, having a particle size from 0.1 to 30 micrometers. Specific polymers disclosed are sodium alginate, dextran, dextran sulfate sodium, carragheenan, agarose, agar, gelatin, pectin, water-soluble cellulose derivatives, such as carboxymethylcellulose sodium. The polymer particles also contain an oligosaccharide or polyhydric alcohol, such as sucrose, which is necessary to provide the particles with a spherical shape. Specific oligosaccharides disclosed are mannose, sucrose, cellobiose and raffinose; specific polyhydric alcohols are polyethylene glycol or erythritol. The Nisshinbo particles are useful as additives and binders because of their water-retaining and lubricating properties.

The polymeric particles of Nisshinbo are made by preparing an aqueous solution of the water-soluble polymer and an oligosaccharide or polyhydric alcohol. This solution is then spray-dried to form spherical particles. Nisshinbo discloses that it is not possible to obtain spherical particles through spray drying techniques without the addition of an oligosaccharide or polyhydric alcohol. The spray dried particles are then crosslinked. Specific covalent crosslinking agents disclosed are divinyl compounds or bisepoxide, while specifically disclosed ionic crosslinking agents are calcium chloride and other divalent metal salts.

U.S. Pat. No. 4,716,154 to Malson, et al. (hereinafter "Malson") discloses a transparent, homogeneous, crosslinked hyaluronic acid gel which is a clear optical mass useful for replacement of vitreous humor in individuals with retinal detachment. The gel may contain other polysaccharides in additional to hyaluronic acid. The gel is administered by injection through a 0.9 millimeter needle tip.

The process by which the gel of Malson is made involves dissolving hyaluronic acid and a crosslinking agent in an alkaline medium, preferably at an elevated temperature of about 50° C. The resulting gel must be washed to remove unreacted crosslinking agent. The prefered crosslinkers disclosed are di- or polyfunctional epoxides.

U.S. Pat. No. 5,603,956 to Mateescu, et al. (hereinafter "Mateescu") discloses crosslinked polymer particles of amylose having a size of about 0.5 to about 5.0 micrometers which form agglomerates of approximately 25–700 micrometers. The polymers are crosslinked solely through $\alpha(1\rightarrow 4)$ linkages.

The Mateescu particles are formed by direct compression of an admixture of a drug with the crosslinked amylose polymer and an amount of $\alpha$-amylase enzyme. The crosslinked amylose polymer is formed by swelling amylose in an alkaline medium in a planetary mixer, with homogenization, followed by addition of the crosslinker with moderate heating of between 40–70° C.

The polymers are useful for the slow release of drugs. The $\alpha$-amylase present in the particles breaks down the $\alpha(1\rightarrow 4)$ linkages, releasing the drug and degrading the polymer.

U.S. Pat. No. 5,371,208 to Kozulic discloses electrophoresis gels having a very low polymer concentration and improved optical properties. The gels are formed by reacting a hydroxyl group containing polymer with a crosslinker that is capable of forming ether linkages, such as bis-epoxides, in an aqueous medium at a basic pH. Because the process is performed in water, hydrolysis of the reactive groups present in the crosslinker is an unavoidable side reaction.

U.S. Pat. No. 5,041,292 to Feijen discloses drug delivery system containing a drug and a biodegradable hydrogel matrix, formed by linking a polysaccharide and a protein with a crosslinking agent. The Feijen process involves dissolving the polysaccharide, protein, and crosslinking agent in an aqueous medum. The crosslinked particles are then loaded with the desired drug. The hydrogel may be shaped into many forms, including microspheres which may be from less than 100 nanometers to over 7 micrometers in diameter. Feijen discloses that the size may be varied in order to place the gels in the capillary bed of the lungs, the liver and spleen through phagocytosis of small particles, and in the extracellular tissue.

The particles formed by Feijen are maintained by mechanical agitation prior to crosslinking, and once formed are stabilized by heat, which is only possible in the presence of the additional protein component. Thus, the size and shape of the particles are controlled solely by the mechanical force of the system.

Thus, there is a need for aqueous dispersions of water-swellable polymer particles of a relatively narrow particle size distribution with defined physical characteristics, for a process for preparing such dispersions, and for recovery of particles in any desired quantity at reasonable cost.

SUMMARY OF THE INVENTION

Stated generally, the invention comprises in one embodiment a process for producing a crosslinked water-swellable polymer particle preparation and the particles produced by the process. In the first step of the process of the invention, an aqueous polymer solution containing at least one water-soluble polymer, having at least one functional group or charge, is combined with an aqueous medium. The aqueous polymer solution is then mixed under moderate agitation with an oil phase containing an inert hydrophobic liquid and at least one emulsifier to form an emulsion of droplets of the water-soluble polymer. At least one crosslinking agent capable of crosslinking the functional groups and/or charges in the water-soluble polymer is then added to the emulsion to form crosslinked water-swellable polymer particles. This emulsion of crosslinked water-swellable polymer particles may optionally be inverted in an excess of water to provide an aqueous dispersion of crosslinked water-swellable polymer particles. Optionally, the crosslinked water-swellable polymer particles can be recovered from the aqueous dispersion by conventional methods.

In one embodiment, the dislosedprocess comprises forming an aqueous solution of a water-soluble polymer having at least one of the following functional groups: hydroxyl groups, thiol groups, carboxyl groups, sulfonic acid groups, sulfate groups, phosphate groups, amino groups, aldehyde groups, and sulfonyl halide groups. This aqueous solution is then added to an oil phase containing a hydrocarbon and an emulsifier having a low HLB value, preferably less than 8.

In another embodiment, the invention generally comprises a crosslinked water-swellable polymer particle preparation. The preparation contains crosslinked water-swellable polymer particles that are substantially homogeneous in size. The particles have a size between about 10 and about 250 micrometers in diameter. The particles are preferably less than 212 micrometers in diameter. At least about 80% of the particles in the preparation are spherical. More specifically, the particle preparation comprises particles composed of one or more water-soluble polymers having at least one of the following functional groups: hydroxyl groups, thiol groups, carboxyl groups, sulfonic acid groups, sulfate groups, phosphate groups, amino groups, aldehyde groups, and sulfonyl halide groups, and at least 95% of the particles are spherical.

In yet another embodiment, the invention generally comprises aqueous dispersions containing crosslinked water-swellable polymer particles that are substantially homogeneous in size. The particles in the dispersion have a particle size between about 10 and about 250 micrometers in diameter, preferably less than 212 micrometers. More specifically, the aqueous dispersions are suitable for medicinal purposes.

Stated generally, another embodiment of the invention comprises the use of crosslinked water-swellable polymer particles and aqueous dispersions containing them for medicinal purposes. More specifically, these methods include administering an aqueous dispersion containing the crosslinked water-swellable polymer particles to an individual as implants, as scaffold material for cell growth, or for soft tissue augmentation. Even more specifically, the invention comprises a method of soft tissue augmentation useful for the treatment of urinary incontinence, vesicoureteral reflux, glottic insufficiency, gastroesophageal reflux, or skin defects. The method also specifically comprises a method of providing scaffolding material for wound healing and for tissue replacement in tissues in the breast, lip, penis, bone, cartilage, and tendon.

Therefore, it is an object of the present invention to provide a simple and cost effective method of preparing crosslinked water-swellable polymer particles.

It is another object of the invention to provide a process for preparing crosslinked water-swellable polymer particles which provides an improved method for controlling the size and shape of the particles formed.

It is yet another object of the invention to provide a process for the production of crosslinked water-swellable polymer particles that provides a high degree of crosslinking.

It is a further object of the invention to provide a process for the production of aqueous solutions of crosslinked water-swellable particles.

It is an object of the invention to provide crosslinked water-swellable polymer particles that are substantially homogeneous in size.

It is another object of the invention to provide crosslinked water-swellable polymer particles having a size between about 10 and about 250 micrometers.

It is yet another object of the invention to provide crosslinked water-swellable polymer particles having a substantially uniform, spherical shape.

It is a further object of the invention to provide crosslinked water-swellable polymer particles containing one or more water-soluble particles having at least one or more functional groups or charges.

It is an object of the invention to provide crosslinked water-swellable polymer particles which are rigid and elastic.

It is another object of the invention to provide aqueous dispersions of crosslinked water-swellable polymer particles which can be injected through a narrow gauge hypodermic syringe needle.

It is yet another object of the invention to provide a method of soft tissue augmentation by administering an aqueous dispersion of crosslinked water-swellable polymer particles.

It is a further object of the invention to provide scaffolding material to promote cell growth by administering an aqueous dispersion of crosslinked water-swellable polymer particles.

DETAILED DESCRIPTION OF THE INVENTION

The present invention relates to a process for preparing crosslinked water-swellable, hydrophilic polymer particles from water-soluble polymers, the polymer particles formed by the process, and aqueous dispersions and pharmaceutically acceptable dispersions of the polymer particles. The invention also relates to therapeutic methods of using of the polymer particles.

The present invention provides biocompatible and non-biodegradable particles that are substantially non-cytotoxic, non-carcinogenic, non-inflammatory, non-pyrogenic, and non-immunogenic, and which lack other unwanted humoral or cellular responses. The particles also possess sufficient long-term stability of size, shape, rigidity, and compositon to have utility as implant materials. A further characteristic of the particles of the invention which makes them useful for implant purposes is that they are relatively inert and do not rapidly degrade in vivo. A particularly advantageous feature of the particles of the invention is that they are easily injectable. Preferably, the crosslinked water-swellable polymer particles prepared according to the invention are substantially homogeneous in size. They are generally from about 10 microns in diameter to about 250 microns in diameter, and at least 80% of the particles are spherical. Preferably, the particles are greater than about 10 micometers in diameter and less than about 212 micrometers in diameter, and at least 90% of the particles are spherical. In this application, the term substantially homogeneous means that at least 80% of the particles are within one standard deviation of the mean or average size of the particles. Such particles provide a solution to the long felt and unfulfilled need for an improved composition useful for medical treatments, such as implantation; soft tissue augmentation to treat congenital abnormalities, acquired defects, or cosmetic defects; and tissue scaffolding to promote cell growth and wound healing.

Examples of congenital defects treatable with the particles of the invention include, without limitation, hemifacial microsomia, malar and zygomatic hypoplasia, unilateral mammary hypoplasia, pectus excavatum, pectoralis agenesis and velopharyngeal incompetence secondary to cleft palate repair or submucous cleft palate. Examples of acquired defects include, without limitation, post surgical, post traumatic and post infectious defects, such as depressed scars, subcutaneous atrophy, acne pitting, linear scleroderma with subcutaneous atrophy, saddle-nose deformity, Romberg's disease, and unilateral vocal cord paralysis. Cosmetic defects include, without limitation, glabellar frown lines, nasolabial creases, circumoral geographical wrinkles, sunken cheeks and mammary hypoplasia.

The homogeneous populations of particles produced by the process of the invention are useful for soft tissue augumentation involving delivery to the desired implantation site by conventional injection through a narrow gauge syringe needle (such as a 20, 21 or 22 guage needle), although they are also useful for surgical implantation and other delivery methods, such as endoscopy.

The particles of the invention are useful for the treatment of urinary incontinence, vesicoureteral reflux, glottic insufficiency, and gastroesophageal reflux, and for correction of wrinkles and other skin defects, or to serve as a general augumention or replacement composition or as a scaffold material in soft or hard tissues such as breast, lip, penis, bone, cartilage, and tendon. When the particles of the invention are administered to a patient to serve as scaffold material, the particles facilitate the migration and infiltration of fibroblasts and related cells. The large free spaces within the microsphere of the present invention, particularly polysaccharide microspheres, allows cells to infiltrate into and through the bead. Additionally, the large surface area of the microspheres promotes attachment and growth of infiltrating cells. Still further, the scaffolding material is gradually degraded and absorbed by the host. Optionally, when the microspheres of the present invention are used as scaffolding material, bioactive agents can be crosslinked, coupled or otherwise attached, using methods well known in the art, to provide localized cellular stimuli. Examples of such bioactive agents include growth factors and cytokines, such as fibroblastic growth factor, endothelial growth factor, interlukins, platelet derived growth factor, tissue necrosis factor, hormones, cell adhesion peptides, etc. Accordingly, when the microspheres of the present invention are used as scaffolding material, colonization of the site by cells is facilitated.

A particularly advantageous feature of the invention is that process parameters such as the composition of the oil phase employed, the emulsifying agents selected, temperature, pH, crosslinking time and washing, can be adjusted and precisely controlled in small scale synthesis, and then readily and reproducibly duplicated when scaled-up to full production runs to achieve superior microparticles having beneficial characteristics, such as substantially uniform size and shape, excellent physical and chemical stability, and elastic properties that permit easy extrusion through small gauge syringe needles.

The process of preparing crosslinked water-soluble polymer particles comprises dissolving at least one water-soluble polymer having at least one functional group or charge in water or aqueous buffer to provide the desired concentration of the polymer in solution. The aqueous polymer-containing solution is then added to an oil phase which includes at least one water-in-oil emulsifying agent in an amount suitable to provide the desired concentration of the water-soluble polymer. The mixture is agitated moderately to form an emulsion containing droplets of the water soluble polymer. The polymer droplets are crosslinked in-situ by at least one crosslinking agent, resulting in the formation of crosslinked water-swellable polymer particles. Following crosslinking, the polymer-in-oil emulsion is then optionally inverted in an excess of water to provide an aqueous dispersion of the crosslinked polymer particles. The particles may then be recovered from the aqueous dispersion. Preferably, the particles of the invention are formed from a single water-soluble polymer, although particles containing multiple water-soluble polymers are within the scope of the present invention.

Any water-soluble polymer, natural or synthetic, can be used in the practice of the invention provided that (1) the viscosity of an aqueous solution of the polymer is low enough that it can be broken down into droplets during the emulsification step, and (2) it contains at least one functional group or charge that can serve as sites for reaction with a crosslinking agent. Generally, solutions with viscosities as high as $10^4$–$10^5$ cps can be broken down into droplets by the usual methods of emulsification.

Water-soluble polymers useful in the invention will contain one or more types of functional groups or charges which can react with a crosslinking agent to form covalent and/or ionic bonds. Examples of functional groups, without limitation, are hydroxyl groups, thiol groups, carboxyl groups, sulfonic acid groups ($SO_3H$), sulfate groups ($OSO_3H$), phosphate groups ($OPO_3H$), amino groups, aldehyde groups, and sulfonyl halide groups ($SO_2X$, where X is Cl or Br).

Examples of water-soluble polymers useful in the process of the invention include, but are not limited to, proteins, polysaccharides, peptidoglycans (heteroglycan chains comprising alternating units of N-acetylglusocsamine (GlcNAc) and N-acetylmuramic acid (MurNAc) linked to various peptides), glycoproteins (proteins to which carbohydrate chains are attached), proteoglycans (proteins to which glycosaminoglycan chains are linked), teichoic acids, lipopolysaccharides, synthetic hydrophilic polymers, and mixtures thereof.

Other hydrophilic polymers useful in the invention include, but are not limited to, natural polysaccharides, such as hyaluronic acid, sodium alginate, chondroitin sulfate, celluloses, chitin, chitosan, agarose, xanthans, dermatan sulfate, keratin sulfate, emulsan, gellan, curdlan, amylose, carrageenans, amylopectin, dextrans, glycogen, starch, heparin sulfate, and limit dextrins and fragments thereof; synthetic hydrophilic polymers, such as poly(ethylene oxide), poly(vinyl alcohol), and poly(N-vinyl pyrrolidone); and proteins, such as bovine serum albumin and human gamma globulin. Polysaccharides are the prefered water-soluble polymers for use in the invention. Particularly, hyaluronic acid and sodium alginate are polysaccharides that are biocompatible and biodegradable in human tissue. They are non-cytotoxic, non-carcinogenic, non-inflammatory, non-pyrogenic, and non-immunogenic, and, therefore, in the form of gel microspheres, they are good candidates for delivery of drugs in accordance with the present invention.

Many crosslinking agents are known in the art. Some form covalent bonds with various functional groups, while others form ionic bonds. The present invention contemplates the formation of polymer particles which are crosslinked through covalent bonds, ionic bonds, or both.

Selection of the particular crosslinking agent for use in the process of the invention will depend upon the particular functional groups present in the water-soluble polymer to be crosslinked. For example, it is known that glutaraldehyde crosslinks amino groups and that XAMA-7 crosslinks carboxyl groups. Divinyl sulfone and epichlorhydrin crosslink hydroxyl and amino groups, and carbodiimides crosslink amino and carboxyl groups. Many epoxides, for example, EGDE and BDDE, crosslink hydroxy groups. The selection of an appropriate crosslinking agent can readily be accomplished by those of skilled in the art.

Examples of crosslinking agents which will be found satisfactory in the present invention include, without limitation, pentaerythritol-tris-[beta (N-aziridinyl)-propionate], divinyl sulfone, XAMA-7, epichlorhydrin, glutaraldehyde, p-toluene sulfonic acid, carbodiimides, epoxides, especially di- and polyepoxides, and ammonium persulfate. These crosslinking agents form covalent bonds with the water-soluble polymers in the process of the invention.

Ions of various alkali metals, alkaline earth metals, and transition metals can also be used to crosslink the water-soluble polymers employed in the present invention. Examples of these metals include, but are not limited to, calcium, magnesium, sodium, potassium, chromium, iron, copper, and zinc. For example, the calcium ion is known to crosslink water-soluble polymers that contain carboxyl groups. These crosslinking agents form ionic bonds with the water-soluble polymers in the process of the invention.

Ionic bonds may be broken down by a change in external conditions, e.g., by chelating agents. On the other hand, covalent bonds are stable in the presence of chelating agents and other external conditions which break ionic bonds. Thus, the most preferred crosslinking agents for use in the practice of the invention are those that form covalent bonds with the water-soluble polymer.

The crosslinking agent can be added to the aqueous polymer solution prior to emulsification, to the dispersion of water-soluble droplets in the oil phase, or, in some cases, to the inverted emulsion. The order of addition of the crosslinking agent will depend not only upon the particular polymer and crosslinking agent chosen but also upon the rate of the crosslinking reaction. An important consideration is that the rate of crosslinking not be such that it is competitive with the emulsification. Preferably, the crosslinking reaction is slow enough to permit complete emulsification of the aqueous and oil phases. Optionally, the crosslinking agent may be added to the aqueous polymer solution, and the pH of the solution adjusted to suitably slow down the rate of crosslinking prior to the solution being added to, and emulsified with, the oil phase. Subsequently, the pH is adjusted to provide the desired rate of crosslinking reaction.

Optionally, a catalyst can be added to initiate the crosslinking reaction. Choice of a particular catalyst will depend upon the particular water-soluble polymer selected, as well as the crosslinking agent, and other reaction conditions. The selection of any particular catalyst, in any case, can be readily done by those skilled in the art. Examples of catalysts that can be used in the practice of the invention include, but are not limited to, p-toluene sulfonic acid and hydrochloric acid. Optionally, heat may be provided as the catalyst in some cases.

The oil phase (i.e. the non-aqueous solvent phase) can be any inert hydrophobic liquid which can be readily separated from the dispersion of water-swellable polymer particles. In general, any hydrocarbon can be used as the oil phase liquid. Preferably, the hydrocarbon is toluene, o-xylene, or isooctane. Of concern, however, is that the crosslinking agent should not be soluble in the oil phase. Neither should the water-soluble polymer solution be soluble or miscible with the hydrocarbon used as the oil phase. Preferably, the hydrocarbon should also be substantially pure, although mixtures of hydrocarbons may be used. Preferably, the hydrocarbon is substantially non-volatile and non-polar. Those skilled in the art will be able to chose a suitable hydrocarbon for use in the practice of the invention. Although not critical to the invention disclosed herein, the hydrocarbon chosen, from a practical standpoint, should be low in cost.

In order to emulsify the water-soluble polymer phase into the oil phase to give a water-in-oil emulsion, one or more emulsifying agents of the water-in-oil type (a surfactant) are used in the amount of from about 0.010 to about 10.0 weight percent of the oil phase. Any commonly used water-in-oil emulsifying agent can be used in the practice of the invention, for example, hexadecyl sodium phthalate, sorbitan monostearate, metal soaps, and the like. Nevertheless, how well a given emulsifier works in any particular case depends upon the polymer solution to be emulsified, the composition of the oil phase, and the means of emulsification.

The emulsifier must function to stabilize the water-in-solvent system of the invention sufficiently to permit controlled crosslinking of the hydrophilic polymers to yield particles that are substantially homogeneous in size and shape, i.e. approximately 80% of the particles are within one standard deviation of the mean size, and at least approximately 95% of the particles are spherical. Otherwise, the aqueous phase particles will agglomerate and eventually form one continuous water-layer.

The choice of emulsifiers depends upon a number of factors including the water-soluble polymer selected and the size of the particles to be formed. It is important to match the properties of the emulsifier with the size and properties of the particles to be produced. Important emulsifier properties to be considered in this choice are the molecular length and charge of the emulsifier. Another important factor is the ability of the emulsifier to wrap different amounts of water molecules, allowing for the production of different size microspheres.

Still another important property in choosing an emulsifier is its ability to maintain a hydrophile-lipophile balance. This hydrophile-lipophile balance is the balance between the size and strength of the hydrophilic (water-loving or polar) and the lipophilic (oil-loving or non-polar) functional groups on the emulsifier.

Emulsifiers useful in the invention have low HLB (Hydrophile-Lipophile Balance) values, generally HLB values of less than approximately 8, preferably less than approximately 6, more preferably between about 4 and about 6. A particularly prefered emulsifier is SPAN 60. Those skilled in the art can readily determine, which water-in-oil emulsifier, i.e. surfactant., to use in any given case.

The crosslinking reaction is controlled to some extent by the particular reactants involved, the concentration of the reactants, the length of reaction time, the temperature, and the pH of the reaction mixture. The ratio of the weight of the water-soluble polymer to that of the crosslinking agent will depend upon the particular polymer and crosslinking agent employed. This ratio can vary from about 0.2 to about 200, preferably from about 1 to about 10.

The extent of crosslinking of the polymer droplets is generally controlled by controlling the length of the reaction time while maintaining the reaction at room temperature. In any particular case, the most suitable reaction time can be readily determined by those skilled in the art. In some cases the crosslinking reaction can be stopped by the addition of an alcohol, such as methanol or isopropanol, to the reaction mixture. The hydroxyl groups of the alcohol react with the functional groups of the crosslinking agent, quenching the reaction with the water-soluble polymer. The pH of the reaction mixture can be adjusted to control the rate of crosslinking, for example, by addition of a base, such as ammonium hydroxide, or an acid, such as acetic or hydrochloric acid, to the reaction mixture. The combination of reaction rate and reaction time determines the extent of crosslinking of the polymer droplets.

The extent of crosslinking is important to the present invention because it determines the rigidity and elasticity of the resulting water-swellable polymer particles. Elasticity is important because it allows the microspheres to be injected through a narrow guage needle. The elasticity of the microspheres is determined by the porosity and pore size. The porosity and pore size in turn are determined by the ratio of crosslinker to base polymer and by the homogeneity of the components within each microsphere. Optionally, a second surfactant can be employed to assist in obtaining and maintaining the homogeneity of the particles.

Unlike the emulsifier, this second surfactant is a solubilizer having an HLB between about 10 and about 18, preferably between about 12 and about 18, more preferably between about 14 and about 16. The use of such a surfactant is not essential, but promotes the homogeneity, elasticity, and clarity of the microspheres.

The extent and type of crosslinking is also important to the present invention because it prevents rapid breakdown of the microspheres in the body. Unlike, the process of Rothman, et al. (U.S. Pat. No. 4,124,705) the selection of water-soluble polymer and crosslinker allows for multiple types of linkages. Nonlimiting examples of the types of linkages formed by the process of the present invention are $\alpha(1\rightarrow4)$, $\alpha(1\rightarrow3)$, $\alpha(1\rightarrow1)$, $\beta(1\rightarrow4)$, and $\beta(1\rightarrow6)$. In part, multiple types of linkages are formed because of the different functional groups on the water-soluble polymer. For example, different polysaccharides have different numbers of hydroxyl groups located at different positions on the sugar ring. Each of these hydroxyl groups has a different reactivity to the crosslinker and forms different types of linkages. Because the process of the invention can crosslink any of these hydroxyl groups, the process of the invention is capable of forming many different types of linkages within the same polymer. This is also true of water-soluble polymers having other types of functional groups, including polymers having multiple types of functional groups. The number and type of different linkages can be controlled through selection of the reaction components and parameters.

The extent of agitation of the emulsion during droplet formation depends not only upon the recipe of the reactants involved in any particular case but also upon the size of the particles to be formed. For example, as will become more apparent hereinafter, toluene containing SPAN 60 emulsifying agent, i.e. sorbitan monostearate having a HLB of about 4.7, which is available from ICI Americas, can be used to make microscopic-size particles, e.g., 50 micrometers in diameter, or submicroscopic-size particles, e.g., 0.2 micrometers in diameter, according to the concentration of the SPAN 60 and the degree of agitation.

In general terms, as the concentration of the emulsifier increases, the size of the particles formed decreases. This is because the emulsifier stabilizes the individual microspheres and inhibits their agglomeration. Similarly, as the degree of agitation increases, the size of the particles formed decreases. The prefered degree of agitation in the present invention is a moderate agitation of about 100 rpm to about 600 rpm by stirring, more preferably about 200 rpm to 400 rpm. This level of agitation is sufficient to form particles in the range of about 10 micrometers to about 250 micrometers and to mix the particles after formation without destroying them. If a lower level of agitation is used, larger particles will result. If the level of agitation becomes too low, the microspheres will agglomerate, forming large aggregates. On the other hand, if a higher level of agitation is used, submicron particles will result. It is not possible to control the uniformity of the size and/or shape of such submicron particles. These submicron particles are not advantageous for implants, soft tissue augmentation, or tissue scaffolding because they easily migrate to different organs or undergo endocytosis by inflammatory cells of the host, such as neutrophils and macrophages.

The separation of the crosslinked particles from the aqueous phase can be accomplished by various known procedures. Generally, after inversion of the polymer particles into an aqueous phase, the oil layer is separated from the aqueous phase, e.g., by sedimentation, leaving an aqueous dispersion of crosslinked polymer particles. Then, the crosslinked water-soluble polymer particles are separated from the aqueous phase by filtration, after which the particles are washed and dehydrated with methanol. The particles are then dried. This can be done by merely spreading the particles out on a flat surface; however, in the case of an industrial scale operation, the particles can be dried in a fluidized bed drier conventionally used for such a purpose.

The particles may be microcapsules, microspheres, or beads. Microcapsules are defined as polymer particles containing one or more encapsulated compositions. Preferably, the encapsulated compositions are drugs, for example, but not limited to, antigens, antibodies, growth factors, inhibitors, antibiotics, antisense oligonucleotides, antiviral compositions, anti-cancer compositions, therapeutic agents, and other compositions to be administered to a patient, or delivered to a specific site in a patient. Microcapsules are large enough to be seen by the naked eye. Microspheres, on the other hand, are much smaller particles that generally do not contain encapsulated materials. Moreover, they may require optical lo microscopy to be seen. Beads are spherically-shaped particles that are large enough to be seen with the naked eye. The limit of visibility of beads is in the range of from 60–100 micrometers in diameter.

The size of particles resulting from the practice of the invention, quite advantageously, can vary over a wide range of sizes, both microscopic and submicroscopic, according to the average droplet size of the emulsion, which depends upon the composition, type and concentration of emulsifier, as well as the emulsification procedure and conditions. The particles of the invention are generally between about 10 micrometers and about 250 micrometers in diameter. The polymer particles are preferably greater than about 10 micrometers and less than about 212 micrometers in diameter, more preferably greater than about 10 micrometers and less than about 150 micrometers in diameter. Advantageously, the particles formed are substantially homogeneous in size and shape. Another feature of the water-swellable polymer particles of the invention is that when dispersed in water and injected through a narrow guage hypodermic syringe needle (20–22 guage), a worm-like thread is formed. Injectability is an important chacteristic of the water-swellable microspheres when the particles are used for drug delivery or therapy.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Preparation of an Aqueous Dispersion of Water-Soluble Polymer Particles in the Shape of Crosslinked Microspheres This example shows the preparation of an aqueous dispersion of crosslinked water-soluble particles of sodium alginate in the shape of microspheres. The recipe is set forth in Table I below:

TABLE I

Recipe for Crosslinked Water-Soluble Polymer Particles

| Ingredient | Parts by Weight |
| --- | --- |
| Water | 100.00 |
| Sodium alginate water-soluble polymer | 7.00 |
| 30% Ammonium hydroxide to adjust pH to 10–11 | 18 drops |
| Toluene | 100.00 |
| SPAN 60 emulsifier | 1.00 |
| XAMA-7 crosslinking agent | 4.00 |
| Isopropanol dehydrating agent | 100.00 |

The ammonium hydroxide was added to a 5% aqueous solution of sodium alginate containing XAMA-7 pentaerythritol-tris-[beta-(N-aziridinyl)-propionate] crosslinking agent to adjust the pH to pH 11. With this crosslinking agent, this pH adjustment is critical to prevent premature crosslinking. The aqueous solution was then emulsified in a continuous toluene phase using SPAN 60 water-in-oil emulsifier to give a water-in-oil emulsion or dispersion of aqueous sodium alginate droplets containing the crosslinking agent. Once the emulsion was formed and the desired droplet size distribution was achieved, a small amount of acetic acid was added to lower the pH to 7–8. The sodium alginate droplets crosslink rapidly at this lower pH. The crosslinked polymer solution-in-oil dispersion was then inverted in an excess of water, after which the oil phase was separated from the aqueous dispersion to give an aqueous dispersion of crosslinked sodium alginate microspheres.

The emulsifier and conditions of agitation were selected to give the desired droplet size (and hence the desired polymer particle size). This size distribution was controlled, not only by the emulsifier used, but also by the type and intensity of agitation used to prepare the water-in-oil emulsion. The results of these experiments are shown in Table II.

particles were spherical, with few offsize smaller spheres or irregularly shaped particles. Thus, the data in Table II demonstrate that crosslinked sodium alginate particles having a spherical shape and a diameter of less than 150 micrometers can be prepared reproducibly using the XAMA-7 crosslinking agent, by adjusting the pH of the sodium alginate phase with ammonium hydroxide to pH 11, forming the water-in-oil emulsion, and subsequently lowering the pH to 7–8 with acetic acid to initiate rapid crosslinking of the polymers in the droplets to form polymer particles.

Five types of reaction flasks and stirrers were used in the practice of the invention. The first, designated as A, comprised a one-liter round-bottom flask equipped with a TEFLON polytetrafluoroethylene half-moon stirrer. The second, designated as B, comprised a two-liter kettle equipped with a stainless-steel turbine agitator and six baffles angled slightly in the direction opposite to that of the liquid rotation. The third, designated as C, was similar to B, but of one-half-liter capacity and without the baffles. The fourth, designated as D, was similar to C, but equipped with a Glas-Col GKH Stir Tester to control the speed of emulsification despite the varying loads imposed by the emulsification. The fifth, designated as E, was similar to D, but equipped with a Glas-Col GKH Stir Tester and a stainless-steel turbine shaft. This reaction flask C was used in run S-48 through S-54 shown in Table II.

EXAMPLE 2

Microspheres Obtained from Crosslinked Droplets of Sodium Alginate/Methyl Cellulose In another experiment, 50.0 g water containing 2.25 g dissolved sodium alginate and 0.25 g Methocel K4M methyl cellulose (5% w/wsodium alginate/Methocel K4M) was dispersed in 75.0 g isooctane containing 1.5 g SPAN 85 (sorbitan trioleate, HLB 1.8, ICI Americas) in the one-half liter C kettle and stirred (about 1000 rpm) for about 10 minutes. Then, 5.0 g water containing 1.0 g TWEEN 85 (ethoxylated sorbitan trioleate, HLB 11.0, ICI Americas) was added, and the dispersion was stirred for another 5 minutes. To crosslink the droplets formed by the dispersion, an equivalent amount of the XAMA-7 crosslinking agent or its aqueous solution was added and allowed to react with the dispersed polymer droplets for 180 minutes. Then, 25 ml isopropanol was added to dehydrate and harden the crosslinked microspheres. The stirring was continued for 10

TABLE II

Particle Size Distribution of Aqueous Sodium Alginate Dispersions

| Run No. | S-48 | S-49 | S-50 | S-51 | S-52 | S-53 | S-54 |
| --- | --- | --- | --- | --- | --- | --- | --- |
| Initial pH* | 8 | 10–11 | 10–11 | 10–11 | 10–11 | 10–11 | 10–11 |
| Final pH** | 8 | 7-8 | 7-8 | 7-8 | 7-8 | 7-8 | 7-8 |
| Stirring rate (rpm) | 1000 | 900 | 800 | 800 | 1200 | 1000 | 1000 |
| Microsphere Size (%) | | | | | | | |
| >250 um | 13.5 | 7.1 | 7.4 | 5.1 | 3.9 | 8.9 | 12.3 |
| 212–250 um | 4.1 | 2.3 | 8.8 | 4.2 | 3.8 | 2.1 | 2.8 |
| 150–212 um | 11.7 | 11.6 | 23.5 | 14.7 | 11.8 | 26.9 | 8.3 |
| <150 um | 70.3 | 79.0 | 60.3 | 70.1 | 80.6 | 82.2 | 76.6 |

*after addition of ammonium hydroxide
**after addition of acetic acid

Table II shows the polymer microsphere size distribution achieved under various conditions. Substantially all of the minutes, after which the mixture separated into a clear supernatant layer and an opaque, white sedimented microsphere layer. The filtration of the microspheres proved to be difficult; therefore, the supernatant layer was decanted, and the sedimented microspheres were washed twice by stirring overnight in a beaker with 200 ml isopropanol. The microspheres were then filtered on filter paper without difficulty and dried at room temperature.

EXAMPLE 3

Effect of pH Control on the Crosslinking of the Water-Soluble Polymer Droplets to Form Microspheres Suitable for Drug Delivery This example demonstrates the effect of pH control on the crosslinking of the water soluble polymer droplets in the formation of microspheres suitable for drug delivery. 100 g of an aqueous solution containing 7.00 g sodium alginate and 4.0 g XAMA-7 crossing agent were mixed with 18 drops 30% aqueous ammonia to adjust the pH to 11. This solution was then dispersed in 100 g toluene containing 1.00 g SPAN 60 in the 0.5 liter stirred flask C using the stainless steel turbine agitator for 30 minutes at about 1000 rpm. The formation of the microscopic droplet size of the water soluble polymer in the water-in-oil emulsion was monitored by optical microscopy while the emulsion was being stirred. When the emulsion was judged satisfactory, sufficient acetic acid was added to decrease the pH of the aqueous phase to 7–8. This mixture was then stirred for about 4–5 hours at room temperature to allow the XAMA-7 to crosslink the sodium alginate droplets to form microspheres. Then, the aqueous liquid layer was separated by decantation. The microspheres were then washed twice with about 200 ml methanol by sedimentation-decantation, then filtered and dried at 75° C.

All of the microspheres obtained, when dispersed in water and injected through a hypodermic syringe, formed worm-like threads indicating the microspheres were suitable for drug delivery.

EXAMPLE 4

Size Distribution of Cross-linked Sodium Alginate Microspheres Obtained

Other dispersions of sodium alginate were prepared using the recipe shown in Table III below to determine particle size distribution:

TABLE III

Recipe for Crosslinked Water-Soluble Polymer Particles

| Ingredient | Parts by Weight |
| --- | --- |
| Water | 150.00 |
| Sodium alginate water-soluble polymer | 10.50 |
| pH (controlled by addition of 30% ammonium hydroxide) | 10–11 |
| Toluene | 150.00 |
| SPAN 60 emulsifier | 1.50 |
| XAMA-7 crosslinking agent | 6.00 |
| pH (controlled by addition of 10% acetic acid) | 7–8 |
| Isopropanol dehydrating agent | 150.00 |

161 g of an aqueous solution containing 10.50 g sodium alginate was mixed with sufficient 30% aqueous ammonia to adjust the pH to 10–11. This solution was dispersed in 150 g toluene containing 1.50 g SPAN 60 in the 0.5 liter capacity stirred D flask using the stainless steel turbine agitator, as earlier disclosed, for 30 minutes at 1000 rpm. The droplet size was monitored by optical microscopy while the emulsion was being stirred. When it was deemed satisfactory, sufficient 10% acetic acid was added to lower the pH of the aqueous phase to 7–8. This mixture was then stirred for 6 hours at room temperature to allow the XAMA-7 to crosslink the sodium alginate droplets. Following crosslinking, 150 g isopropanol was added to dehydrate the beads. The stirring was continued for another 30 minutes. Afterwards, the liquid layer was separated by decantation. The microspheres were washed twice with about 200 ml methanol by sedimentation-decantation, then filtered, and dried at 75° C.

The size distributions for the microspheres obtained in each case is given in Table IV.

TABLE IV

Particle Size of Aqueous Sodium Alginate Dispersions

| Run. No. | S-56 | S-57 | S-58 |
| --- | --- | --- | --- |
| Reaction flask | E | E | E |
| Reaction time (hr) | 6 | 6 | 6 |
| Stirring rate (rpm) | 1000–800 | 800 | 1000 |
| Microsphere Size (%) | | | |
| a. >250 um | 10.6 | 6.4 | 6.4 |
| b. 212–250 um | 3.1 | 4.5 | 1.8 |
| c. 150–212 um | 7.0 | 15.4 | 9.3 |
| d. <150 um | 79.0 | 73.6 | 82.6 |
| Spherical morphology of microspheres | | | |
| before pH 7–8* | good | good | good |
| after pH 7–8** | good | good | good |
| small particles*** | ++ | + | ++ |
| irregular particles*** | ++ | ++ | + |

*after addition of ammonium hydroxide
**after addition of acetic acid
***+ — few particles; ++ — more particles All of the microspheres obtained in these experiments, when dispersed in water and injected through a hypodermic syringe, formed the desirable worm-like threads.

EXAMPLE 5

Effect of XAMA-7 Crosslinking Agent at Various Concentrations in Aqueous Solution at pH 7

This example is to show the effect of the crosslinking agent at various concentrations in the aqueous polymer solution on the formation of microspheres.

Three problems were encountered in the first experiments with the XAMA-7 crosslinking system: (1) The microsphere distribution was broader than desired; (2) The proportion of sodium alginate in the crosslinked polymer was too low and that of the XAMA-7 crosslinking agent was too high; and (3) The microspheres tended to aggregate.

To investigate the sodium alginate/XAMA-7 crosslinking agent reaction, the reaction was conducted in aqueous solution without the emulsification system. These reactions were carried out in small glass vials; the sodium alginate and XAMA-7 crosslinking agent were mixed together in the vial. The time to gelation was taken as the time after mixing at which the gel no longer flowed when the sample vial was inverted.

Generally, the sodium alginate/XAMA-7 solution became progressively more viscous until, finally, it formed a near-solid gel that would not flow when the sample vial was inverted. According to the manufacturer, the XAMA-7 crosslinking agent reacts rapidly with carboxyl or hydroxyl groups at pH 7 but much more slowly at pH 11. Therefore, the time required for gelation in an aqueous solution of sodium alginate was measured at pH 7. The same pH was used in the experiments in which water or methanol or isopropanol was used in the absence of sodium alginate.

The results of these experiments are shown below in Table V.

TABLE V

The Effect of XAMA-7 Concentration at pH 7 on Crosslinking 2.0% Sodium Alginate in Water

| Run No. | Water (g) | Sodium Alginate (g) | XAMA-7* (%) | XAMA-7* (g) | Gelation Time (hr) |
|---|---|---|---|---|---|
| 1 | 2.0 | 0.04 | 2.0 | 0.20 | 1.0 |
| 2 | 2.0 | 0.04 | 2.0 | 0.10 | 1.5 |
| 3 | 2.0 | 0.04 | 2.0 | 0.05 | >24 |

Water without Sodium Alginate

| Run No. | Water (g) | Sodium Alginate (g) | XAMA-7* (%) | XAMA-7* (g) | Gelation Time (hr) |
|---|---|---|---|---|---|
| 4 | 2.0 | — | — | 0.20 | 2.7 |
| 5 | 2.0 | — | — | 0.10 | 48 |
| 6 | 2.0 | — | — | 0.05 | >48 |

Water with Methanol, No Sodium Alginate

| Run No. | Water (g) | Methanol (g) | XAMA-7* (%) | XAMA-7* (g) | Gelation Time (hr) |
|---|---|---|---|---|---|
| 7 | 2.0 | 0.20 | 10.0 | 0.20 | 12 |
| 8 | 2.0 | 0.20 | 10.0 | 0.10 | >12 |
| 9 | 2.0 | 0.20 | 10.0 | 0.05 | >24 |

Water with Isopropanol, No Sodium Alginate

| Run No. | Water (g) | Isopropanol (g) | XAMA-7* (%) | XAMA-7* (g) | Gelation Time (hr) |
|---|---|---|---|---|---|
| 10 | 2.0 | 0.20 | 10.0 | 0.20 | 15 |
| 11 | 2.0 | 0.20 | 10.0 | 0.10 | >15 |
| 12 | 2.0 | 0.20 | 10.0 | 0.05 | no reaction |

*as a 5% solution

The results shown in Table V confirm that XAMA-7 is an active crosslinking agent. It reacted with the carboxyl and hydroxyl groups of the sodium alginate, and, in the absence of sodium alginate, it reacted with water or itself to give gelation times almost as short. It also reacted with the isopropanol used to stop the reaction or the methanol used to wash the microspheres.

The order of reactivity with the crosslinking agent is seen from the table to be sodium alginate (carboxyl groups), followed by water, methanol, and isopropanol. The side reaction of the crosslinking agent with water formed hydroxyl groups that could stabilize the microspheres. Also, the XAMA-7 crosslinking agent reacted with the isopropanol used to stop the reaction and the methanol used to wash the microspheres, and thus allowed the microspheres to be separated from the medium.

EXAMPLE 6

Effect of Concentration of Water-Soluble Polymer In Aqueous Solution Relative to that of Crosslinking Agent The original ratio of the weight of sodium alginate/XAMA-7 crosslinking agent in the aqueous solution was 0.4. This ratio, it was discovered, is too low; indeed, the microspheres resulting from such a ratio comprised poly (XAMA-7) crosslinked with the sodium alginate polymer, rather than the opposite. Therefore, it was considered important to reduce the concentration of XAMA-7 crosslinking agent in the aqueous solution relative to that of the sodium alginate.

To each of four vials was added 2.0 g water, 1.0 g 2.0–5.0% sodium alginate solution, and 0.05 g XAMA-7 crosslinking agent as a 5% solution, at pH 7. The sodium alginate/XAMA-7 crosslinking agent ratio was increased from 0.4 to 1.0.

These reactions were investigated in aqueous solutions without the emulsifying system. The results of these experiments are given in Table VI below:

TABLE VI

The Effect of Sodium Alginate Concentration at pH 7

| Run No. | Sodium Alginate Solution (g) | Sodium Alginate Solution (%) | XAMA-7* (g) | Na Alg/XAMA-7 Ratio | Gelation Time (hr) |
|---|---|---|---|---|---|
| 2-7-1 | 1.0 | 2.0 | 0.05 | 0.4 | 5.0 |
| 3-7-1 | 1.0 | 3.0 | 0.05 | 0.6 | 5.0 |
| 4-7-1 | 1.0 | 4.0 | 0.05 | 0.8 | 2.5 |
| 5-7-1 | 1.0 | 5.0 | 0.05 | 1.0 | 1.0 |

*as a 5% solution

The properties of the crosslinked microsphere varied with the sodium alginate/XAMA-7 crosslinking agent ratio. This was shown by the behavior of the microspheres when they were dispersed in water and forced through the needle of a hypodermic syringe.

Increasing the sodium alginate concentration to 5.0%, as seen from Table VI decreased the gelation time from 5 hours to 1 hour. The higher viscosity of the 5% sodium alginate solution made it difficult, however, to mix it with the crosslinking agent solution. Nevertheless, the viscosity was still low enough for the experiments to be carried out in the laboratory.

EXAMPLE 7

Effect of Sodium Alginate Concentration at a Constant Concentration of Crosslinking Agent This example shows the corresponding effect of increasing the sodium alginate concentration at a constant XAMA-7 crosslinking agent concentration at pH 8. These reactions, like those in Example 6, were investigated in aqueous solutions without the emulsifying system. The data is shown in Table VII.

TABLE VII

The Effect of Sodium Alginate Concentration at pH 8

| Run No. | Sodium Alginate Solution (g) | Sodium Alginate Solution (%) | XAMA-7* (g) | Na Alg/XAMA-7 Ratio | Gelation Time (hr) |
|---|---|---|---|---|---|
| 2-8-1 | 1.0 | 2.0 | 0.05 | 0.4 | 3.0 |
| 3-8-1 | 1.0 | 3.0 | 0.05 | 0.6 | 3.0 |
| 4-8-1 | 1.0 | 4.0 | 0.05 | 0.8 | 1.5 |
| 5-8-1 | 1.0 | 5.0 | 0.05 | 1.0 | 1.2 |

*as a 5% solution

The results, as seen from Table VII, are similar to those at pH 7 (Example 6), except that the rate of gelation was slightly slower. Increasing the sodium alginate concentration from 2.0% to 5.0% decreased the gelation time from 3 hours to 1.2 hours.

EXAMPLE 8

Effect of XAMA-7 Concentration and pH at Higher Concentrations of Sodium Alginate This example is to show the effect of the concentration of crosslinking agent and pH at higher concentrations of sodium alginate. These reactions, as in Example 6, were investigated without the emulsion system. The results are given in Table VIII.

TABLE VIII

Effect of XAMA-7 Concentration and pH at Higher Sodium Alginate Concentration

| Run No. | pH | Sodium Alginate Solution (g) | XAMA-7 (g) | Na Alg/ XAMA-7 Ratio | Gelation Time (min) |
|---|---|---|---|---|---|
| 6% Sodium Alginate in 2.0 g Water | | | | | |
| 6-6-1 | 6.0 | 2.0 | 0.10 | 1.2 | 41* |
| 6-6-2 | 6.0 | 2.0 | 0.08 | 1.5 | 41* |
| 6-6-3 | 6.0 | 2.0 | 0.06 | 2.0 | 82* |
| 6-6-4 | 6.0 | 2.0 | 0.04 | 3.0 | >240** |
| 7% Sodium Alginate in 2.0 g Water | | | | | |
| 7-7-1 | 7.0 | 2.0 | 0.10 | 1.2 | 11*** |
| 7-7-2 | 7.0 | 2.0 | 0.08 | 1.5 | 11*** |
| 7-7-3 | 7.0 | 2.0 | 0.06 | 2.0 | 30**** |
| 7-7-4 | 7.0 | 2.0 | 0.04 | 3.0 | >30**** |
| 7-8-1 | 8.0 | 2.0 | 0.10 | 1.2 | 30 |
| 7-8-2 | 8.0 | 2.0 | 0.08 | 1.5 | 50 |
| 7-8-3 | 8.0 | 2.0 | 0.06 | 2.0 | 180 |
| 7-8-4 | 8.0 | 2.0 | 0.04 | 3.0 | >480 |
| 7-9-1 | 9.0 | 2.0 | 0.10 | 1.2 | 30 |
| 7-9-2 | 9.0 | 2.0 | 0.08 | 1.5 | 50 |
| 7-9-3 | 9.0 | 2.0 | 0.06 | 2.0 | 180 |
| 7-9-4 | 9.0 | 2.0 | 0.04 | 3.0 | >480 |
| 7-10-1 | 10.0 | 2.0 | 0.10 | 1.2 | 45 |
| 7-10-2 | 10.0 | 2.0 | 0.08 | 1.5 | 180 |
| 7-10-3 | 10.0 | 2.0 | 0.06 | 2.0 | — |
| 7-10-4 | 10.0 | 2.0 | 0.04 | 3.0 | >480 |
| 7-11-1 | 11.0 | 2.0 | 0.10 | 1.2 | >48 |
| 7-11-2 | 11.0 | 2.0 | 0.08 | 1.5 | >48 |
| 7-11-3 | 11.0 | 2.0 | 0.06 | 2.0 | >48 |
| 7-11-4 | 11.0 | 2.0 | 0.04 | 3.0 | — |

*turned cloudy in 5 min., opaque white in 30 min.
**turned cloudy in 30 min., opaque white in 60 min.
***turned cloudy in 3 min., opaque white in 6 min.
****turned cloudy and opaque white in 12 min.
XAMA-7 added as a 5% solution Table VIII shows the effect of XAMA-7 crosslinking agent concentrations and pH at 6.0 and 7.0% sodium alginate concentrations. The pH was varied from 6.0 to 11.0. Generally, the gelation times increased with increasing pH, e.g., from 11 minutes at pH 7 to more than 48 hours at pH 11. The gelation times at pH 6 were longer than those at pH 7.

In general, as seen from Table VIII, the gelation time increased with decreasing XAMA-7 concentration at a given pH, e.g., from 11 minutes at 0.10 g XAMA-7 crosslinking agent to more than 30 minutes for 0.04 g XAMA-7 crosslinking agent.

EXAMPLE 9

Effect of Various Concentrations of XAMA-7 And Varying pH on Gelation Times for Sodium Alginate The effect of the XAMA-7 crosslinking agent concentration at pH values ranging from 6.4 to 11.0 for a 6.0% sodium alginate concentration is shown in Table IX.

TABLE IX

Effect of XAMA-7 Concentration and pH at 6% Sodium Alginate Concentration

6% Sodium Alginate in 2.0 g Water

| Run No. | pH | Sodium Alginate Solution (g) | XAMA-7 (g) | Na Alg/ XAMA-7 Ratio | Gelation Time (min) |
|---|---|---|---|---|---|
| 6-6-1 | 6.0 | 2.0 | 0.10 | 1.2 | 41* |
| 6-6-2 | 6.0 | 2.0 | 0.08 | 1.5 | 41* |
| 6-6-3 | 6.0 | 2.0 | 0.06 | 2.0 | 82* |
| 6-6-4 | 6.0 | 2.0 | 0.04 | 3.0 | >240** |
| 6-6-1 | 6.4 | 2.0 | 0.10 | 1.2 | 96* |
| 6-8-1 | 8.0 | 2.0 | 0.10 | 1.2 | 96** |
| 6-9-1 | 9.0 | 2.0 | 0.10 | 1.2 | 125** |
| 6-10-1 | 10.0 | 2.0 | 0.10 | 1.2 | — |
| 6-11-1 | 11.0 | 2.0 | 0.10 | 1.2 | *** |

*turned cloudy in 6 min., opaque white at 25 min.
**turned cloudy in 9 min., opaque white in 25 min.
***very slow reaction

| 6-6-2 | 6.4 | 2.0 | 0.08 | 1.5 | 200* |
| 6-8-2 | 8.0 | 2.0 | 0.08 | 1.5 | 200* |
| 6-9-2 | 9.0 | 2.0 | 0.08 | 1.5 | 200** |
| 6-10-2 | 10.0 | 2.0 | 0.08 | 1.5 | >200*** |
| 6-11-2 | 11.0 | 2.0 | 0.08 | 1.5 | **** |

*turned opaque white in 42 min., formed immobile gel
**turned opaque white in 42 min., gel flowed slowly
***turned opaque white in 42 min., gel flowed easily
****clear liquid after 200 min.

| 6-6-3 | 6.4 | 2.0 | 0.06 | 2.0 | 260* |
| 6-8-3 | 8.0 | 2.0 | 0.06 | 2.0 | 260* |
| 6-9-3 | 9.0 | 2.0 | 0.06 | 2.0 | 260** |
| 6-10-3 | 10.0 | 2.0 | 0.06 | 2.0 | >260*** |
| 6-11-3 | 11.0 | 2.0 | 0.06 | 2.0 | **** |

*turned opaque white in 45 min.
**turned opaque white in 45 min., gel flowed slowly
***gel flowed easily
****clear liquid after 260 min.

| 6-6-4 | 6.4 | 2.0 | 0.04 | 3.0 | 300* |
| 6-8-4 | 8.0 | 2.0 | 0.04 | 3.0 | 300* |
| 6-9-4 | 9.0 | 2.0 | 0.04 | 3.0 | 300* |
| 6-10-4 | 10.0 | 2.0 | 0.04 | 3.0 | >300* |
| 6-11-4 | 11.0 | 2.0 | 0.04 | 3.0 | ** |

*flowed when inverted
**remained a clear liquid
XAMA-7 added as a 5% solution

The reactions investigated in Example 9 were made on the aqueous solutions without the emulsion system and were conducted as disclosed in Example 6.

At constant pH, the gelation time generally increased with decreasing XAMA-7 concentration, e.g., from about 100 minutes at 0.10 g XAMA-7 to about 200 minutes at 0.08 g and from about 260 minutes at 0.06 g to about 300 minutes at 0.04 g.

At a given XAMA-7 crosslinking agent concentration the gelation time generally increased with increasing pH, but the increase was not great. Nevertheless, none of the samples gelled within a reasonable time at pH 11. All samples gave the shortest gelation time at a pH 6.4 to 8.0.

These results show that the reaction between the sodium alginate and the XAMA-7 crosslinking agent can be controlled by the concentration of the reactants, as well as by pH.

EXAMPLE 10

Crosslinking of Water Soluble Polymers with Various Crosslinking Agents

Other crosslinking-in-solution experiments were carried out using different crosslinking agents and different water-soluble polymers. The results are shown below in Table X.

TABLE X

Crosslinking with Different Crosslinking Agents

| Polymer | Glutaraldehyde pH 2 | XAMA-7 pH 2 | Divinyl Sulfone pH 10 | Borate pH 8–9 |
|---|---|---|---|---|
| PVA | 0.10/0.10 precipitated | 0.10/0.10 clear | not soluble clear | 0.10/0.10 floaters |
| CS | 0.20/0.20 clear | 0.20/0.10 slight gel precipitated 0.40/1.0 precipitated 0.20/0.10 pH 7 opaque | 0.20/0.20 clear 0.40/1.0 precipitated | 0.10/0.10 clear |
| SA | 0.20/0.20 pH 4 opaque | 0.10/0.10 pH 7 precipitated 0.20/0.50 pH 7 highly gelled | 0.20/0.20 clear 0.40/0.10 highly gelled | 0.10/0.10 clear |

PVA = poly (vinyl alcohol)
CS = chondroitin sulfate
SA = sodium alginate
Borate = boric acid $H_3BO_3$ In the above Table X, the first number refers to the weight of the polymer and the second number to the weight of the crosslinking agent in g, e.g., the "0.10/0.10" in the upper lefthand column under Glutaraldehyde refers to a sample comprising 0.10 g poly(vinyl alcohol) i.e., PVA, and 0.10 g glutaraldehyde.

15 ml of the polymer solution containing the stated amount was mixed with the stated amount of crosslinking agent at room temperature. The pH was adjusted to the value set forth in the table with either sulfuric acid or sodium hydroxide. The formation of a visible gelled structure was taken as evidence that crosslinking had occurred.

The data shows that the glutaraldehyde (pH 2) crosslinked the poly(vinyl alcohol) and the sodium alginate (SA). The SA, however, crosslinked to a greater degree than the PVA. The glutaraldehyde failed to crosslink the chondroitin sulfate (CS). With XAMA-7, the CS gave a gel at the 0.20/0.10 ratio, a stiffer gel at the 0.40/0.10 ratio, and an opaque gel at the 0.20/0.10 ratio at pH 7. In the case of the sodium alginate, strong gels were given at pH 7 at both the 0.10/0.10 and 0.20/0.50 ratios.

The divinyl sulfone was insoluble in the aqueous poly (vinyl alcohol) at pH 10 and did not give a gel. With the chondroitin sulfate, no gel was given at the 0.20/0.20 ratio, but a gel was given at the 0.40/0.10 ratio. The sodium alginate gave no gel at the 0.20/0.20 ratio; however, a gel was formed at the 0.40/0.10 ratio.

The borate crosslinking agent at pH 8–9 gave structures that floated to the top of the sample in the case of the poly(vinyl alcohol). It did not crosslink the chondroitin sulfate or the sodium alginate.

EXAMPLE 11

Effect of Other Crosslinking Agents on the Crosslinking of Water-Soluble Polymer Particles Other crosslinking agents tested include the carbodiimides and epoxide crosslinking agents. These investigations as in the previous example were made without the emulsion system. The results of the experiments are shown in Table XI below:

TABLE XI

Crosslinking with Different Crosslinking Agents

| | Carbodiimide, pH 4 | | Epoxide, pH 10 | |
|---|---|---|---|---|
| Polymer | CHME-CDI | DMAPE-CDI | ECH | BDEP |
| PVA | 0.10/0.10 clear | 0.10/0.10 clear | 0.10/0.10 clear | 0.10/0.10 clear |
| CS | 0.18/0.18 clear 0.36/0.18 clear 0.18/0.18/0.05 precipitated 0.18/0.09/0.05 precipitated | 0.18/0.09/0.06 precipitated | 0.20/0.20 clear 0.40/1.0 precipitated | 0.20/0.20 clear 0.20/0.20 clear |
| SA | 0.18/0.18 clear 0.18/0.09 clear 0.18/0.09/0.06 opaque, gelled | 0.18/0.09 clear 0.18/0.18 clear 0.18/0.09/0.06 opaque, gelled | 0.20/0.20 clear 0.40/0.05 clear | 0.20/0.20 clear |

CHME-CDI = 1-cyclohexyl-3-(2-morpholinoethyl) carbodiimide
DMAPE-CDI = 1-(3-dimethylaminopropyl)-3-ethylcarbodiimide
ECH = epichlorhydrin
BDEP = 1,3-butadiene diepoxide 15 ml of the polymer solution containing the stated amounts of the polymers were mixed with the crosslinking agents at room temperature. The first number designates the weight in grams of the polymer; the second number designates the grams of crosslinking agent. Where a third number appears, this is the gram weight of 1,5-diaminopentane dihydrochloride.

The pH was adjusted with sulfuric acid or sodium hydroxide to 4 for the carbodiimides and to 10 for epoxide crosslinking agents. The formation of a visible gelled structure was taken as evidence that crosslinking had occurred.

As can be seen from Table XI, the poly(vinyl alcohol) gave clear solutions with equal weights (0.10 g) of the 1-cyclohexyl-3-(2-morpholinoethyl)carbodiimide (CHME-CDI), 1,(3-dimethylamino-propyl)-3-ethylcarbodiimide (DMAPE-CDI), epichlorhydrin (ECH), and 1,3-butadiene diepoxide (BDEP), which indicates that the hydroxyl groups of the poly(vinyl alcohol) are not sufficiently active to react with any of these crosslinking agents.

The chondroitin sulfate gave clear solutions with equal weights (0.18 g) of the polymer and 1-cyclohexyl-3-(2-morpholinoethyl)carbodiimide, and when the weight of the polymer was doubled to 0.36 g, which indicated that no significant crosslinking had occurred. When 0.05 g 1,5-diaminopentane dihydrochloride was added, along with 0.18/0.18, or 0.18/0.09, g of polymer/carbodiimide, the sample precipitated, indicating that crosslinking had occurred. Similar crosslinking was observed with the 1-(3-dimethylamino-propyl)-3-ethylcarbodiimide. The 1,3-butadiene diepoxide gave no crosslinking at the ratios used. The epichlorhydrin gave cross-linking at the 0.40/1.0 ratio but not at the 0.20/0.20 ratio.

The sodium alginate did not crosslink with equal weights (0.18 g) of the polymer and 1-(3-dimethylaminopropyl)-3-ethyl-carbodiimide, nor when the weight of the crosslinking was cut in half (0.09 g); however, upon addition of 0.06 g 1,5-diaminopentane dihydrochloride, the sample was crosslinked to an opaque gel. The results were similar with 1-cyclohexyl-3-(2-morpholinoethyl) carbodiimide. Equal weights (0.20 g) of epichorohydrin and 1,3-butadiene diepoxide gave clear solutions, even when the amount of sodium alginate was increased to 0.40 g and that of the epichorhydrin was reduced to 0.05 g, which indicated that no crosslinking had occurred.

EXAMPLE 12

Preparation of Microspheres of Water-Soluble Polymer by Inverse Emulsification Process of Invention Sodium alginate gel microspheres were prepared by using an inverse emulsification process. Table XII below gives the various recipes used in the inverse emulsification process.

Typically, 0.60 g of sodium alginate dissolved in 30.0 g of water was emulsified in 30.0 g toluene which contained 0.30 g SPAN 60, a water-in-oil emulsifier (1.0% by weight).

The samples were placed in 4 ounce glass bottles and shaken by hand to form the inverse emulsions of aqueous sodium alginate solution in toluene. The XAMA-7 crosslinking agent was next added to each bottle. The bottles were then capped and tumbled end-over-end for 24 hrs. at 25° C. During this time, the XAMA-7 crosslinking agent reacted with the sodium alginate and microspheres formed. After the reaction was completed, excess methanol was added to dehydrate the sodium alginate microspheres, which were then filtered out from the water phase and washed three times with methanol. The recovered and washed microspheres were then dried in an oven for 24 hours at 75° C.

TABLE XII

Recipes for the Preparation of Alginate Microspheres

| Run No. | S-01 | 02 | 03 | 04 | 04B | 06 | 07 | 08 |
|---|---|---|---|---|---|---|---|---|
| Sodium alginate (g) | 0.60 | 0.60 | 0.60 | 0.60 | 0.60 | 0.00 | 0.90 | 1.2 |
| Water (g) | 30.0 | 30.0 | 30.0 | 30.0 | 30.0 | 30.0 | 30.0 | 30.0 |
| Toluene (g) | 30.0 | 30.0 | 30.0 | 30.0 | 30.0 | 30.0 | 30.0 | 30.0 |
| Span 60 (g) | 0.30 | 0.30 | 0.30 | 0.30 | 0.30 | 0.30 | 0.30 | 0.30 |
| XAMA-7 (g) | 1.42 | 1.78 | 2.37 | 3.56 | 3.56 | 2.37 | 3.56 | 3.56 |
| d (ml) | 3.00 | 1.20 | 1.50 | 2.00 | 3.00 | 3.00 | 2.00 | 3.00 |

Runs S-04 and S-04B, which used the highest concentration of crosslinking agent, gave spherical microspheres with a broad distribution of sizes. The microspheres were stable and withstood drying at 75° C. overnight without distortion. The crosslinking reaction was judged to be essentially complete from the gravimetric material balance, e.g., in the case of Run S-04B, the original weight of sodium alginate plus that of the XAMA-7 crosslinking agent was 4.16 g, as compared to 4.02 g for the recovered weight of the microspheres. Samples of the microspheres were placed on microscope slides, washed with methanol to remove the SPAN 60, and examined by optical microscopy. All the microspheres were well-defined spheres, even after absorption of water. The microspheres of Run S-04 swelled and absorbed 63.6% water.

The XAMA-7 crosslinking agent concentration was increased at constant sodium alginate concentration in Runs S-01, S-02, S-03, and S-04. Generally, optical microscopy showed that both large and small microspheres were obtained. The larger microspheres appeared to be wrinkled in appearance, and only those of Run S-04 appeared to be spherical. These results were interpreted as the result of the reaction of the XAMA-7 crosslinking agent with the sodium alginate to give gelled microspheres.

The sodium alginate concentration was increased at constant (high) XAMA-7 crosslinking agent concentration in Run S-07 and Run S-08. These runs produced beads that were spheroidal rather than spherical in shape. The reason for the production of spheroidal beads is not actually known; however, possible reasons include non-uniform crosslinking of the original inverse emulsion droplets or partial coagulation of crosslinked beads.

In contrast, Run S-06, which contained the XAMA-7 crosslinking agent, but no sodium alginate, gave no beads. It gave, instead, an emulsion which disappeared within 30 minutes upon standing. Apparently, the sodium alginate, although present in only a small concentration, is necessary for the formation of a crosslinked network under these conditions. Condensation of the XAMA-7 crosslinking agent by itself does not, apparently, give a similar crosslinked structure.

EXAMPLE 13

Inverse Emulsification of Mixtures of Sodium Alginate and Methyl Cellulose to Obtain Crosslinked Microspheres and Size Distribution Table XIII gives the recipes and results for inverse emulsifications of sodium alginate and METHOCEL K4M methylcellulose mixtures using the XAMA-7 crosslinking agent.

Typically, 50.0 g water containing 2.25 g dissolved sodium alginate and 0.25 g methyl cellulose (5% w/w sodium alginate/methyl cellulose) were dispersed in 75.0 g isooctane containing 1.5 g SPAN 85 in the one-half liter kettle C, earlier disclosed, and stirred for 10 minutes. Then, 5.0 g water containing 1.0 g TWEEN 85, a general purpose water soluble emulsifier (a polyoxyethylene derivative of fatty acid partial ester of sorbitol anhydride) was added to the dispersion and the dispersion was stirred for another 5 minutes. An equivalent amount of the XAMA-7 crosslinking agent or its aqueous solution was then added to the dispersion. The crosslinking agent was then allowed to react with the dispersed polymer droplets for 180 minutes while being stirred, to crosslink the droplets. Then, 25 ml isopropanol was added to dehydrate and harden the microspheres formed. The stirring was continued for another 10 minutes, after which the mixture separated into a clear supernatant layer and an opaque, white sedimented microsphere layer. The filtration of the microspheres proved difficult; therefore, the supernatant layer was decanted, and the sedimented microspheres were washed twice by stirring overnight in a beaker with 200 ml isopropanol. Then, the microspheres were filtered easily on filter paper and dried overnight at room temperature.

TABLE XIII

Sodium Alginate/Methyl Cellulose Microspheres

| Run No. | WA-02 | WA-03 | WA-04 | WA-05 | WA-06 | WA-07 |
|---|---|---|---|---|---|---|
| Water Phase (g) | | | | | | |
| Sodium Alginate | 2.25 | 2.25 | 2.25 | 2.25 | 2.25 | 2.25 |
| Methocel K4M | 0.25 | 0.25 | 0.25 | 0.25 | 0.25 | 0.25 |
| Water | 50.0 | 50.0 | 50.0 | 50.0 | 50.0 | 50.0 |
| Oil Phase (g) | | | | | | |
| Isooctane | 75.0 | 75.0 | 75.0 | 75.0 | 75.0 | 75.0 |
| Span 85 | 1.50 | 1.50 | 1.50 | 1.50 | 1.50 | 1.50 |

TABLE XIII-continued

Sodium Alginate/Methyl Cellulose Microspheres

| Run No. | WA-02 | WA-03 | WA-04 | WA-05 | WA-06 | WA-07 |
|---|---|---|---|---|---|---|
| Emulsifier (g) | | | | | | |
| Tween 85 | 1.0 | 1.0 | 1.0 | 1.0 | 1.0 | 1.0 |
| Water | 5.0 | 5.0 | 5.0 | 5.0 | 5.0 | 5.0 |
| Crosslinking Agent (ml) | | | | | | |
| XAMA-7 | 11.3 | 10.0 | 9.0 | 9.0 | 6.5 | 11.3 |
| Water | 50.0 | 50.0 | — | — | — | — |
| Reaction Flask | C | C | C | C | C | C |
| React. Time (min) | 180 | 120 | 180 | 180 | 180 | 180 |
| Microsphere Size (%) | | | | | | |
| a. >250 um | 0.0 | 28.9 | 6.0 | 5.4 | 11.5 | 11.6 |
| b. 250–212 um | 0.0 | 1.5 | 1.4 | 0.0 | 0.0 | 2.9 |
| c. 212–150 um | 5.0 | 2.9 | 3.0 | 1.8 | 2.6 | 7.2 |
| d. <150 um | 93.8 | 66.6 | 90.5 | 92.5 | 86.0 | 75.0 |

These experiments show that crosslinked sodium alginate/Methocel K4M beads of diameters mostly smaller than 150 micrometers can be prepared reproducibly using isooctane as the continuous phase, SPAN 85 as the emulsifying agent, and XAMA-7 as the crosslinking agent.

EXAMPLE 14

Sodium Alginate Microspheres Prepared by Inverse Emulsification and Crosslinked by Calcium Ions In this example, divalent calcium ions were used to crosslink the sodium alginate to obtain a comparison with the XAMA-7 crosslinking agent.

Calcium chloride was first used to crosslink sodium alginate about 20 years ago (M. Kiestan and C. Burke, Biotechnol. Bioeng. 19, 387–97 (1977)); a 2–4% aqueous sodium alginate solution was injected into a 2% aqueous calcium chloride solution to form large hydrophilic crosslinked sodium alginate beads. This process was not an emulsification in the usual sense, but instead produced microspheres by the crosslinking of sodium alginate by calcium ions at the interface between the aqueous sodium alginate and calcium chloride phases. In general, this method gave microcapsules with a broad distribution of sizes of 10–2000 micrometers diameter; however, it was difficult to prepare smaller microspheres of 0.1–200 micrometers diameter.

For this example, sodium alginate microspheres were prepared by inverse emulsification and crosslinked with calcium ions, according to the method used by Wan et al., Proc. NUS-JPS Seminar on Recent Developments in Pharmaceutics and Pharmaceutical Technology, 1990, pp. 243–55; ibid., J. Microencapsulation 9(3), 309–16 (1992), to encapsulate drugs. The disclosures in these publications are fully incorporated herein by reference.

Table XIV below gives the recipes and results for these inverse emulsifications using calcium chloride as the crosslinking agent. Typically, 50.0 g aqueous solution containing 2.25 g dissolved sodium alginate and 0.25 g METHOCEL K4M (5% w/w sodium alginate/METHOCEL K4M) was dispersed in 75.0 g isooctane containing 1.5 g SPAN 85 in different reaction flasks and stirred at 1000 rpm for 10 minutes. Then, 5.0 g aqueous solution containing 1.0 g TWEEN 85 was added, and the dispersion was stirred for another 5 minutes. 25 g 8% w/w calcium chloride solution was added and allowed to react with the dispersed polymer droplets for 60 minutes. The microspheres were then dehydrated using the method developed by Ismail et al. (N. Ismail, M. S. Harris, and J. R. Nixon), J. Microencapsulation 1(1), 9–19 (1984), the entire disclosure of which is incorporated herein by reference, to dehydrate gelatin-acacia microcapsules, i.e, by stirring for 10 minutes in 25 ml isopropanol, filtering, washing twice by stirring overnight in a beaker with 200 ml isopropanol, filtering again, and drying at room temperature over night.

TABLE XIV

Sodium Alginate Microspheres Crosslinked Using Calcium Chloride

| Run No. | W-04 | W-06 | W-07 | W-10 |
|---|---|---|---|---|
| Water phase (g) | | | | |
| Sodium alginate | 4.50 | 9.00 | 9.00 | 2.25 |
| Methocel K4M | 0.50 | 1.00 | 1.00 | 0.25 |
| Water | 100.0 | 200.0 | 200.0 | 50.0 |
| Oil phase (g) | | | | |
| Isooctane | 150.0 | 300.0 | 300.0 | 75.0 |
| Span 85 | 3.0 | 6.0 | 6.0 | 1.5 |
| Emulsifier (g) | | | | |
| Tween 85 | 2.0 | 4.0 | 4.0 | 1.0 |
| Water | 10.0 | 20.0 | 20.0 | 5.0 |
| Crosslinking Agent | | | | |
| 8% aq. CaCl$_2$ (ml) | 50.0 | 100.0 | 100.0 | 25.0 |
| Addition Time (min) | 10 | 20 | 20 | 60 |
| Dehydrating Agent (ml) | | | | |
| Isopropanol | 50.0 | 100.0 | 100.0 | 25.0 |
| Reaction Flask | A | B | B | C |
| Reaction Time (min) | 35 | 45 | 45 | 90 |
| Microsphere Size (%) | | | | |
| a. >250 um | 30.5 | 6.2 | 11.2 | 5.60 |
| b. 250–212 um | 3.3 | 0.72 | 2.2 | 0.0 |
| c. 212–150 um | 29.0 | 1.7 | 5.4 | 0.0 |
| d. <150 um | 34.0 | 91.4 | 81.4 | 91.7 |

The results of these experiments show that the first run in reaction flask A gave a broad distribution of microsphere sizes. Only about one-third of the particles were smaller than 150 micrometers in diameter.

The runs in reaction flasks B and C gave a narrower size distribution and a large proportion of microspheres smaller than 150 micrometers in diameter. Thus, most of the microspheres crosslinked with calcium chloride were smaller than 150 micrometers in diameter.

The size, shape, and surface characteristics of these microspheres were markedly affected by the stirring speed, rate of addition of calcium chloride solution, and shape of the reaction flask and mixer. A 20- or 60-minute addition time for the aqueous calcium chloride solution, generally, gave microspheres that were smaller than 150 micrometers in diameter.

The use of reaction flask A (round-bottom flask with a Teflon polytetrafluroethylene half-moon stirrer blade) and a shorter addition time, gave fewer microspheres smaller than 150 micrometers in diameter and more microspheres of a diameter larger than 250 micrometers. Reaction flasks B and C both gave about 90% of the microspheres smaller than 150 micrometer in diameter, and for this reason are preferred over reaction flask A. Thus, the use of calcium chloride as the crosslinking agent resulted in the production of microspheres with a particle size smaller than 150 micrometers in diameter and a narrow size distribution, according to the stirring rate.

By way of comparison, most of the microspheres crosslinked with the XAMA-7 crosslinking agent and prepared in reaction flask C were also smaller than 150 micrometers in diameter. The size, shape, and surface characteristics of these microspheres were also markedly affected by the stirring speed, and the shape of the reaction flask and stirrer. Thus, it can be seen that the results for calcium ion as the crosslinking agent are roughly parallel to those of the XAMA-7 crosslinking agent. The addition of the calcium ion, however, is different from the addition of the XAMA-7 crosslinking agent which, for the best results, requires the variation of pH from pH 11 before and during emulsification to pH 7–8 after emulsification to achieve the desired particle size.

EXAMPLE 15

Capacity Of The Microspheres to Pass Through a 20- or 22-Gauge Syringe

In this experiment, the capacity of the microspheres to pass through a 20- or 22-gauge syringe was determined. Generally, dried microspheres were dispersed in water and allowed to swell.

Then, the aqueous dispersion was loaded into a hypodermic syringe and was forced out through the needle. Aqueous dispersions with low sodium alginate/XAMA-7 ratios could not be extruded, whereas those with higher sodium alginate/XAMA-7 ratios gave dispersions that could be extruded into worm-like threads. It is generally desirable for the aqueous dispersion of microspheres to be extrudable through a syringe to form a long worm-like thread.

EXAMPLE 16

Size Distribution of Sodium Alginate Microspheres with Varying Concentration of Emulsifier and pH During Crosslinking Step In this example, the sodium alginate/toluene/SPAN 60 emulsification system was used to show the effect of pH on the variation of the rate of crosslinking, whereby to control the emulsification. If the crosslinking is too rapid, the emulsification might not give a small enough droplet size before the viscosity of the aqueous phase increases to a value too great for dispersion.

Therefore, the emulsifications were carried out at a relatively high pH, such as pH 11; then, after the emulsion had been formed, the pH was lowered to 7. This approach allows ample time for the emulsification to be accomplished, yet provides rapid crosslinking once a desirable emulsion has been formed.

Table XV below gives the recipes for these experiments and the results obtained:

TABLE XV

| | Sodium Alginate Microspheres Using XAMA-7 and SPAN 60 | | | | | | |
|---|---|---|---|---|---|---|---|
| Run No. | S-35 | S-36 | S-37 | S-38 | S-39* | S-40 | S-42 |
| Water Phase (g) | | | | | | | |
| Sodium alginate | 7.0 | 7.0 | 7.0 | 7.0 | 7.0 | 7.0 | 7.0 |
| Water | 100 | 100 | 100 | 100 | 100 | 100 | 100 |
| Oil phase (g) | | | | | | | |
| Toluene | 100 | 100 | 100 | 100 | 100 | 100 | 100 |
| SPAN 60 | 1.5 | 1.0 | 1.0 | 1.0 | 1.0 | 2.0 | 2.0 |
| pH (using NH4OH) | 6.6 | 10.0 | 9.0 | 9.0 | 9.0 | 9.0 | 6.4 |
| XAMA-7 (g) | 4.0 | 4.0 | 4.0 | 4.0 | 4.0 | 4.0 | 4.0 |
| pH (using aq. HCl) | — | 7.0 | — | — | — | — | — |
| Reaction flask | C | C | C | C | C | C | C |
| Reaction time (hr) | 5.0 | 4.0 | 3.0 | 4.5 | 4.5* | 4.0 | 4.5 |
| Stirring rate (rpm) | 1100 | 1100 | 1300 | 1000–1300 | 1000 | 1200 | 1300–1500 |
| Dehydrating agent (ml) | | | | | | | |
| Isopropanol | 100 | 100 | 100 | 100 | 100 | 100 | 100 |
| Microsphere size (%) | | | | | | | |
| a. >250 um | 14.4 | 27.4 | 0.83 | 4.89 | 1.87 | 4.28 | — |
| b. 212–250 um | 7.4 | 10.1 | 2.00 | 1.99 | 1.74 | 12.6 | — |
| c. 150–212 um | 21.7 | 22.7 | 14.5 | 8.69 | 36.1 | 15.0 | — |
| d. <150 um | 56.5 | 39.9 | 81.4 | 84.5 | 60.3 | 66.8 | — |

*20 g 8% calcium chloride after 2 hr reaction

In Run S-36, 37% of the microspheres formed were larger than 212 micrometers and 40% were smaller than 150 micrometers. A higher percentage of microspheres smaller than 150 micrometers is desired; however, the microspheres of this sample were aggregated. In this case, the original pH of 10 was lowered by addition of hydrochloric acid. A white precipitate was formed, which was attributed to the precipitation of alginic acid by the hydrochloric acid.

In Run S-37, the pH of the 7.0% aqueous alginate solution was adjusted from 6.6 to 9.0 with ammonium hydroxide. Similarly, the pH of Runs S-38 and S-40 was adjusted to 9.0. In Run S-40, the toluene and SPAN 60 concentrations were increased to s enhance the emulsification; however, this higher concentration of the oil phase also resulted in aggregation.

By way of comparison, at a lower concentration, i.e., 5% sodium alginate; at pH 7, a gelation time of one hour is possible. (See Run No. 5-7-1, Table VI).

EXAMPLE 17

Preparation of Crosslinked Sodium Alginate Particles in Oil Phase Comprising Isooctane and Emulsifier Mixture As the XAMA-7 crosslinking agent proved to be somewhat soluble in toluene, it was decided not to use the toluene/SPAN 60 system in further experiments. Therefore, another system using isooctane as the organic phase and a SPAN 85/TWEEN 85 emulsifier mixture was substituted. Table XVI gives the recipes and results for these experiments.

TABLE XVI

Sodium Alginate Microspheres Using XAMA-7/Isooctane/SPAN 85

| Run No. | W-20 | W-21 | W-23 | W-30 |
|---|---|---|---|---|
| Water phase (g) | | | | |
| Sodium alginate | 2.25 | 2.25 | 4.50 | 4.50 |
| METHOCEL K4M | 0.25 | 0.25 | 0.50 | 0.50 |
| Water | 50 | 50 | 50 | 100 |
| Oil phase (g) | | | | |
| Isooctane | 75 | 75 | 150 | 150 |
| SPAN 85 | 1.5 | 1.5 | 3.0 | 3.0 |
| Emulsifier (g) | | | | |
| TWEEN 85 | 1.0 | 1.0 | 1.0 | 2.0 |
| Water | 5.0 | 7.0 | 7.0 | 1.0 |
| Crosslinking agent (g) | | | | |
| XAMA-7 | — | 1.5 | 5.0 | — |
| 8% CaCl2 soln | 25 | 10 | — | 50 |
| Reaction flask | C | C | C | E |
| Reaction time (hr) | 4.5 | 4.5 | 4.5 | 3.0 |
| Stirring rate (rpm) | 2000–2500 | 1100–1500 | 1000–1500 | 1000 |
| Dehydrating agent (ml) | | | | |
| Isopropanol | 25 | 25 | 70 | 100 |
| Microsphere size (%) | | | | |
| a. >250 um | 0 | 10.3 | — | 0 |
| b. 212–250 um | 0 | 3.0 | — | 2.5 |
| c. 150–212 um | 0 | 9.4 | — | 5.0 |
| d. <150 um | 100 | 77.3 | — | 92.5 |

As seen from Table XVI, Run W-23 gives a typical result of these experiments. The droplet sizes were checked by optical microscopy at each step. Droplets of the desired size (smaller than 150 micrometers) were observed in all steps up to the addition of isopropanol, which was intended to stop the crosslinking reaction. This addition increased the viscosity to the point where it became difficult to stir the reaction mixture after about 20 minutes, at which point the sample appeared to be coagulated. When diluted with water, the sample showed the presence of microspheres.

Table XVI shows the results of using a crosslinking agent comprising a mixture of calcium chloride/XAMA-7. Run W-21 demonstrates that such a mixed crosslinking agent results in 77% of the microspheres being smaller than 150 micrometers. However, many of the microspheres were nonspherical and elongated in shape.

In contrast, the higher stirring rate of Run W-20, along with the use of calcium chloride as the sole crosslinking agent, gave 100% microspheres smaller than 150 micrometers. Nevertheless, there was some aggregation.

Generally, as can be concluded from Runs W-20 and W-21, the size, shape, and size distribution of the microspheres were determined by the stirring rate and the design of the reaction flask and stirrer, as well as the dispersing agent. In these two Runs, as well as in Run W-23, the stirring rate varied throughout the experiments because the motor was unable to maintain a constant speed, when the load varied during the emulsification and crosslinking. This variation is reflected in the range of stirring rates shown in Table XVI for Runs W-20, W-21, and W-22.

This experiment was repeated using a constant-rate electric stirrer. The results are shown in Run W-30 in Table XVI. As can be seen from Run W-30, when the stirring rate remained constant, independent of the load, microspheres of crosslinked sodium alginate/METHOCEL K4M, predominately had a diameter of less than 150 micrometers when using calcium ion as the crosslinking agent, with isooctane as the continuous phase, and TWEEN 85 as the emulsifying agent.

EXAMPLE 18

Comparison of Microspheres of Sodium Alginate Crosslinked with Calcium Ion and XAMA-7

The main difference between the calcium ion and XAMA-7 cross-linking agent is that the calcium ions form ionic bonds, whereas the XAMA-7 crosslinking agent forms covalent bonds. Ionic bonds are influenced by the electrolyte in the surrounding medium and may dissolve if the composition of the medium changes sufficiently. In contrast, covalent bonds are unlikely to be affected by changes in the medium. Therefore, experiments were carried out to determine the relative stability of microspheres crosslinked with ionic and covalent bonds. Table XVII gives the results of these experiments.

TABLE XVII

Comparison of CaCl$_2$ Ionic and XAMA-7 Covalent Bonds

| Run No. | A | B | A-1 | A-2 |
|---|---|---|---|---|
| Crosslinking Agent | CaCl$_2$ | XAMA-7 | CaCl$_2$ | CaCl$_2$ |
| Preparation Run | W-30d | S-58d | W-30d | W-30d |
| Microspheres (g) | 0.15 | 0.15 | 0.15 | 0.15 |
| 5% EDTA soln. (g) | 5.0 | 5.0 | 5.0 | — |
| 2% Saline soln. (g) | 5.0 | 5.0 | — | 5.0 |
| 18 hrs room temp.; no stirring | some disintegration | no disintegration | no disintegration | no disintegration |
| additional 18 hrs. room temp.; with stirring | beads almost disintegrated to viscous liquid | no disintegration | beads almost disintegrated to viscous liquid | no disintegration |

Preparation Runs W-30d and S-58d refer to the fraction of microspheres of Runs W-30 and S-58 that were smaller than 150 micrometers Microspheres crosslinked with calcium chloride (Runs W-30d) and XAMA-7 (Run S-58d) were placed in 5% ethylenediamineacetic acid (EDTA) and 2% aqueous saline (NaCl) solution and allowed to stand for 18 hours without stirring. The microspheres crosslinked with calcium chloride had begun to disintegrate, whereas those crosslinked with XAMA-7 remained stable without distortion.

After an additional 18 hours at room temperature with stirring, the microspheres crosslinked with calcium chloride continued to disintegrate, whereas those crosslinked with XAMA-7 remained integral without distortion.

In separate experiments using the EDTA solution and saline solution alone, the microspheres crosslinked with calcium chloride disintegrated in the EDTA solution, but not in the saline solution. Thus, it is the complexing of the calcium ions by the EDTA that results in the breaking of the crosslinks and the dissolution of the microspheres. The saline solution had no such effect.

In contrast, the microspheres crosslinked with XAMA-7 showed no disintegration in EDTA solution or saline solution under the same conditions. These results demonstrate that the covalent bonds resulting from the XAMA-7 crosslinking agent were more stable than the ionic bonds resulting from the calcium chloride crosslinking.

EXAMPLE 19

Preparation of Aqueous Dispersions of Protein Particles Crosslinked with Glutaraldehyde In this example, aqueous dispersions of crosslinked particles of bovine serum albumin were prepared.

1.0 g bovine serum albumin was dissolved in 0.1 M sodium acetate buffer (pH 7.8) and 0.5 g glutaraldehyde was added to determine if the bovine serum would be crosslinked by the crosslinking agent; the crosslinking action occurred immediately upon addition of the glutaraldehyde.

Then, 1.0 g bovine serum albumin was dissolved in 8 g buffer solution, and 2.0 g 25% glutaraldehyde was added after emulsification in 20.0 g o-xylene containing 5% PLURONIC L92, a commercially available non-ionic propylene oxide/ethylene oxide block copolymer emulsifier from BASF, having an HLB of 1.0–7.0. The crosslinking agent was allowed to react with the emulsified bovine serum albumin droplets for four hours at room temperature. The emulsion was then inverted in 400 ml water containing 0.5% AEROSOL A-102 wetting agent (disodium ethoxylated alcohol half-ester of sulfosuccinic acid) available from American Cyanamid Co.

EXAMPLE 20

Preparation of Water-In-Oil Dispersion of Crosslinked Particles of Bovine Serum Albumin In this example, 3.0 g bovine serum albumin in 15.0 g buffer solution (sodium acetate pH 7.8) was emulsified in 60 g o-xylene containing 5% TETRONIC 1102, a commercially available (BASF) water-in-oil emulsifier, HLB 6.5, which comprises ethylenediamine tetrasubstituted with propylene oxide/ethylene oxide block copolymers with 20 moles propylene oxide and 10 moles ethylene oxide. This emulsion was then ultrasonified with a Branson Ultrasonifier (50% duty cycle; setting 7; 1 min.). Afterwards, 6.0 g 25% aqueous gluraraldehyde solution was added to crosslink the bovine serum albumin droplets in the water-in-oil-dispersion.

The result was a dispersion of submicroscopic crosslinked bovine serum albumin particles dispersed in the continuous o-xylene phase.

EXAMPLE 21

Preparation of Aqueous Dispersion of Crosslinked Particles of Bovine Serum Albumin 6 g bovine serum albumin in 15 g buffer (sodium acetate pH 7.8) was emulsified in 60 g o-xylene containing PLURONIC L92 emulsifier and crosslinked with 8 g 25% aqueous glutaraldehye solution added after emulsification. This water-in-oil dispersion of crosslinked bovine serum albumin particles was then inverted in 400 ml water containing 0.5% TRITON X-405, a commercially available octylphenoxy polyethoxy ethanol surfactant (Union Carbide; HLB 17.9)

The result of the inversion was a dispersion of crosslinked bovine serum albumin particles dispersed in water. The o-xylene continuous phase and water phase were immiscible and were easily separated from one another. Afterwards, the colloidal stability of the particle dispersion in water was tested, as described below.

The aqueous dispersion of crosslinked particles of bovine serum albumin was washed with buffer and then centrifuged twice, in a conventional Sorvall laboratory centrifuge. Afterwards the aqueous dispersion was tested for stability in aqueous sodium chloride solution. The dispersion showed good stability in 0.15 M sodium chloride, formed only a little coagulum in 0.30 M solution, more coagulum in 0.60 M solution and flocculated in 0.90 M solution. These results indicate that the bovine serum albumin dispersion is a lyophilic colloid rather than a lyophobic colloid, which generally have critical coagulation concentrations of about 0.1 M for monovalent cations. Transmission microscopy showed that the crosslinked particle size is from about 5 to about 8 micrometers.

EXAMPLE 22

Effect of Crosslinking Concentration in the Formation of Aqueous Dispersions of Bovine Serum Albumin Particles The effect of crosslinking concentration in the reparation of aqueous dispersions of crosslinked bovine serum albumin particles was determined by varying the glutaraldehyde concentration.

10 g 20% bovine serum albumin was emulsified in 30 g o-xylene containing approximately 5% TETRONIC 1102. The emulsion was ultrasonified (setting 5; 90 sec), and the glutaraldehyde was added to a concentration of 5, 10, 15, or 20% weight/weight, based on the bovine serum albumin. The crosslinking agent in each of the emulsions was then allowed to react for 12 hours at room temperature. Then, the emulsions were each inverted in 200 ml water containing 1% TRITON X-405 The o-xylene was removed by distillation of the o-xylene/water azeotrope. The dispersions were then each cleaned by serum replacement with water containing 50 ppm formaldehyde (to prevent bacterial growth) and examined by transmission electron microscopy. In serum replacement, the dispersion or latex is confined in a cell with a semipermeable membrane, and pure water (or a solution) is pumped through the cell to literally replace the serum with the water (or solution). The net effect is to remove any dissolved material in the aqueous phase, as well as any surfactant adsorbed on the particles. Nuclepore membranes, which have a remarkably uniform submicroscopic pore size are used. The resolution of separation is good enough to remove the adsorbed and solute surfactant quantitatively. Each of the dispersions comprised discrete polymer particles dispersed in water.

EXAMPLE 23

Preparation of Aqueous Dispersions of Crosslinked Particles of Human Gamma-Globulin In this example, three experiments were conducted to obtain aqueous dispersions of crosslinked human gamma-globulin particles. First, the rate of crosslinking of human gamma-globulin was determined. 1 g human gamma-globulin was dissolved in 10.5 g water, and this solution was then mixed with 6% and 12% aqueous glutaraldehyde solutions by weight, based on the weight of gamma globulin. Crosslinking occurred within 30 seconds after the addition of the crosslinking agent.

Then, 1 g human gamma-globulin in 10 g water was emulsified in 30 g o-xylene containing 1.5 g TETRONIC 1102. This water-in-oil dispersion of droplets of human gamma-globulin was then mixed with 0.24 g of 25% glutaraldehyde solution. This dispersion, when inverted in 400 ml water containing 0.5% AEROSOL A-102, coagulated.

7.8 g 10% aqueous human gamma-globulin solution was emulsified in 15 g o-xylene containing 0.75 g TETRONIC 1102. This emulsion was then ultrasonified as before and 0.17 g of 25% glutaraldehyde was added. The emulsion was then inverted in 150 g water containing 0.75 g AEROSOL A-102.

20 g 10% human gamma-globulin aqueous solution was emulsified in 60 g o-xylene containing 3 g TETRONIC 1102, after which the emulsion was ultrasonified, as earlier disclosed. During this time 0.8 g of glutaraldehyde (25% aqueous solution) was added to crosslink the human gamma-globulin droplets formed by the emulsion. The emulsion was then inverted in 400 ml water containing 2 g AEROSOL A-102.

Each of the above three dispersions, when examined under electron microscopy or optical microscopy, comprised crosslinked human gamma-globulin polymer particles in an aqueous dispersion.

EXAMPLE 24

Preparation of Crosslinked Particles of Human Gamma-Globulin In Aqueous Dispersion In this experiment, 1 g human gamma-globulin was dissolved in 9 g water and then emulsified in 30 g o-xylene containing 1.5 g TETRONIC 1102. The emulsion was ultrasonified, as before described, i.e., setting 5; 1 min. Then, 0.6 g of 15% glutaraldehye solution was added, and the sample was tumbled end-over-end for 12 hours at room temperature in a capped bottle. The emulsion was then inverted in 300 ml water containing 3 g TRITON X-405. The o-xylene was then stripped at temperatures below 20° C. to prevent aggregation of the particles. The aqueous dispersion, when cleaned by serum replacement in conventional manner, contained aggregates of the human gamma-globulin particles, which was attributed to the low pH. In any event, after serum replacement, the particles were seen to be aggregated.

In view of the above, the experiment was repeated except that the concentration of glutaraldehye was doubled and the pH was adjusted to 7 by addition of sodium bicarbonate buffer. The dispersion was then inverted and cleaned by serum replacement with 0.1 M sodium acetate buffer (pH 7.8) at temperatures below 35° C. to prevent aggregation. The result was that the particles were not aggregated.

Human gamma-globulin (2.5%) aqueous dispersions were also prepared in borate buffer (pH 8.–8.7). Only part of the human gamma-globulin was soluble in the borate buffer at 2.5% concentration.

1 g human gamma-globulin in 9 g buffer (pH 8.4) was emulsified in 30 g o-xylene containing 1.5 g TETRONIC 1102. The emulsion was ultrasonified as before (setting 3:30 sec), and 1.0 g of 25% aqueous glutaraldehyde added. The crosslinking reaction was carried out for 19 hours at room temperature. The dispersion was then inverted in an excess of 1% TRITON X-405 solution and agitated for 3 hours. The o-xylene was then stripped under vacuum and the dispersion was cleaned by serum replacement with borate buffer (pH 8.4). As will be appreciated by those skilled in the art, significant dilution is necessary for distillation of the o-xylene/water azeotrope from the dispersion.

The human gamma-globulin particles were also crosslinked by using 1-ethyl-3-(3-dimethylaminopropyl) carbodiimide-hydrochloride (ECDI). 1.0 g 2% human gamma-globulin aqueous solution was mixed with 0.03, 0.10, 0.50, and 1.0% ECDI crosslinking agent, and with glutaraldehyde (25% aqueous solution) for comparison. A visible precipitate formed in each case, although the precipitate was somewhat difficult to see in the low concentration.

Other TETRONIC water-in-oil emulsifiers, commercially available from BASF, such as TETRONIC 90R4 (HLB 7.1), 110R2 (HLB 3.5),and 150R4 (HLB 5.4), were also tried. These emulsifiers all have low HLB values and are believed to be block copolymers of propylene oxide/ethylene oxide of varying proportions, similar in structure to TETRONIC 1102. These emulsifiers, however, were found not to be as effective in these emulsions as TETRONIC 1102. The TETRONIC 90R4 was found, moreover, not to be soluble in o-xylene.

EXAMPLE 25

Preparation of Aqueous Dispersion of Human Gamma-Globulin Particles Using Phosphate Buffer Saline as Medium for Emulsification Phosphate buffered saline (pH 6.95) was tried as the medium for the emulsification of human gamma-globulin. In this case, 2.5% human gamma-globulin was soluble in this buffer. 10 g of 2.5% human gamma-globulin in phosphate buffered saline was emulsified in 30 g o-xylene containing 5% TETRONIC 1102. The emulsion was ultrasonified as before and mixed with 0.0125 g of ECDI crosslinking agent. The mixture was agitated for 4 days; after which the emulsion was inverted in 400 g phosphate buffer saline containing 0.5% TRIRTON X-405 and the o-xylene stripped, to give an aqueous dispersion of crosslinked human gamma-globulin particles.

EXAMPLE 26

Preparation of Aqueous Dispersions of Human Gamma-Globulin Using Various Concentrations of Human Gamma-Globulin and Crosslinking Agent ECDI Other latexes were prepared using 10 g 3.5% human gamma-globulin in 30 g o-xylene containing 5% TETRONIC 1102 and 0.035 g ECDI; 3 g 10% human gamma-globulin with 0.035 g ECDI in 10 g o-xylene containing 5% TETRONIC 1102; and 3 g 10% human gamma-globulin in 10 g o-xylene containing 5% TETRONIC 1102 with 0.06 g ECDI.

All of these latexes gave aqueous dispersions of crosslinked human gamma-globulin particles.

EXAMPLE 27

Distribution of Particle Sizes of Crosslinked Microspheres Prepared from Various Water-Soluble Polymers In this example, crosslinked hydrophilic particles were prepared from hydroxyethyl cellulose, poly(vinyl alcohol), chondroitrin sulfate, and other water-soluble polymers. Table XVIII gives the results for hydroxyethyl cellulose.

TABLE XVIII

Crosslinking of Hydroxyethyl Cellulose with XAMA-7

| Run No. | HOC-01 | -02 | -03 | -04 |
|---|---|---|---|---|
| Water Phase (g) | | | | |
| HOC | 7.0 | 7.0 | 7.0 | 7.0 |
| Water | 100 | 100 | 100 | 100 |
| pH | 7–8 | 7–8 | 7–8 | 10–11 |
| Oil phase (g) | | | | |
| Span 60 | 1.0 | 1.0 | 1.0 | 1.0 |
| Toluene | 100 | 100 | 100 | 100 |
| XAMA-7 (g) | 4.0 | 4.0 | 4.0 | 4.0 |
| Dehydrating agent (ml) | | | | |
| Methanol | 100 | — | — | — |
| Isopropanol | — | 100 | 100 | 100 |
| Reaction flask | C | C | C | C |
| Stirring rate (rpm) | 1000 | 1000 | 1000 | 1000 |
| Reaction time (hr) | 19 | 14 | 18 | 22 |
| Microspheres (%) | | | | |
| a. >250 um | — | 7.5 | 19.5 | — |
| b. 212–250 um | — | 2.3 | 5.9 | — |
| c. 150–212 um | — | 1.8 | 29.7 | — |
| d. <150 um | — | 88.7 | 45.0 | — |

HOC — hydroxyethyl cellulose

The hydroxyethyl cellulose was dissolved in the water, and the pH of the solution was adjusted to 7–8. The SPAN 60 was dissolved in the toluene, and the solution was used as the continuous phase for the emulsification of the aqueous hydroxyethyl cellulose solution. The emulsification was carried out until the emulsion droplets were judged satisfactory, i.e. the droplets were seen to be discrete and spherical, and not irregular in shape, with a preponderance of the sizes smaller than 150 micrometers diameter, as monitored by optical microscopy. At pH 7, the crosslinking reaction (XAMA-7) occurred rapidly at room temperature.

In Run H0C-01, the beads aggregated upon addition of the methanol, to dehydrate the crosslinked particles formed. Therefore, in the remaining experiments shown in Table XVIII, isopropanol was used as the dehydrating agent. This resulted in the formation of microspheres of the stated size ranges. Generally, however, the microspheres were not as perfect as those made from sodium alginate.

EXAMPLE 28

Experiments Showing the Effect of Heat with and Without a Catalyst Combined with the Crosslinking Agent on the Preparation of Crosslinked Water-Soluble Particles In these experiments, other water-soluble polymers were investigated, along with determining the effect of heat and a catalyst with the crosslinking agent. The results are shown in Table XIX below. In general, the procedure was: a) the dissolution of the water-soluble polymer in water, along with the crosslinking agent; b) emulsification of this solution in a continuous oil phase containing a water-in-oil emulsifier; c) homogenization of the emulsion by stirring, ultrasonification, or homogenization; d). heating of the emulsion to effect crosslinking; e). and inversion of the emulsion into water to transfer the crosslinked particles to the aqueous phase.

TABLE XIX

Crosslinking of Water-Soluble Polymers

| Run. No. | 101 | 102 | 103 | 105 | 106 | 107 | 108 | 109 | 110 | 111 | 112 | 113 | 114 | 115 | 116 | 117 |
|---|---|---|---|---|---|---|---|---|---|---|---|---|---|---|---|---|
| Polymer | PVP | PVP | PVP | PVA | PVA | MC | PVA | PVA | MC | PVA | PVA | MC | PVA | PVA | PVA | PVA |
| Weight (g) | 1.0 | 1.0 | 2.0 | 2.3 | 6.0 | 3.0 | 6.0 | 3.0 | 2.0 | 5.0 | 5.0 | 2.0 | 2.0 | 0.8 | 3.0 | 6.0 |
| Water (g) | 19.0 | 19.0 | 18.0 | 20.2 | 27.0 | 36.0 | 25.5 | 33.0 | 31.5 | 15.0 | 15.0 | 29.5 | 21.0 | 8.7 | 29.3 | 57.0 |
| Glutaraldehyde | — | — | — | 2.5 | 7.0 | 3.0 | 7.0 | 3.8 | 4.5 | 1.0 | 1.0 | 2.5 | 0.5 | 0.5 | 0.5 | 1.0 |
| o-Xylene (g) | 20.0 | 20.0 | 40.0 | 22.5 | 40.0 | 40.0 | 43.2 | 18.0 | 18.0 | 97.2 | 45.0 | 153.0 | 52.3 | 19.0 | 57.0 | 97.0 |
| Span 60 (g) | 1.0 | 0.2 | 1.0 | — | — | — | | | | | | | | | | |
| Tetronic 1102 | — | — | — | 2.5 | 4.0 | 4.0 | 4.8 | 2.0 | 2.0 | 10.8 | 5.0 | 17.0 | 0.25 | — | 3.0** | — |
| Pluronic L92 | | | | | | | | | — | — | — | — | 2.5 | — | — | 3.0 |
| Aerosol OT | | | | | | | | | — | — | — | — | — | 1.0* | — | — |
| p-Toluene (g) sulfonic acid | 1.0* | 1.0* | 2.0* | — | 1.0 | 1.0 | 0.5 | 0.3 | 0.25 | 0.25 | 0.8 | 1.0 | 0.1 | 0.05 | 0.2 | 0.3 |
| Inverting emulsifiers | — | — | — | — | — | — | X-405 | X-405 | X-405 SLS | SLS — | SLS — | SLS — | — | — | X-305 A-102 SLS | X-305 A-102 — |

*ammonium persulfate
X-405 - Triton X-405
PVP - poly (N-vinyl pyrrolidone); MW 360,000
PVA - Vinol 125 poly(vinyl alcohol); MW 70,000; 99.6% hydrolyzed
MC - Methocel K4M hydroxypropylmethyl cellulose
*also Tetronic 702 and 1102; Pluronic L92
**also Tetronic 702, 70R2, 50R4; Pluronic L92; Span 60; AerosolOT
The ammonium persulfate in the presence of p-toluene sulfonic acid was used as a crosslinking agent to crosslink the PVP.

In Run 101, a 5% aqueous solution of poly(N-vinyl pyrrolidone), containing the stated amount of ammonium persulfate as the crosslinking agent was emulsified in o-xylene. The emulsion was ultrasonified (Branson Ultrasonifier; 50% duty cycle setting; room temperature) and then heated for 30 minutes at 80° C. Upon inversion in water containing TRITON X-305 (octylphenoxypolyethoxy ethanol, HLB 17.3, Union Carbide), the presence of particles was demonstrated by optical microscopy and scanning electron microscopy, according to usual techniques.

Run 102 by comparison used a 5% aqueous solution of the PVP and ammonium persulfate as the crosslinking agent with, however, a 1% SPAN 60 solution being used rather than the 5% of Run 101. The emulsion was ultrasonified (50% duty cycle; setting 3; 1 min.) and heated for 30 min. at 80° C. The result was a very viscous emulsion that could not be inverted. The viscous emulsion was believed to be due to the lower concentration of SPAN 60.

Run 103 used a larger batch size and an intermediate concentration of SPAN 60, i.e., 2.5%. The emulsion was hand-homogenized (two cycles) to reduce the droplet size to about 4 micrometers, stirred at 236 rpm using a conventional laboratory stirrer and heated at 80° C. for 30 minutes. When inverted in water, the emulsion separated into two layers, the lower of which appeared to be a gel of the 4 micrometer diameter crosslinked particles.

In Run 105, an aqueous solution of poly(vinyl alcohol) was prepared and emulsified in o-xylene containing TETRONIC 1102 emulsifier. This emulsion was mixed with the glutaraldehyde crosslinking agent. This system failed to react after 1.5 hours at 70° C. When 1.0 g p-toluene sulfonic acid in 11.0 g water was added, however, to 6.0 g PVA dissolved in 28 g of 28% glutaraldehyde, a rapid reaction occurred when the mixture was heated to 40° C. Similar experiments using methylcellulose (instead of the PVA) with glutaraldehyde crosslinking agent, and p-toluene sulfonic acid and hydrochloric acid catalysts, gave a brown color but no discernible particles. Run 106 used PVA as the water-soluble polymer and glutaraldehyde as the crosslinking agent, with p-toluene sulfonic acid as a catalyst.

Run 107 used methyl cellulose (Dow METHOCEL K4M) as the water-soluble polymer and glutaraldehyde as the crosslinking agent, catalyzed with p-toluene sulfonic acid. The reaction was conducted at room temperature. Water was removed from the emulsion by distillation of the o-xylene/water azeotrope, and an additional 61 g o-xylene was added to the emulsion. This resulted in some flocculation. The emulsion was then inverted in water to form a dispersion of crosslinked methyl cellulose particles in water.

Run 108 used PVA as the water-soluble polymer and the same crosslinking agent and catalyst as in Run 107, the later being added to the aqueous solution prior to emulsification. The PVA crosslinked within 4 minutes after addition of the catalyst. The final particles were soft, and stuck to each other and the metal sphere for grinding. The emulsion was inverted in 500 ml aqueous TRITON X-405, and 26 ml o-xylene was removed by distillation. Some flocculation of the particles occurred.

Run 109 used PVA and the same crosslinking agent and catalyst as in Run 108. The glutaraldehyde and the p-toluene sulfonic acid were mixed together, and the solution was emulsified immediately thereafter. Therefore, the crosslinking reaction was somewhat competitive with the emulsification, and some crosslinking would have been expected along with the emulsification. A magnetic stirring rod was used to mix the sample. Although a magnetic stirring rod was effective in making the emulsion, those skilled in the art will readily appreciate that such is not capable of fine variation. The crosslinking reaction took place within 10 minutes. An additional 40 g o-xylene was added, while the o-xylene/water azeotrope was being distilled off the emulsion. The final emulsion was inverted in 300 ml 10% aqueous TRITON X-405 emulsifier and 500 ml 1% aqueous sodium lauryl sulfate, a high-HLB emulsifier, used to invert the water-in-oil emulsion. The emulsion inverted but with some flocculation of the crosslinked particles.

In Run 110, methyl cellulose was used as the water-soluble polymer. The crosslinking agent was glutaraldehyde and p-toluene sulfonic acid was used as a catalyst, these being added to the aqueous solution prior to emulsification. The polymer solution was emulsified in the oil phase immediately after addition of the glutaraldehyde and p-toluene sulfonic acid. This very viscous, i.e., hard to pour, solution was dispersed in the o-xylene using a conventional hand-homogenizer.

Crosslinking was judged complete within 2 hours at room temperature after addition of the catalyst and crosslinking agent. The emulsion was inverted in an aqueous solution comprising 200 ml 15% aqueous TRITON X-405 solution and 200 ml 1% aqueous sodium lauryl sulfate solution. Flocculation occurred during this inversion. No particles were seen by scanning electron microscopy.

Run 111 used PVA as the water-soluble polymer and the same crosslinking agent and catalyst as in the previous run. The crosslinking agent and catalyst were added before the emulsification and mixed by ultrasonification. When 30 ml of the water-in-oil emulsion were inverted in 270 ml 1% aqueous sodium lauryl sulfate solution, and the o-xylene/water azeotrope was removed by distillation, the resulting water-in-water emulsion showed no particles by scanning electron microscopy. By comparison, when 20 g of the water-in-oil emulsion was stirred with 1.0 g p-toluene sulfonic acid for 30 hours at room temperature no crosslinking occurred, this being shown by the lack of particle formation. Nevertheless, when the water-in-oil emulsion was heated to 50° C. crosslinking occurred, as was confirmed by the presence of particles.

Run 112 used 20 g 20% PVA and 16 g 25% glutaraldehyde with 4 g p-toluene sulfonic acid catalyst emulsified in 50 g o-xylene containing about 5 g TETRONIC 1102. This emulsion was heated at 40° C. When the catalyst was added before the emulsification, the water-soluble polymer solution became very viscous and could not be stirred. Nevertheless, when the catalyst was added after the emulsification, following the emulsion being rotated end-over-end in a capped bottle for 30 hours at room temperature, crosslinking occurred, as evidenced by the formation of beads. When the emulsion was inverted in 800 ml 1% aqueous sodium lauryl sulfate solution, it formed a precipitate, which was redispersed in the water with a hand-homogenizer.

Run 113 used 10 g 10% methyl cellulose solution and the stated amounts of crosslinking agent and catalyst as the water-soluble polymer solution. This solution was emulsified in an oil phase comprising o-xylene and 10% TETRONIC 1102 emulsifier. The emulsion was stripped according to usual techniques at 40° C. to remove the o-xylene/water azeotrope (25 g water and 55 g of the o-xylene). 30 g of this emulsion, inverted in 300 ml of a 1% sodium lauryl sulfate solution showed little sign of reaction. Another 100 g sample of the emulsion was inverted in 900 ml 0.5% sodium lauryl sulfate with similar results. This run was repeated using 20 g 10% methyl cellulose, 10 g 25% glutaraldehyde and 5 g 20% p-toluene sulfonic acid catalyst solution emulsified in 170 g o-xylene containing 10% TETRONIC 1102. The emulsion was homogenized twice in a conventional hand-homogenizer. The emulsion was still stable after 20 ml water was stripped. The crosslinking reaction was carried out by tumbling the emulsion in a capped bottle end-over-end for 24 hours at 40° C. The polymer precipitated, and the solution became clear, this occurring before inversion as in the previous part of this Run 113.

In Run 114, 20 g 10% poly(vinyl alcohol) (VINOL 124; MW 90M) solution, 2 g 25% glutaraldehyde, and 0.5 g 20% p-toluene sulfonic acid solution was emulsified in 50 g o-xylene containing 5% PLURONIC L92. Some coagulum was formed after 12 ml water and 28 ml o-xylene was stripped. The emulsification was also carried out in 50 g o-xylene containing 5% TETRONIC 1102. This emulsion flocculated after 18 g water was stripped and the emulsion was shaken in a conventional Red Devil Paint Shaker.

Run 115 used an aqueous water-soluble polymer solution (8 g 10% PVA), 2 g 25% glutaraldehye solution, and 0.2 g 25% p-toluene sulfonic acid solution emulsified in 20 g o-xylene containing 5% AEROSOL OT (the dioctyl ester of sodium sulfosuccinic acid), commercially available from American Cyanamid. In this Run, the emulsion was formed and then the catalyst was added. The polymer emulsion droplets were crosslinked within 30 minutes after the catalyst was added to the emulsion. The emulsion flocculated, however, after being shaken in a Red Devil Paint Shaker. Other emulsifications, carried out in o-xylene containing 5% TETRONIC 702 (BASF; HLB 1.0–7.0, believed to be a propylene oxide/ethylene oxide block copolymer) with the catalyst added after emulsification, also gave flocculation. TETRONIC 1102 gave a stable emulsion with only a little coagulum, which was inverted in 500 ml 0.5% sodium lauryl sulfate solution. PLURONIC L92 gave a stable emulsion with only a little coagulum, which was inverted in 300 ml 0.2% sodium lauryl sulfate solution, 300 ml 0.2% TRITON X-305 solution, or 200 ml 0.4% AEROSOL A-102 solution, without flocculation. On the other hand, AEROSOL OT gave a flocculation to form a mass of polymer.

In Run 116, 30 g 10% PVA aqueous solution, 2 g 25% glutaraldehyde aqueous solution, and 1 g 20% p-toluene sulfonic acid aqueous solution were emulsified in o-xylene (60 g) containing 6.0% TETRONIC 1102. The water was stripped from the emulsion, prior to the catalyst being added. Crosslinking of the polymer emulsion droplets was carried out by tumbling the emulsion in a capped bottle end-over-end for 12 hours at room temperature. The emulsion, when inverted in 800 ml 0.2% TRITON X-305 or AEROSOL A-102 solution, flocculated, but was redispersed by ultrasonification (Branson Ultrasonifier; room temperature). Other emulsifiers were compared using 8 g 10% PVA aqueous solution, 2 g 25% glutaraldehyde aqueous solution, and 0.2g (25%) p-toluene sulfonic acid aqueous solution, these solutions being emulsified in 20 g o-xylene containing 5% emulsifier. In each case, the first step was carrying out the emulsification using the hand-homogenizer. TETRONIC 1102 gave a very stable emulsion; TETRONIC 702 gave an emulsion that separated upon cessation of the agitation. PLURONIC L92 gave a very stable emulsion, as did AEROSOL OT. SPAN 60, TETRONIC 70R2 and TETRONIC 50R4 each gave emulsions that separated on cessation of the agitation.

The second step in these experiments was the crosslinking of the polymer emulsion droplets in the emulsion; p-toluene sulfonic acid was added after emulsification, and the capped bottles in which the emulsions were contained were tumbled end-over-end at room temperature for 12 hours. The TETRONIC 1102 emulsion remained stable; the TETRONIC 702 emulsion crosslinked to form a mass of the water-soluble polymer; the PLURONIC L92 emulsion formed a small amount of coagulum, but otherwise gave a stable emulsion. The AEROSOL OT emulsion flocculated to a mass of polymer.

The third step in these experiments was the inversion of the emulsion in water containing 0.5% TRITON X-305, AEROSOL A-102, or sodium lauryl sulfate (all being high-HLB emulsifiers). The TRITON X-305 and AEROSOL A-102 each gave stable emulsions from which the o-xylene was easily distilled; the sodium lauryl sulfate formed a little coagulum, and the o-xylene was distilled only with difficulty. The AEROSOL A-102 was selected for further evaluation.

Run 117 used 60 g 10% PVA (VINOL 125), 4 g 25% glutaraldehyde,and 1.5 g 25% p-toluene sulfonic acid emulsified in 100 g o-xylene containing 3 g PLURONIC L92 and ultrasonified using a Branson Ultrasonifier (setting 7; 50% duty cycle; 2 min.). The o-xylene/water azeotrope was stripped in a Buchler Rotovap rotary evaporator, and o-xylene was added to the emulsion until 45 ml water and 185 ml o-xylene were removed. The final emulsion was then ultrasonified as before mentioned for this run, the catalyst was added, and the emulsion was tumbled end-over-end in capped bottles for 12 hours at room temperature.

The emulsion was then inverted by adding it to an excess of water containing 0.2% TRITON X-305 or AEROSOL A-102. The result was an aqueous dispersion of crosslinked poly(vinyl alcohol) particles.

Those skilled in the art will appreciate that the molecular weight of the poly(vinyl alcohol) will affect the properties of the crosslinked polymer particles. A high molecular weight polymer requires fewer crosslinks to crosslink than a low molecular weight polymer. The critical parameter is the molecular weight between crosslinks. Although, I do not want to be held to this theory, the molecular weight of a polymer that would give the desirable property of forming a worm-like thread upon extrusion from a hypodermic needle is probably one having a relatively low-to-moderate molecular weight.

Other experiments were conducted using Dow Methocel K4M methylcellulose. This is a hydroxypropylmethyl cellulose (commonly known as "methyl cellulose") and is representative of this type of water-soluble derivative of natural cellulose. Methyl cellulose can be crosslinked by the reaction of its hydroxylgroups with such difunctional compounds as citric acid, glyoxal, dimethylolurea, water-soluble melamine-formaldehyde resins, quarternary ammonium salts, and water-soluble urea-formaldehye resins.

Acetal-like derivatives of water-soluble partially-alkylated celluloses were produced by known techniques by treating an alkylated cellulose such as methyl cellulose with an aldehyde such as glyoxal or pyruvic aldehyde having the general formula R—CO—CO—H, in which R may be a hydrogen or alkyl group, and removing the water from the reaction products, e.g., by drying on a glass plate. The products obtained were insoluble in water, acetone, and low monohydric aliphatic alcohols.

The methyl cellulose was dissolved by wetting the powdered polymer at 75–85° C. and then adding the remaining water while cooling and stirring. The clarity of the solution was improved by chilling to less than 10° C. 16 g 1% aqueous methyl cellulose was mixed in the conventional manner with 0.1 g hexamethoxylmethyl melamine (CYMEL 300) and 0.0128 g p-toluene sulfonic acid catalyst and heated for 20 minutes at 50° C. to form a crosslinked gel. When heated, instead, for 30 minutes at 60° C., a large mass of crosslinked polymer was formed. This crosslinking reaction was carried out in the emulsion.

50 g of a solution containing 1% methyl cellulose, 0.15 g CYMEL 300, and 0.070 g p-toluene sulfonic acid was emulsified in 50 g o-xylene containing 5.0 g SPAN 60. The emulsion was ultrasonified (setting 5; 10% duty cycle; 5 min.) to give an emulsion of 0.20–0.40 micrometers droplet size. The emulsion was then heated for 30 minutes at 70° C. to crosslink the polymer droplets. Afterwards, the emulsion was then inverted in 800 ml water containing 10 g TRITON X-305 (HLB 17.3). Optical microscopy showed that the final emulsion, after being inverted in water was flocculated. Based on this observation, it was believed that a high HLB emulsifier might not be suitable for the inversion; accordingly, other such emulsifiers were tried.

TRITON X-102 (an octylphenoxy polyethoxy ethanol, HLB 14.6, available commercially from Union Carbide) in 9:1 water-emulsifier ratio did not invert the emulsion; TRITON N-101 an nonylphenoxy polyethoxy ethanol, HLB 13.4, Union Carbide) gave similar results; TRITON X-405 (HLB 17.9) and TRITON X-305 (HLB 17.3) gave separation into two layers. Optical microscopy showed there was no flocculation with TRITON X-102 OR TRITON N-101, slight flocculation with TRITON X-405, and much more flocculation with the TRITON X-305.

In another experiment 50 g 1% aqueous methyl cellulose containing 0.25 g CYMEL 300 and 0.06 g p-toluene sulfonic acid was emulsified in 70 g o-xylene containing 7 g SPAN 60. The emulsion was subjected to hand-homogenization and ultrasonification, and then was stirred at 158 rpm in a round-bottom flask with a conventional laboratory stirrer for 2.5 hours at 60° C. 50 ml of this emulsion was inverted in 500 g water containing 5 g TRITON X-405 (HLB 17.9) to give an aqueous dispersion of the crosslinked methyl cellulose/CYMEL 300 particles.

A further experiment was conducted using 50 g 2.5% aqueous carboxymethyl cellulose solution containing 0.20 g CYMEL 300 and 0.06 g p-toluene sulfonic acid. This water-soluble polymer solution was emulsified in 50 g o-xylene containing 10% SPAN 60 and subjected to hand-homogenization and ultrasonification (setting 7; 50% duty cycle; 2 min), and heated for 1 hour at 62° C. while being stirred at 240 rpm, to prepare an aqueous dispersion of crosslinked carboxymethyl cellulose particles.

Aqueous solutions of poly(vinyl alcohol) (10%) and methylcellulose (5%) each containing glutaraldehyde were emulsified in o-xylene containing 10% or 15% SPAN 60 in polymer solution/o-xylene ratios of 1:1 and 1:2 and allowed to react at room temperature in capped bottles. 10 g 5% methyl cellulose and 6.0 g (%) glutaraldehyde failed to react after 14 hours at room temperature or 30 minutes at 60° C. 10 g 5% methyl cellulose emulsified in 10 g o-xylene containing 10% SPAN 60, with and without 1.0 g glutaraldehyde, also failed to react at room temperature. 10 g 5% methyl cellulose emulsified in 30 g o-xylene containing 15% SPAN 60, with and without 1.0 g 25% glutaraldehyde, gave slightly better results. Similarly, 20 g 15% PVA with 10 g 25% glutaraldehyde failed to react after 14 hours at room temperature.

Generally, the CYMEL 300 showed a significant solubility in the o-xylene as did the p-toluene sulfonic acid. At 40° C., the CYMEL 300 polymerized in o-xylene to form a precipitate. In contrast, glutaraldehyde did not dissolve in the o-xylene, even at 60° C. TETRONIC 1102 water-in-oil emulsifier was effective in emulsifying the methyl cellulose in o-xylene. TRITON X-405 (HLB 17.9) was effective in inverting these TETRONIC 1102-stabilized emulsions in water. Neither methyl cellulose nor PVA reacted with glutaraldehyde within 14 hours at room temperatures or 2 hours at 70° C. The combination of PVA or methyl cellulose and glutaraldehyde with a few drops of hydrochloric acid reacted after 1.5–2.0 hours at 100° C.

Crosslinking of Chondroitin Sulfate in Aqueous Solution

Tables XX and XXI show that the crosslinking of chondroitin sulfate with XAMA-7 crosslinking agent did not give the desired hydrophilic chondroitin sulfate gel (as it did with sodium alginate) even at the lower chondroitin sulfate/XAMA-7 weight ratios. Instead, a white, amorphous precipitate was formed. Table XX shows that decreasing the XAMA-7 concentration at constant chondroitin sulfate concentration (ph 7.5) so as to give chondroitin sulfate/XAMA-7 ratios of 2.0–4.0 also gave a white, amorphous precipitate. The amount of this precipitate decreased with increasing chondroitin sulfate/XAMA-7 ratio.

TABLE XX

Crosslinking of Chondroitin Sulfate with XAMA-7

| | Chondroitin Sulfate | | | | | |
|---|---|---|---|---|---|---|
| Run No. | CS (%) | CS (g) | Water* (g) | XAMA-7 (g) | CS/XAM-7 Ratio | Results** | Time (hr) |
| CSX-071 | 7 | 0.219 | 2.906 | 0.219 | 1.0 | precipitation | >0.8 |
| CSX-072 | 7 | 0.219 | 2.906 | 0.175 | 1.3 | precipitation | >0.8 |
| CSX-073 | 7 | 0.219 | 2.906 | 0.146 | 1.5 | precipitation | >0.8 |
| CSX-074 | 7 | 0.219 | 2.906 | 0.125 | 1.8 | precipitation | >0.8 |
| CSX-075 | 7 | 0.219 | 2.906 | 0.110 | 2.0 | precipitation | >0.8 |
| CSX-076 | 7 | 0.219 | 2.906 | 0.0735 | 3.0 | precipitation | >24 |
| CSX-077 | 7 | 0.219 | 2.906 | 0.0540 | 4.0 | precipitation | >24 |
| CSX-078 | 8 | 0.219 | 2.906 | 0.0438 | 5.0 | precipitation | >24 |

*pH 7.5
**formation of white, amorphous precipitate; no visible gelation

This white, amorphous precipitate was attributed to the formation of a tight, inelastic gel by crosslinking of the low-molecular-weight chondroitin sulfate. This sample of chondroitin sulfate appeared to have a lower molecular weight than the sodium alginate or hyaluronic acid samples used earlier, and its 10% solution had a low viscosity.

When the sodium alginate was replaced with the chondroitin sulfate in the procedure used to prepare hydrophilic sodium alginate microspheres, the product resembled an inverse latex more than an inverse suspension. The molecular structure of chondroitin sulfate contains a —OSO$_3$Na group in addition to the carbonyl and hydroxyl groups. This is the major difference between chondroitin sulfate, and hyaluronic acid and sodium alginate, which gave different results. When 3 g water was shaken with 3 g toluene in a small vial, and 0.15 g chondroitin sulfate was added, an oil-in-water emulsion was formed. At pH higher than 10, this effect was more pronounced. Thus, chondroitin sulfate is a special polysaccharide compared with hyaluronic acid and sodium alginate; it acted as an emulsifier in alkaline solution because of the —OSO$^3$Na group.

TABLE XXI

Crosslinking of Chondroitin Sulfate with XAMA-7

| Run No. | CS (%) | CS (g) | Water* (g) | XAMA-7 (g) | CS/ZAMA-7 Ratio | Results* |
|---|---|---|---|---|---|---|
| CSX-082 | 8 | 0.250 | 2.875 | 0.1261 | 2.0 | ++++ |
| CSX-083 | 8 | 0.250 | 2.875 | 0.0855 | 3.0 | +++ |
| CSX-084 | 8 | 0.250 | 2.875 | 0.0625 | 4.0 | ++ |
| CSX-085 | 8 | 0.250 | 2.875 | 0.0500 | 5.0 | + |

*pH 8.0
**formation of white precipitate in >7 hours; no gelation

Crosslinking of Hyaluronic Acid in Aqueous Solution

Hyaluronic acid (0.14 g) was dissolved in 2.0 g water to give a 7% semi-solid transparent gel. This gel was diluted with 2.0 g water to give an immobile 3.5% gel. When 1.0 g of this 3.5% hyaluronic acid gel was diluted with 1.5 g water, it gave a viscous liquid that flowed slowly when inverted. XAMA-7 crosslinking agent (0.15 g) was added to give a hyaluronic acid/XAMA-7 ratio of 0.23; after 30 minutes, a white elastic gel was formed.

Table XXII shows that the pH range 7–9 was favorable for the crosslinking of hyaluronic acid, but that the pH range 12–13 was unfavorable. Table XXIII shows that hyaluronic acid/XAMA-7 ratios lower than 0.2–0.4 gave the best gels for the preparation of the crosslinked hyaluronic acid microspheres; ratios higher than 0.6–2.0 gave poorer gels that were not satisfactory for the microspheres, and ratios of 1.5–2.0 gave inelastic and immobile gels after 24 hours at room temperature.

Table XXIV, which used the lower-molecular-weight hyaluronic acid (0.75×10$^6$), showed different results. The higher-molecular-weight hyaluronic acid had to be used at a concentration of 1.5%; higher concentrations gave immobile gels. The lower-molecular-weight hyaluronic acid was used at 2.5% concentration; this gave a mobile solution; higher concentrations such as 3.5% gave immobile gels. The optimum hyaluronic acid/XAMA-7 ratio for producing an elastogel was 0.5 for the lower-molecular-weight hyaluronic acid and 0.25 for the higher-molecular-weight. More XAMA-7 was required to crosslink the lower-molecular-weight hyaluronic acid to a suitable elastogel than for the higher-molecular-weight hyaluronic acid. This trend was expected: the lower the molecular weight, the greater the number of crosslinks required for insolubility. There may be some intramolecular crosslinking of the higher-molecular weight hyaluronic acid.

TABLE XXII

Crosslinking of Higher-Molecular-Weight* Hyaluronic Acid with XAMA-7 at Different pH

| Run No. | Hyaluronic Acid (HA) (%) | HA (g) | Water (g) | pH | XAMA-7 (g) | HA/XAMA-7 Ratio | Time to Cloud** (min) | Time to Gelation (min) |
|---|---|---|---|---|---|---|---|---|
| HAX-1513 | 1.5 | 0.0450 | 3.0025 | 13 | 0.0490 | 0.92 | — | — |
| HAX-1512 | 1.5 | 0.0450 | 3.0011 | 12 | 0.0457 | 0.99 | — | — |
| HAX-1511 | 1.5 | 0.0450 | 3.0078 | 11 | 0.0452 | 1.0 | 85 | 420 |
| HAX-1510 | 1.5 | 0.0450 | 3.0000 | 10 | 0.0450 | 1.0 | 60 | 150 |
| HAX-1509 | 1.5 | 0.0450 | 3.0000 | 9 | 0.0458 | 0.98 | 60 | 130 |
| HAX-1508 | 1.5 | 0.0450 | 3.0010 | 8 | 0.0455 | 0.93 | 60 | 120 |
| HAX-1507 | 1.5 | 0.0450 | 3.0021 | 7 | 0.0450 | 1.0 | 60 | 120 |

*1.2 × 10$^6$
**formation of a cloudy precipitate

TABLE XXIII

Crosslinking of Higher-Molecular-Weight* Hyaluronic Acid with XAMA-7 at Different HA/XAMA-7 Ratios at pH 8

| Run No. | Hyaluronic Acid (HA) (%) | HA (g) | Water (g)g) | pH | XAMA-7 (g) | HA/XAMA-7 Ratio | Time to Cloud** (min) | Time to Gelation (min) |
|---|---|---|---|---|---|---|---|---|
| HAX-15820 | 1.5 | 0.0458 | 3.0050 | 8 | 0.0229 | 2.0 | >180 | >1440*** |
| HAX-15817 | 1.5 | 0.0454 | 3.0053 | 8 | 0.0270 | 1.75 | 100 | >1440*** |

TABLE XXIII-continued

Crosslinking of Higher-Molecular-Weight* Hyaluronic Acid with XAMA-7 at Different HA/XAMA-7 Ratios at pH 8

| Run No. | Hyaluronic Acid (HA) | | | | XAMA-7 (g) | HA/ XAMA-7 Ratio | Time to Cloud** (min) | Time to Gelation (min) |
|---|---|---|---|---|---|---|---|---|
| | HA (%) | HA (g) | Water (g)g) | pH | | | | |
| HAX-15815 | 1.5 | 0.0454 | 3.0021 | 8 | 0.0303 | 1.5 | 80 | >1440*** |
| HAX-15810 | 1.5 | 0.0456 | 3.0000 | 8 | 0.0454 | 1.0 | 60 | 120 |
| HAX-15808 | 1.5 | 0.0456 | 3.0023 | 8 | 0.0563 | 0.8 | 60 | 120 |
| HAX-15806 | 1.5 | 0.0456 | 3.0029 | 8 | 0.0750 | 0.6 | 60 | 120 |
| HAX-15805 | 1.5 | 0.0459 | 3.0010 | 8 | 0.0900 | 0.5 | 60 | 120 |
| HAX-15804 | 1.5 | 0.0460 | 2.9997 | 8 | 0.1121 | 0.4 | 45 | elastogel |
| HAX-15802 | 1.5 | 0.0452 | 3.0003 | 8 | 0.2250 | 0.2 | 40 | elastogel |

*$1.2 \times 10^6$
**time to form a cloudy, white precipitate
***inelastic, movable gel

TABLE XXIV

Crosslinking of Lower-Molecular-Weight* Hyaluronic Acid with XAMA-7 at Different HA/XAMA-7 Ratios at pH 8

| Run No. | Hyaluronic Acid (HA) | | | | XAMA-7 (g) | HA/ XAMA-7 Ratio | Gelation Cloud | Time** Gel |
|---|---|---|---|---|---|---|---|---|
| | HA (%) | HA (g) | Water (g) | pH | | | | |
| 25815 | 2.5 | 0.0769 | 3.000 | 8 | 0.0522 | 1.5 | 50 | >180 |
| 25812 | 2.5 | 0.0769 | 3.000 | 8 | 0.0641 | 1.2 | 50 | >180 |
| 25810 | 2.5 | 0.0769 | 3.000 | 8 | 0.0760 | 1.0 | 50 | 180 |
| 25808 | 2.5 | 0.0769 | 3.000 | 8 | 0.0983 | 0.8 | 50 | 130 |
| 25805 | 2.5 | 0.0769 | 3.000 | 8 | 0.1526 | 0.5 | 50 | 60*** |

*$0.75 \times 10^6$
**in minutes
***elastogel

Crosslinking in Aqueous Emulsion

Hyaluronic acid microspheres were prepared using the same procedure used to prepare the sodium alginate microspheres. First, ammonium hydroxide was added to raise the pH of the hyaluronic acid solution to 10–11; the solution was then emulsified in toluene to give the desired droplets. Then, the XAMA-7 crosslinking agent was added and the pH was decreased to 8–9 using acetic acid. The system was then allowed to crosslink at room temperature for 4 or 24 hours; then, the isopropanol dehydrating agent was added. The sample formed two layers: the top layer was separated and washed with methanol, to give a single phase without microspheres. The failure to produce microspheres was attributed to the 1.75 or 2.0 hyaluronic acid/XAMA-7 ratio and the high molecular weight of the hyaluronic acid ($1.2 \times 10^6$). A 3.5% concentration of hyaluronic acid gave an immobile gel. A 1.5% solution of hyaluronic acid was viscous enough to make the inverse droplets in the presence of Span 60 emulsifier in toluene solution. This may be the major reason why low-concentration polymer solutions require a high concentration of crosslinking agent.

To prepare hydrophilic hyaluronic acid gel microspheres, 100 g aqueous solution containing 1.5 g hyaluronic acid was dispersed in 100 g toluene containing 1.0% w/w Span 60 using a mechanical stirrer at 1000 rpm for 15 minutes. Then, 6.0 g XAMA-7 crosslinking agent was added, the dispersion was stirred for another 5 hours, after which 100 ml isopropanol dehydrating agent was added to further harden the microspheres formed. The upper layer of toluene/isopropanol mixture was separated by decantation. The microspheres were washed twice with 200 ml isopropanol, separated by ultracentrifugation, and dried in an air oven at 75° C.

Table XXV shows that, for the higher molecular weight ($1.2 \times 10^6$), the weight ratio of hyaluronic acid/XAMA-7 crosslinking agent and the pH of the system were important: hyaluronic acid/XAMA-7 ratios of less than 0.25 and control of the pH, first at 10–11 to prepare the emulsion, then at 8–9 for the crosslinking step, were required to give the desired microspheres. Hyaluronic acid/XAMA-7 ratios higher than 0.5, such as 1.25 or 1.75 (Runs HAB-01 and -02), did not give the desired microspheres. If the pH of the system was kept at 7–8, the microspheres became crosslinked, but easily stuck together.

Table XXVI shows that the lower-molecular-weight ($0.75 \times 10^6$) hyaluronic acid gave spherical microspheres at a hyaluronic acid/XAMA-7 ratio of 0.5. Most of these spherical microspheres were smaller than 212 micrometers.

The molecular weight of the hyaluronic acid used in Table XXV ($1.2 \times 10^6$) was greater than that used in Table XXVI ($0.75 \times 10^6$). More XAMA-7 was required for crosslinking this higher-molecular-weight hyaluronic acid than for the lower-molecular-weight hyaluronic acid. This trend was the opposite of that expected and was attributed to the possible intramolecular crosslinking of the higher-molecular-weight hyaluronic acid. The desired elastic gel microspheres were obtained in both cases.

The drying of the microspheres was also important; after the microspheres were washed with the isopropanol dehydrating agent, five drops of the suspension were placed on a glass slide and heated in an air oven at 75° C.; when the water was evaporated, the microspheres were generally smaller in size, with smooth surfaces, as compared with those of the whole sample dried in the oven. The efficiency of the drying method must be investigated further. A fluidized bed dryer may be necessary to dry the microspheres on larger scale.

TABLE XXV

Higher-Molecular-Weight* Hyaluronic Acid Microspheres Crosslinked with XAMA-7

| Run No. | HAB-01 | -02 | -03 | -04 |
|---|---|---|---|---|
| Water Phase (g) | | | | |
| Hyaluronic acid | 1.5 | 1.5 | 1.5 | 1.5 |
| Water | 100 | 100 | 100 | 100 |
| pH** | 7–8 | 7–8 | 7–8 | 10–12 |
| Oil Phase (g) | | | | |
| Toluene | 100 | 100 | 100 | 100 |
| Span | 1.0 | 1.0 | 1.0 | 1.0 |
| Crosslinking Agent (ml) | | | | |
| XAMA-7 | 0.67 | 1.1 | 5.0 | 5.0 |
|  | 0.80 g | 1.3 g | 6.0 g | 6.0 g |
| HA/XAMA-7 Ratio | 1.75 | 1.25 | 0.25 | 0.25 |
| pH** | 7–9 | 7–9 | 7–9 | 7–9 |
| Stirring Rate (rpm) | 1000 | 800 | 1000 | 1000 |
| Reaction time (hr) | 5 | 13 | 5 | 12 |
| Dehydrating agent | | | | |
| Isopropanol (ml) | 100 | 100 | 2 × 200 | 2 × 200 |
| Methanol (ml) | 100 | 100 | — | — |
| Particle Shape | liquid | liquid | aggregated | spherical |
| Microspheres (%) | — | — | — | |
| a. >150 um | — | — | — | 11.5 |
| b. 150–212 um | — | — | — | 12.6 |
| c. 212–150 um | — | — | 69.7 | 68.8 |
| d. <150 um | — | — | 30.3 | 7.0 |

*$1.2 \times 10^6$
**pH adjusted with concentrated ammonium hydroxide or acetic acid

TABLE XXVI

Lower-Molecular-Weight Hyaluronic Acid* Microspheres Crosslinked with XAMA-7

| Run No. | LHAB-01 | LHAB-02 |
|---|---|---|
| Water phase (g) | | |
| LHA | 2.5 | 2.5 |
| Water | 100 | 100 |
| pH** | 10–11 | 10–11 |
| Oil Phase (g) | | |
| Span 60 | 1.0 | 1.0 |
| Toluene | 100 | 100 |
| Crosslinking Agent (ml) | | |
| XAMA-7 | 4.2 | 4.2 |
|  | 5.0 g | 5.0 g |
| LHA/XAMA-7 wt ratio | 0.5 | 0.5 |
| pH** | 8–9 | 8–9 |
| Stirring rate (rpm) | 1000 | 1000 |
| Reaction time (hr) | 12 | 12 |
| Dehydrating agent (ml) | | |
| Isopropanol | 2 × 200 | 2 × 200 |
| Particle shape | spherical | spherical |

TABLE XXVI-continued

Lower-Molecular-Weight Hyaluronic Acid* Microspheres Crosslinked with XAMA-7

| Run No. | LHAB-01 | LHAB-02 |
|---|---|---|
| Microsphere size (%) | | |
| a. >250 um | 5.9 | 23.9 |
| b. 250–212 um | 6.9 | 3.4 |
| c. 212–150 um | 35.3 | 24.2 |
| d. <150 um | 51.2 | 48.6 |

*$0.75 \times 10^6$
**pH adjusted with concentrated ammonium hydroxide or acetic acid

EXAMPLE 29

This example illustrates a 500 ml batch size production of microspheres.

1. Prepare Solutions

Solution A: Dissolve 15.00 g NaOH in 500 ml distilled and deionized water.

Solution I: Mix 0.5 g hyaluronic acid with 25 ml of Solution A in a 50 ml test tube.

Solution B: Mix 9.0 g Sobitan monostearate (Span-60) in 150 ml toluene in a 500 ml glass bottle.

Solution II: Add 10 ml ethylene glycol diglycidyl ether (EGDGE), or other diepoxide type crosslinking agent, to Solution B.

2. Cross-linking Reaction

Step 1: Pour Solution I in a 500 ml three-neck indented glass round bottom reactor, which was pre-equilibrated at 25° C.±2° C.

Step 2: Set stirring speed of a shaft agitator at 500 RPM±10 RPM; allow to stir continuously for 20 minutes±2 minutes.

Step 3: Add 0.5 ml of polyoxyethylene [20] sorbitan monooleate (Tween-80) into reactor.

Step 4: Continue stirring for 10 minutes±1 minute, add 5.0 ml of cross-linking agent (EGDGE) into the reactor. (Note: this is additional to the cross-linking agent used in Solution II).

Step 5: Continue mixing for 10 minutes±2 minutes, then pour Solution II into the reactor.

Step 6: Increase agitation speed immediately up to 1,000 RPM±50 RPM.

Step 7: Stop the agitation and cease the run at 9.0 hours±30 minutes.

3. Washing, Purification & Sieving

Step 8: Add 300 ml methanol into the resulting gel suspension and continuously stir for 15 minutes±2 minutes at 1000 RPM±50 RPM.

Step 9: Stop the washing, carefully remove agitator apparatus from reactor solution, and then separate beads from gel solution by vacuuming filtration.

Step 10: Wash the beads with 400 ml acetone and continue vacuuming for 5–8 minutes.

Step 11: Reconstitute the beads with 2 liters of distilled deionized water and stir at 100 RPM, 20–24° C. for overnight.

Step 12: Sieve the beads using the USA Standard Testing Siever to the desired size range from 20 to 90 pm.

4. Prepare For Coupling of Bioactive Molecules (optional)

Step a: Wash 10 ml of gravity-packed beads with 100 ml water 3 times.

Step b: Suspend the washed beads in 10 ml water and adjust pH to 4.0–4.5.

Step c: Dissolve 0.5 mg of Bioactive Molecule in 2.0 ml water and adjust pH to 4.0–4.5.

Step d: Add 2.5 mmol (about 500 mg) Coupling Agent to the beads' suspension and maintain the pH at 4.0–4.5.

Step f: Immediately add the solution of Bioactive Molecule into the bead suspension and maintain the pH at 4.0–4.5.

Step g: Place the bead suspension in a shaker and shake for 4 hours at room temperature.

Step h: Wash the gel sequentially with 2×100 ml water, 100 ml 0.1 M acetic acid, 100 ml water, 100 ml 0.1 M NaOH, 100 ml 0.5 M NaCl, and 100 ml PBS.

Step i: Store the bioactive molecule coupled beads in PBS containing anti-microbial agents at 4° C.

EXAMPLE 30

Polysaccharide microspheres were prepared according to the process of Example 29. Microspheres ranging in size from 10 $\mu$m to 200 $\mu$m were prepared using alginate of various formulations, chondroitin sulfate, hyaluronates with different molecule weights, inulin and cross-linked hydroxypropylmethyl cellulose (HPMC)—a "fiber-type" implant (i.e. not spherical) was also prepared according to the process of Example 29 using hydroxypropylmethyl cellulose. The size, rigidity and rheology characteristics of the microspheres were easily controlled by varying the process parameters.

Protocol for Synthesis of Cross-Linked Hydoxypropylmethyl Cellulose (HPMC)

| | |
|---|---|
| Aqueous: | 1 gram HPMC in 50 ml of 0.5M NaOH + 30 gram of EGDGE + 3.2 grams of Tween 80 |
| Organic: | 100 ml Toluene |
| Reaction: | Mix organic into aqueous, after mixing well 51.02 grams EGDGE are added. Stir overnight |
| Final Reaction: | 20 Ml of 0.5M NaOH + 5 gram EGDGE is added Heat the system to 70 deg. C. for two hours Cool to room temperature |
| Purification: | Wash with 1-propanol 3 times, wash with acetone 1 time wash with dionized water 3 times |
| Depyrogenation: | Using 1.0M NaOH overnight at room temperature |
| Storage: | Depyrogenated PBS |

Protocol for Synthesis of Cross-Linked Sodium Hyaluronate Gel (General)

Aqueous solution: 1.0 g Sodium Hyaluronate in 50 mL of 0.75M NaOH+3 mL Tween 80

Organic solution: 150 mL toluene+9 mL Sorbitan Triooleate (SPAN 85)

Reaction: Add 25 mL Ethylene glycol diglycidyl ether (EGDGE) to aqueous solution when sodium hyaluronate was completely dissolved in aqueous solution in a reactor placed in waterbath at 70° C. Organic solution was added after EGDGE dissolved in aqueous solution. The reactor was cooled down to room temperature 30 min after addition of organic solution. Add 75 mL EGDGE and continue stirring overnight.

Purification: Was in 1-propanol (3 times gel volume) 3 times, acetone (3 times gel volume) 2 times, distilled H$_2$O (5 times gel volume) 2 times. The beads were boiled in distilled H$_2$O for 30 minutes.

Protocol for Synthesis of Cross-Linked Chondroitin Sulfate A Gel (General)

Aqueous solution: 1.0 Chondroitin Sulfate A in 50 mL of 0.75 M NaOH+3 mL Tween 80

Organic solution: 150 mL toluene+9 mL Sorbitan Triooleate (SPAN 85)

Reaction: Add 25 mL Ethylene glycol diglycidyl ether (EGDGE) to aqueous solution when chondroitin sulfate A was completely dissolved in aqueous solution in a reactor placed in waterbath at 70° C. Organic solution was added after EGDGE dissolved in aqueous solution. The reactor was cooled down to room temperature 30 min after addition of organic solution. Add 75 mL EGDGE and continue stirring overnight.

Purification: Wash in 1-propanol (3 times gel volume) 3 times, acetone (3 times gel volume) 2 times, distilled H$_2$O (5 times gel volume) 2 times. The beads were boiled in distilled H$_2$O for 30 minutes.

Protocol for Making Inulin Beads (General)

Aqueous solution: 1.0 g Inulin in 50 mL of 1M NaOH+3 mL Tween 80

Organic solution: 200 mL toluene+12 mL SPAN 85 (Sorbitan Triooleate)+20 mL EGDGE (Ethylene glycol diglycidyl ether)

Reaction: Add 35 mL of EGDGE to solution I, then 178 mL of solution II was immediately added to solution I after EGDGE dissolved in solution I. Stir for ~40 hrs.

Purification: Wash in 1-propanol (2 times gel volume 4 times, acetone (2 times gel volume) 2 times, distilled H$_2$O (5 times gel volume) 5 times. The beads were boiled in distilled H$_2$O for 30 minutes.

Depryogenation: Using 0.5M NaOH, overnight at room temperature.

Protocol for Synthesis of Cross-Linked Alginate Gel (General)

Aqueous solution: 1.0 g Alginate in 50 mL of 0.5M NaOH +3 mL Tween 80

Organic solution: 150 mL toluene +6 mL Sorbitan Triooleate (SPAN 85)

Reaction: Add 10 mL of Ethylene glycol diglycidyl ether (EGDGE) to aqueous solution when alginate was completely dissolved in aqueous solution in a reactor placed in waterbath at 70° C. Organic solution was added after EGDGE dissolved in aqueous solution. The reactor was cooled down to room temperature 30 min after addition of organic solution. Add 30 mL EGDGE and continue stirring overnight Purification: Wash in 1-propanol (3 times gel volume) 3 times, acetone (3 times gel volume) 2 times, distilled H$_2$O (5 times gel volume) 2 times. The beads were boiled in distilled H$_2$O for 30 minutes.

EXAMPLE 31

The microspheres produced in Example 30 passed cytotoxicity, sterility and pyrogenicity tests and were found to be substantially non-toxic.

EXAMPLE 32

Immunogenecity tests were performed on two different batches of alginate microspheres and on the hyaluronate microspheres produced in Example 31 by implanting in animals. These microspheres elicited only a minimal immunological response in implanted animals.

EXAMPLE 33

An acute imflammation test was performed on microspheres produced according to Example 30. All materials were injected easily into the peritoneal cavity of mice. No mortality, morbidity, signs of toxicity, or any signs of distress were observed in the test animals. The test revealed that the type, but not shape, of implant material affects the short term inflammatory cell responses of the host to the implants. Hydroxypropylmethyl cellulose gels recruit more neutrophils than other materials. Hyaluronate microspheres attract more transient monocytes/macrophages than other materials tested.

EXAMPLE 34

Chronic implantation tests using the microspheres of Example 32 showed no adverse systemic or local tissue reaction to the implants. The microspheres retained their shape and size in the implant site.

EXAMPLE 35

It was found that the microspheres of Example 32 were easily extruded from 22 to 28 gauge hypodermic needles and delivered into tissues. No surgical incision or complicated procedure was necessary for implantation. The implant and surrounding tissue showed no sign of redness, irritation or swelling.

EXAMPLE 36

In this example, the batch size was 22 liters, the hydrophilic polymer was hyaluronic acid, the organic phase was toluene, the emulsifying agents were a combination of SPAN 60 and TWEEN 80, and the crosslinking agent was ethylene glycol deglycidyl ether (a diepoxide type crosslinker that crosslinks through OH groups).

The agitation speed was only 400 rpm (a speed fast enough to mix the reagents, permitting the formation of a stable emulsion, but not so fast as to create excessive mechanical stress and cause shearing and crosslinking breakage).

The reaction was run at 25° C. and the pH was adjusted to 7.4 after crosslinking. The reaction time was 8.5 hours followed by washing with methanol, acetone and then resuspension in phosphate buffered saline.

The reaction yielded particles having a size range of 10 $\mu$m to 50 $\mu$m, with approximately 75% of the particles being approximately 30 $\mu$m.

The microparticles exhibited excellent stability. Under constant high shear force generated by agitation at 34.0 liter/sec mixing for 2 hours, the apparent viscosity changed only slightly (about 2.9%). The viscosity would drop significantly (e.g. more than 10%) if the particles break down into smaller particles and particle fragments.

The particles formed in this example were surprisingly easy to extrude through a 22 gauge needle, requiring less than 5 pounds per square inch.

EXAMPLE 37

We suspended Sephadex beads of different sizes and rigidities in either non-crosslinked hyaluronate in saline (1 mg/ml) or plain saline solutions and compared the extrusion force between the two. We found no difference between Sephadex suspensions with or without hyaluronate, demonstrating that the hyaluronate does not function as a delivery aid when mixed with injectable microspheres.

Even though non-crosslinked hyaluronate di d function as an injection aid, it was found to be an useful ingredient for injectable implants because it reduced host inflammatory responses to implant materials. Thus, materials such as Sephadexs or any other crosslinked polysaccharide microspheres which may not be inherently biocompatible to the host, may be employed as implant materials when used in conjunction with hyaluronate.

It is postulated that the hyaluronate may "mask" the implant microsphere material, thereby preventing the host inflammatory cells (i.e., neutrophils, macrophages and monocytes) from recognizing and responding immunologically to them. Subsequent to implantation, when the hyaluronate likely is degraded, the tissue regeneration phase has begun and inflammatory cells may no longer play a role at the implant site.

I. Objective—To hydrate Sephadex beads in a solution of hyaluronate in PBS equal to 1 mg. hyaluronate per ml. of PBS.

II. Purpose—To add lubrication to the beads to ease flow through the needle.

III. Equipment
Instron 4200 series Interface with Load
Cell#2418–80
Upper Compression plate for Instron
30 cc Syringes (two for each test)
3 cc Syringes—Becton Dickinson Cat #9585 (one for each 3 cc of material for testing)
22G/1 inch needles—Becton Dickinson Cat #5155
Drying stand for transurethral needles
Analytical Balance (RR-0026/Cal. due Jul. 29, 1996)
Test tube rack
Rubber stoppers for syringes
Male/male lure-lok fittings V. Testing Materials
Sephadex G-200-50—Sigma (lot# 64H1244)
Sephadex G-75-50—Sigma ((lot# 75H907)
Sephadex G-50-50—Sigma (lot# 124H0078)
Sephadex G-25-50—Sigma (lot# 12H1057)
Dulbecco's Phosphate Buffered Saline without calcium chloride and magnesium chloride
Sigma—Cat #D-5527, Lot #44H4646, Exp. May 1996
Sodium Hyaluronate
Life Core—Cat #1011-1100, Lot# 1-91323-1

V. Procedure
A. Make up hyaluronate solution in PBS
 1) 0.210 gm. hyaluronate added to 210 ml. of PBS
 2) Place on stir plate and stir with magnetic stirrer until completely in solution.
B. Prepare 30 cc syringes.
 1) Remove plunger
 2) Stopper bottom with rubber stopper
 3) Label with type of Sephadex to be added
C. Add 10 cc of appropriate solution to each syringe.
D. Weigh out 0.5 gm. of Sephadex for each syringe and add to syringe.
E. Bring to 30 cc volume with appropriate solution.
F. Gently seat plunger back in place.
G. Invert syringe, remove rubber stopper and push out trapped air.
H. Replace stopper and let stand on plunger in test tube rack overnight.
I. Record total amount of swelled beads.
J. Remove stopper and push out liquid portion that does not contain Sephadex.
K. Hook Male/Male fitting on end of syringe.
L. Hook second 30 cc syringe to sample.
M. Mix sample by pushing back and forth between the two syringes five times.
N. Remove second 30 cc syringe.
O. Use fitting to transfer sample to 3 cc syringes, 3 cc per syringe.
P. Place 22 G needle on each syringe of sample.
Q. Test on extrudability on the Instron machine.

VI. Results

| | | SEPHADEX/HYALURONATE | | | |
|---|---|---|---|---|---|
| SAMPLE SEPHADEX | PLUS OR MINUS HYALURONATE | PACKED BEAD VOL. IN CC'S | NUMBER OF SYRINGES | MAXIMUM LOAD IN LBS. MEAN (STD. DEV.) | AVG. LOAD BETWEEN LIMITS MEAN (STD. DEV.) |
| G-200-50 | PLUS | 15 | 5 | 1.221 (.143) | 0.6657 (.0512) |
| G-200-50 | MINUS | 16 | 5 | 1.269 (.109) | 0.5877 (.1444) |
| G-50-50 | PLUS | 6 | 2 | 1.299 (.053) | 0.8455 (.0980) |
| G-50-50 | MINUS | 7 | 1 | 1.224 (*) | 1.019 (*) |
| G-25-50 | PLUS | 3 | 1 | 21.2 (*) | 3.363 (*) |
| G-25-50 | MINUS | 3 | 1 | 1.272 (*) | 0.78 (*) |
| G-75-50 | PLUS | 9 | 3 | 1.174 (.090) | 0.6244 (.0843) |
| G-75-50 | MINUS | 9 | 2 | 1.224 (.016) | 0.774 (.0129) |

VII. Conclusion

The hyaluronate at this level appeared to have little or no effect on the Sephadex. A higher concentration of hyaluronate may give a more positive result.

EXAMPLE 38

This 30-day implantation study showed that the smaller size microspheres trigger less inflammatory responses and therefore are more desirable than larger size microspheres when used as an injectable implant.

Overall Purpose:

The objective of this study was to investigate whether the particle size of implanted polysaccharide microspheres influences long term inflammatory and/or fibrotic responses in a rat model.

Animals:

Male Sprague Dowley rats in good health, weighing approximately 100 grams, were used in the study.

Test Materials and Animal ID Number
1. Test material #A (animal A1):
    Hyaluronic Gel (<20–>150 μm bead size)
2. Test material #B (animals B1 and B2):
    Hyaluronic Gel (20–45 μm bead size)
3. Test material #C (animals C1 and C2):
    Hyaluronic Gel (45–33 μm bead size)
4. Test material #D (animals D1 and D2):
    Hyaluronic Gel (63–90 μm bead size)
5. Test Material #E (animals E1 and E2):
    Hyaluronic Gel (90–≧150 μm bead size)

Test Protocol:
1. Male Sprague Dowley rats (1 animal for test material #A, 2 animals per group for the other test materials, total 9 rats) were purchased Taconic Farms (Germantown, N.Y.) and kept in the Albany Medical College Animal Resource Facility for 7 days prior to initiation of this study.
2. Rats were anesthetized with ketamine-xylazine (ketamine 80 mg/kg body weight and xylazine 12 mg/kg body weight) according to standard procedures. The fair on the back was then clipped.
3. 0.5 ml of test material was injected (by subscapular inoculation) into both the left and right sides of each animal.
4. After 30 days, rats were sacrificed by inhalation of $CO_2$. The implanted materials and the tissues surrounding them were recovered by careful dissection and fixed with Formalin.
5. The fixed material was embedded en bloc in paraffin, sectioned and stained with haematoxylin and eosin.

Results:

A. Material Injected:

Approximately 0.5 ml of the test materials were subscapularly administered to both left side and right side of animal. The weights of injected materials were measured and are listed in Table 1.

| | Weight of test Materials Implanted in Rats | |
|---|---|---|
| ID# | Left-WT (grams) | Right-Wt (grams) |
| A-1 | 0.62 | 0.59 |
| B-1 | 0.61 | 0.53 |
| B-2 | 0.65 | 0.59 |
| C-1 | 0.58 | 0.54 |
| C-2 | 0.48 | 0.53 |
| D-1 | 0.46 | 0.55 |
| D-2 | 0.53 | 0.59 |
| E-1 | 0.61 | 0.53 |
| E-2 | 0.49 | 0.52 |

B. Post Injection Animal Care

After implantation, the animals were observed for visible tissue responses around the implantation site. These were recorded at 1, 24, 72, and 144 hours post injection. The injection sites were scored on a scale of 0 to 3 as follows:

0=No reaction

1=Slight redness and swelling only over implant

2=Mild redness and swelling over implant and surrounding tissues

3=Severe redness and swelling over implant and surrounding tissues

| | Visible Tissue Responses to Implanted Test Materials | | | | |
|---|---|---|---|---|---|
| Test | | The score of tissue responses materials | | | |
| # | Animal | 1 hour | 24 hours | 72 hours | 144 hours |
| A | 1 | 0 | 0 | 0 | 0 |
| B | 1 | 0 | 0 | 0 | 0 |
| B | 2 | 0 | 0 | 0 | 0 |
| C | 1 | 0 | 0 | 0 | 0 |
| C | 2 | 0 | 0 | 0 | 0 |

-continued

Visible Tissue Responses to Implanted Test Materials

| Test | | The score of tissue responses materials | | | |
|---|---|---|---|---|---|
| # | Animal | 1 hour | 24 hours | 72 hours | 144 hours |
| D | 1 | 0 | 0 | 0 | 0 |
| D | 2 | 0 | 0 | 0 | 0 |
| E | 1 | 0 | 0 | 0 | 0 |
| E | 2 | 0 | 0 | 0 | 0 |

No externally visible inflammatory responses or other adverse tissue responses were observed.

C. Animal Weights

The weights of animals before and 30 days after implantation were measured. The test materials had no obvious effect on the growth of the test animals.

Weights and Weight Change in Implanted Animals

| Rat | Body weight (grams) | | |
|---|---|---|---|
| ID# | Initial | Final | Gain |
| A-1 | 95.1 | 327.4 | 232.3 |
| B-1 | 84.5 | 311.7 | 227.2 |
| B-2 | 102.6 | 349.6 | 247.2 |
| C-1 | 108.6 | 333.5 | 224.9 |
| C-2 | 100.6 | 334.1 | 233.5 |
| D-1 | 99.5 | 294.8 | 195.3 |
| D-2 | 94.4 | 324.7 | 230.3 |
| E-1 | 100.4 | 338.6 | 238.2 |
| E-2 | 98.4 | 308.6 | 210.2 |

D. Histopathology:

After 30 days implantation, the materials implanted were recovered, fixed and embedded as described above. The embedded samples were sectioned and stained with haematoxylin and eosin. The tissue responses were graded according to the extent of foreign body response (primarily, the numbers of foreign body giant cells present), fibrosis and extent of cellular infiltration (on a scale of 0 to 3):

0=No visible response
1=Weak response
2=Mild response
3=Strong response

Note: The grade 0–3 was designed for comparison purpose in order to differentiate the 5 studied materials. The interpretations for each test material (below) are also with the same purpose. There was no appearance of any adverse reaction in animals during a 30-day implantation with any of 5 polysaccharide materials. All 5 materials are considered safe for tissue implantation.

Type and extent of Tissue Reactions to Implants

| Test materials | Samples # | Foreign Body Responses | Fibrosis | Cell Filtration |
|---|---|---|---|---|
| A | 1 | 3+ | 1–2+ | 3+ |
| A | 2 | 3+ | 1+ | 3+ |
| B | 1 | 1–2+ | 2–3+ | 1+ |
| B | 2 | 1+ | 3+ | 0–1+ |
| C | 1 | 1–2+ | 1–2+ | 1–2+ |
| C | 2 | 1–2+ | 2+ | 1–2+ |

-continued

Type and extent of Tissue Reactions to Implants

| Test materials | Samples # | Foreign Body Responses | Fibrosis | Cell Filtration |
|---|---|---|---|---|
| D | 1 | 2+ | 2+ | 2+ |
| D | 2 | 2–3+ | 2+ | 2–3+ |
| E | 1 | 3+ | 2+ | 3+ |
| E | 2 | 3+ | 1–2+ | 3+ |

Test Material A

The foreign body reaction and chronic inflammatory response were quite evident around the implants. Significant fibrotic tissue (fibroblasts and collagen fibrils) was present in the capsules around the implant. Large numbers of foreign body giant cells and macrophages had penetrated the body of implants and enveloped individual particles of the test material.

Test Material B

These implants triggered only weak foreign body reactions. Strong fibrotic responses, notably an accumulation of large numbers of fibroblasts and collagen fibrils, were present. However, the cell material interaction was limited to the interface between and tissue. Cell penetration into the interstices of the implant body was minimal.

Test Material C

Mild foreign body responses and fibrotic responses were observed around the implants. Foreign body giant cells were abundant in the material/tissue interface. Mild cellular infiltration also occurred immediately surrounding the implants. However, most of the inner portions of the implant were free of invading cells.

Test Material D

The implants prompted mild peripheral foreign body and fibrotic responses. However, a significant number of foreign body giant cells and macrophages penetrated the material implants. Notably, small blood vessels (angiogenesis) had developed within the implants.

Test Material E

Strong foreign body reactions and mild fibrotic responses were found in the tissue immediately adjacent to these implants. Numerous foreign body giant cells occurred in most areas within and adjacent the implant.

Conclusion:

After implantation for 30 days, the different test materials triggered distinct tissue responses such as foreign body responses, fibrosis and cell infiltration. Test materials B and C triggered weak inflammatory response and mild fibrotic responses. In contrast, test materials A and E prompted marked inflammatory responses. The smaller size beads trigger only weak inflammatory responses and therefore are more desirable than larger size beads, which illicit a strong immunological response, when used for implantation.

EXAMPLE 39

Study of Acute Inflammatory Responses To Implanted Polysaccharide Biomaterials in Mice Overall Purpose:

The objective of this study is to investigate whether different crosslinked polysaccharide materials made according to the process of the present invention cause acute inflammatory responses in mice.

Test Materials

1. Test material #1: Hydroxypropymethyl Cellulose Fiber (length 150–500 $\mu$m, width 10–20 $\mu$m)

2. Test material #2: Inulin Beads (38–90 μm)
3. Test material #3: Alginate Beads (38–90 μm)
4. Test material #4: Chondroitin Sulfate Beads (38–90 μm)
5. Test material #5: Hyaluronic Acid Beads (38–90 μm)
6. Saline
7. Zymosan A (1 mg/ml, from *Saccharomyces cerevisiae*)

Test Protocol
1. Male Balb/c mice were purchased from Taconic farm (Germantown, N.Y.) and acclimated for 7 days prior to the initiation of this study.
2. Followed the implantation procedure, 1 ml of test materials was injected into mice peritoneums.
3. After implantation for 24 hours, mice were sacrificed and the peritoneal cells were then recovered with 5 ml of phosphate buffer saline.
4. The numbers of inflammatory cells (especial neutrophils and monocytes/macrophages) and total cells were determined by the cell specific enzyme activities.

Results:

| Test Materials | Animal # | Body Weight Before Implantation | After Implantation | Total Weight Injected |
|---|---|---|---|---|
| 1 | 1 | 21.84 grams | 19.83 grams | 1.012 grams |
| 1 | 2 | 20.24 grams | 18.46 grams | 1.011 grams |
| 1 | 3 | 20.63 grams | 18.58 grams | 1.029 grams |
| 2 | 1 | 21.04 grams | 19.24 grams | 1.095 grams |
| 2 | 2 | 20.00 grams | 18.27 grams | 1.125 grams |
| 2 | 3 | 19.73 grams | 18.30 grams | 1.242 grams |
| 2 | 4 | 21.94 grams | 20.21 grams | 1.191 grams |
| 3 | 1 | 18.39 grams | 16.26 grams | 1.041 grams |
| 3 | 2 | 20.64 grams | 18.76 grams | 1.093 grams |
| 3 | 3 | 20.18 grams | 18.32 grams | 1.066 grams |
| 4 | 1 | 21.14 grams | 18.36 grams | 1.029 grams |
| 4 | 2 | 20.46 grams | 18.09 grams | 1.200 grams |
| 4 | 3 | 22.23 grams | 19.44 grams | 1.033 grams |
| 5 | 1 | 21.04 grams | 19.12 grams | 1.073 grams |
| 5 | 2 | 20.52 grams | 18.02 grams | 1.093 grams |
| 5 | 3 | 17.73 grams | 16.03 grams | 1.042 grams |
| 6 | 1 | 20.48 grams | 20.60 grams | 1.081 grams |
| 6 | 2 | 21.10 grams | 20.93 grams | 1.021 grams |
| 6 | 3 | 21.98 grams | 21.42 grams | 1.001 grams |
| 7 | 1 | 20.75 grams | 19.87 grams | 1.052 grams |
| 7 | 2 | 20.22 grams | 19.77 grams | 1.095 grams |
| 7 | 3 | 20.95 grams | 20.55 grams | 1.042 grams |

Brief Observation: Acute inflammatory responses to implanted biomaterials may cause the weight loss. However, it is difficult to simply determine the degree of inflammatory responses by the data of weight loss. Consequently, immunolgoical cell numbers were estimated.

B. The Recruitment of Neutrophil (PMN)

| Test Material | Myeloperoxidase activities (mUnit) | Estimated Cell Number (× 10,000) |
|---|---|---|
| #1 | 47.6 ± 14.0 | 207.4 ± 61.0 |
| #2 | 12.8 ± 6.5 | 55.8 ± 28.3 |
| #3 | 23.6 ± 8.2 | 102.8 ± 35.7 |
| #4 | 18.0 ± 12.8 | 78.4 ± 55.8 |
| #5 | 15.2 ± 12.4 | 66.2 ± 54.0 |
| #6 | 0.0 ± 0.0 | 0.0 ± 0.0 |
| #7 | 33.1 ± 14.2 | 144.2 ± 61.9 |

Brief Interpretation:
Implanted foreign materials often found to trigger the acute inflammatory responses, which mediate the accumulation of inflammatory cells (neutrophils and macrophages) in implant sites. Naive or saline injected peritoneal cavity, the implantation site for this study, only a few neutrophils accumulated. After introduced with poor compatible materials (such as zymosan A-material #7), mice developed acute inflammatory responses with the accumulation of a large number of neturophils. Therefore, the number of recruited neutrophils may be obtained and used as an indicator of the tissue compatibility to implanted materials. Because neutrophils can cause damage to the surrounding tissues and the implanted materials a good material implant shall prompt minimal influx of neutrophils. Material #1 caused prompt significant neutrophil accumulation. Moderate neutrophils accumulation was found for material #3 and only mild neutrophils accumulation was found using material #2, #4 and #5. Material #2, #3, #4 and #5 are considered to be acceptable as implant materials.

C. The Recruitment of Monocytes/macrophages

| Test Material | Enzyme Activities (mUnit) | Estimated Cell Number (×100,000) |
|---|---|---|
| 1. | 354 ± 48 | 322 ± 44 |
| 2. | 284 ± 75 | 258 ± 68 |
| 3. | 236 ± 9 | 215 ± 8 |
| 4. | 321 ± 25 | 292 ± 23 |
| 5. | 887 ± 466 | 807 ± 424 |
| 6. | 31 ± 6 | 28 ± 5 |
| 7. | 48 ± 13 | 44 ± 12 |

Brief Interpretation
About 2,000,000 resident macrophages usually reside in the naive mouse peritoneum. During inflammatory responses, peripheral monocytes may be recruited to the peritoneum to join the resident macrophages. Macrophages are important in mediating wound healing responses, for example phagocytosing tissue debris and mediating the proliferation of fibroblasts,. Therefore, the number of macrophages recruited can be used as an indication of wound healing responsiveness, i.e. an indicator of tissue reconstruction occurring in the implant sites. Naive or saline (material #6) injected peritoneal cavity had 'normal' macrophages (mostly resident macrophages) accumulation. Strong inflammatory agents (such as zymosan A-material #7) trigger severe inflammatory responses and the accumulation of neutrophils, which delay the appearance of macrophages. Material #5 triggered the most macrophage accumulation. Mild macrophages accumulation is found on material #1, #2, #3 and #4. This study suggest that material #1, #2, #3, #4, and #5 do not impair normal wound healing responses.

D. Total Peritoneal Cells

| Test Material | Enzyme Activities (mUnit) |
|---|---|
| 1. | 1526 ± 135 |
| 2. | 397 ± 98 |
| 3. | 877 ± 131 |
| 4. | 924 ± 145 |
| 5. | 1097 ± 593 |
| 6. | 167 ± 155 |
| 7. | 525 ± 155 |

Brief Interpretation:
In the process of implant mediated tissue responses, the implant sites are occupied by inflammatory cells (such as macrophages/monocytes and neutrophils) and proliferating fibroblast. The total number of cells in the implant sites, (peritoneal cavity), may represent the degree of tissue responses to implanted test materials. The total number of cells can be assessed by the activities of lactate dehydrogenase, which is a common cytoplasmic enzyme. Material #1 triggered substantial cell accumulation. Other test materials #2, #3, #4 and #5 induce milder tissue responses.

Chronic Inflammatory and Fibrotic Responses to Implanted Polysaccharide Biomaterials in Rats Overall Purpose The objective of this study was to investigate whether test polysaccharide materials differ in their tendency to trigger chronic tissue responses (including fibrosis and inflammation) in rats.

Animals

Male Sprague Dowley rats in good health, weighing approximately 150 grams, were used.

Test Materials and Animal ID Number

1. Test material #1 (1-1, 1-2, 1-3) Hydroxypropylmethyl Cellulose Fiber (length 150–500 μm, width 10–20 μm)
2. Test material #2 (2-1, 2-2, 2-3) Inulin Beads (38–90 μm)
3. Test material #3 (3-1, 3-2, 3-3) Alginate (high mannuronic acid content) Beads 38–90 μm)
4. Test material #4 (4-1, 4-2, 4-3) Chondoritin Sulfate Beads (38–90 μm)
5. Test material #5 (5-1, 5-2, 5-3) Hyaluronic Acid Beads (38–90 μm)
6. Test material #6 (6-1, 6-2, 6-3) Alginate (high guluronic acid content) Beads (38–90 μm)
7. Saline #8 (control) (7-1, 7-2, 7-3)

Test Protocol

1. Male Sprague Dawley rats (3 animals per test material, total 24 rats) were purchased from Taconic Farms (Germantown, N.Y.) and acclimated for 7 days prior to initiation of this study.
2. Rats were anesthetized with ketamine-xylazine (ketamine 80 mg/kg body weight and xylazine 12 mg/kg body weight) according to standard procedures. The fur on the back was then removed with electric clippers.
3. 1 ml of test material was implanted by subscapular inoculation in each animal.
4. After 4 weeks the rats were sacrificed and the implanted materials with surrounding fibrous/collagenous tissues were carefully removed and fixed with buffered formalin.
5. The explanted and fixed tissues were then embedded in paraffin, sectioned and stained with haematoxylin and eosin.

Results:

A. Material Injected:

| Weight of Test Materials Implanted in Rats | | | | | |
|---|---|---|---|---|---|
| ID# | WT(grams) | ID# | WT(grams) | ID# | WT(grams) |
| 1-1 | 1.07 | 1-2 | 1.09 | 1-3 | 1.04 |
| 2-1 | 1.04 | 2-2 | 1.01 | 2-3 | 0.95 |
| 3-1 | 1.02 | 3-2 | 1.03 | 3-3 | 1.04 |
| 4-1 | 1.04 | 4-2 | 0.99 | 4-3 | 0.97 |
| 5-1 | 1.04 | 5-2 | 1.00 | 5-3 | 1.04 |
| 6-1 | 1.03 | 6-2 | 1.13 | 6-3 | 1.03 |
| 7-1 | 1.01 | 7-2 | 0.95 | 7-3 | 1.07 |

B. Post-Injection Animal Care

After the injection, the implanted animals were observed for visible tissue responses around the implantation site. These were recorded at 1, 24, 72, and 144 hours post injection. The injection sites were scored on a scale of 0 to 3 as follows:

0=No reaction

1=Slight redness and swelling only over implant

2=Mild redness and swelling over implant and surrounding tissues

3=Severe redness and swelling over implant and surrounding tissues

| Visible Tissue Responses To Implanted Test Materials | | | | | |
|---|---|---|---|---|---|
| Test materials | Animal # | \multicolumn{4}{c}{The score of tissue responses} | | | |
| | | 1 | 24 hours | 72 hours | 144 hours |
| 1 | 1 | 0 | 0 | 0 | 0 |
| 1 | 2 | 0 | 0 | 0 | 0 |
| 1 | 3 | 0 | 0 | 0 | 0 |
| 2 | 1 | 0 | 0 | 0 | 0 |
| 2 | 2 | 0 | 0 | 0 | 0 |
| 2 | 3 | 0 | 0 | 0 | 0 |
| 3 | 1 | 0 | 0 | 0 | 0 |
| 3 | 2 | 0 | 0 | 0 | 0 |
| 3 | 3 | 0 | 0 | 0 | 0 |
| 4 | 1 | 0 | 0 | 0 | 0 |
| 4 | 2 | 0 | 0 | 0 | 0 |
| 4 | 3 | 0 | 0 | 0 | 0 |
| 5 | 1 | 0 | 0 | 0 | 0 |
| 5 | 2 | 0 | 0 | 0 | 0 |
| 5 | 3 | 0 | 0 | 0 | 0 |
| 6 | 1 | 0 | 0 | 0 | 0 |
| 6 | 2 | 0 | 0 | 0 | 0 |
| 6 | 3 | 0 | 0 | 0 | 0 |
| 7 | 1 | 0 | 0 | 0 | 0 |
| 7 | 2 | 0 | 0 | 0 | 0 |
| 7 | 3 | 0 | 0 | 0 | 0 |

No evident tissue inflammatory responses were observed for all polysaccharide implants.

C. Animal Weights

The weights of animals before and after implantation were measured. All animals gained weight after implantation and test materials had no obvious influence on the rate of growth as compared with the control group (#7).

| Weights and Weight Change in Implanted Animals | | | | | | | |
|---|---|---|---|---|---|---|---|
| Rat ID# | Body weight (grams) | | | Rat ID# | Body weight (grams) | | |
| | Initial | Final | Gain | | Initial | Final | Gain |
| 1-1 | 138.6 | 365.3 | 226.7 | 2-1 | 172.4 | 368.3 | 195.9 |
| 1-2 | 142.1 | 326.1 | 184.0 | 2-2 | 132.6 | 324.2 | 191.6 |
| 1-3 | 160.9 | 365.1 | 204.2 | 2-3 | 138.9 | 341.8 | 202.9 |

-continued

Weights and Weight Change in Implanted Animals

| Rat ID# | Body weight (grams) Initial | Final | Gain | Rat ID# | Body weight (grams) Initial | Final | Gain |
|---|---|---|---|---|---|---|---|
| 3-1 | 150.4 | 337.2 | 186.8 | 4-1 | 152.3 | 333.5 | 181.2 |
| 3-2 | 146.7 | 306.5 | 159.8 | 4-2 | 172.3 | 379.3 | 207.0 |
| 3-3 | 160.8 | 384.1 | 223.3 | 4-3 | 136.1 | 309.9 | 173.8 |
| 5-1 | 170.6 | 379.2 | 208.6 | 6-1 | 157.8 | 354.3 | 196.5 |
| 5-2 | 145.6 | 330.7 | 185.1 | 6-2 | 166.4 | 375.3 | 208.9 |
| 5-3 | 160.6 | 341.1 | 180.5 | 6-3 | 138.8 | 345.2 | 206.4 |
| 7-1 | 163.8 | 364.6 | 200.8 | | | | |
| 7-2 | 147.8 | 357.4 | 209.6 | | | | |
| 7-3 | 146.3 | 344.4 | 198.1 | | | | |

D. Histopathology After 30 days of implantation, the material implants were recovered, fixed and embedded as described above. The samples were sectioned and stained with haematoxylin and eosin. The tissue responses to test materials were categorized into two patterns and subjectively graded according to increasing severity (0–3) by two investigators and by a board certified pathologist.

Pattern A: Higher fibrotic responses, typified by the presence of fibroblasts and fibrous material surrounding the implant mass. Strong inflammatory cell infiltration and giant cell reaction surrounding individual particles of test materials.

Pattern B: Weak cell filtration (centers of the implants have few or no cells) and relatively mild giant cell reactions and fibrosis around test materials.

Type and Severity of Tissue Reactions to Implants

| Test Material | Animal # | Pattern | Foreign | Fibrosis body giant | Chronic Inflammation cells |
|---|---|---|---|---|---|
| 1 | 1 | B | 3+ | 0 | 2+ |
| 1 | 2 | B | 3+ | 0 | 1–2+ |
| 1 | 3 | B | 3+ | 0–1+ | 1+ |
| 2 | 1 | A | 3+ | 2+ | 1+ |
| 2 | 2 | A | 3+ | 2+ | 1+ |
| 2 | 3 | A | 3+ | 0–1+ | 1–2+ |
| 3 | 1 | — | (no material observed) | | |
| 3 | 2 | B | 2+ | 1–2+ | 2+ |
| 3 | 3 | B | 2+ | 2+ | 1–2+ |
| 4 | 1 | A | 3+ | 1–2+ | 1+ |
| 4 | 2 | A | 3+ | 1+ | 1+ |
| 4 | 3 | A | 3+ | 1+ | 1+ |
| 5 | 1 | A | 3+ | 1+ | 0–1+ |
| 5 | 2 | A | 3+ | 1+ | 1+ |
| 5 | 3 | A | 3+ | 1+ | 2+ |
| 6 | 1 | A | 3+ | 1+ | 1+ |
| 6 | 2 | A | 3+ | 2+ | 1+ |
| 6 | 3 | A | 3+ | 2+ | 0–1+ |
| 7 | 1 | B | 0 | 0 | 0 |
| 7 | 2 | B | 0 | 0 | 0 |
| 7 | 3 | B | 0 | 0 | 0 |

There was no appearance of any adverse reaction in animals during a 30-day implantation with any of 6 polysaccharide materials. All 6 materials are considered safe for tissue implantation. All implants (except animal 1 with material #3) were remained in the place when retrieving.

Test Material #1

Foreign body reaction and chronic inflammatory response were evident around the material implants. No obvious fibrotic tissue (fibroblasts and collagen fibril) was found in the capsules around the implant. Most of the inflammatory cells accumulated around the implants, and few cells were found inside the implants.

Test Material #2

These implants triggered strong foreign body reactions and fibrotic responses. The implants were also surrounded by fibrous/collagenous capsules (100 to 300 $\mu$m thick) comprised of collagen fibrils and numbers of foreign body giant cells and fibroblasts. The interstices of the implants also were filled with large numbers of cells. The invading cells (including numerous giant cells and some fibroblasts) were found encircling individual particles of test material.

Test Material #3

This material initiated mild foreign body and fibrotic responses. A large number of fibroblasts, collagen fibrils and some giant cells formed fibrotic capsules around the implants (50–300 $\mu$m thickness). Cell penetration to the inner aspects of the implant was relatively rare.

Test Material #4

These implants triggered strong foreign body reactions but weak fibrotic responses. Implants were surrounded with a thin layer (50 to 150 $\mu$m thickness) of fibrous/collagenous capsules, comprised mainly of fibroblasts and collagen fibrils. Large numbers of foreign body giant cells occurred around and within the implant bodies.

Test Material #5

Inplanted materials prompted strong foreign body reactions and weak fibrotic responses. The implants were covered by a thin fibrous/collagenous capsule (25 to 100 $\mu$m thick), comprised predominantly of fibroblasts and collagen fibrils. A large number of giant cells had invaded the implant body and enveloped the particles of test materials.

Test Material #6

Strong foreign body reaction and mild fibrotic responses were mediated by the material implants. Implants were surrounded by a large number of giant cells and some fibroblasts (50 to 150 $\mu$m thick). Cell penetration into this material was marked. A large number of giant cells had invaded deeply into the center of the material mass and formed many small reticular compartments within the implant.

Saline Control

No visible foreign body reaction or fibrotic response was found in the tissue as expected. Saline usually disappeared approximately an hour after injection.

Conclusions:

Expectably, our negative control (test material #7—saline injection) did not cause any visible adverse tissue responses. After implantation for 30 days, the test materials triggered widely different tissue responses. Qualitatively, the test materials can be divided into two distinct groups: 'bioactive' and 'bioinert'. The more bioactive materials (test material #2, 4, 5, and 6) triggered stronger tissue responses (including chronic inflammation, fibrosis, and foreign body giant cell responses) whereas the bioinert materials (test material #1 and 3) triggered only mild or weak tissue responses.

EXAMPLE 40

The studies showed that crosslinked polysaccharides (one hyaluronate and two different alginates) are non-immunogenic, which is essential for an implant material.

Immunogenic Responses to a Mixture of Polysaccharide Biomaterials in Rabbits

Study Objective

The objective of this study was to assess the production of antibody to implanted polysaccharide biomaterials in rabbits.

Animals:

Young male adult rabbits (New Zealand White) in good health, weighing approximately 2 Kg, were obtained from Millbrook Farm (Amherst, Mass.). Each animal was tattooed with a unique identification number.

Test Material and Animal ID Number
1. Hyaluronic Acid Beads (45–90 μm) (animal #1, 2, and 3)
2. Alginate Beads (high mannuronic acid content; 45–90 μm) (animal #4, 5 and 6).
3. Alginate Beads (high guluronic acid content; 45–90 μm) (animal #7, 8,and 9).

Test Protocol:
1. Male New Zealand White rabbits (3 animals per test group, total 9 rabbits) were purchased from Millbrook Farms (Amherst, Mass.) and acclimated for 7 days prior to initiation of this study.
2. After light anesthesia, each of the nine rabbits was immunized with test materials/Freund complete mixture on day zero (week 0) and then booster shots with test material/Freund incomplete mixture on day 28, 35, 42, 49, and 56 (or week, 4, 5, 6, 7, and 8).
    2a. Approximately 2.0 ml of the test material mixture/Freund complete (v:v=1:1) were used for initial injection.
    2b. Approximately 2.0 ml of the test material mixture/Freund incomplete (v:v=1:1) were used for booster shots.
3. The rabbits were monitored for six days after immunization. Thereafter, weekly inspection of the animals' health, diet and fluid intake were carried out.
4. The blood samples (10 ml) were collected in serum tubes from each animal on week 0 and 10.
5. After clotting at room temperature for two hours, blood samples were centrifuged (500 xg, 10 minutes) to collect serum. Rats were sacrificed by inhalation of $CO_2$. The implanted materials and tissues surrounding them were recovered by careful dissection and fixed with Formalin.
6. The fixed material was embedded en bloc in paraffin, sectioned and stained with haematoxylin and eosin.

Results:
A. Material Injected

Approximately 0.5 ml of the test materials was subscapularly administered to both left side and right side of the animal. The weights of injected materials were measured and are listed below.

| Weight of Test Materials Implanted In Rats | | |
|---|---|---|
| ID# | Left-WT(grams) | Right-WT(grams) |
| A-1 | 0.62 | 0.59 |
| B-1 | 0.61 | 0.53 |
| B-2 | 0.65 | 0.59 |
| C-1 | 0.58 | 0.54 |
| C-2 | 0.48 | 0.53 |
| D-1 | 0.46 | 0.55 |
| D-2 | 0.53 | 0.59 |
| E-1 | 0.61 | 0.53 |
| E-2 | 0.49 | 0.52 |

B. Post Injection Animal Care

After implantation, the animals were observed for visible tissue responses around the implantation site. These were recorded at 1, 24, 72, and 144 hours post injection. The injection sites were scored on a scale of 0 to 3 as follows:
0=No reaction
1=Slight redness and swelling only over implant
2=Mild redness and swelling over implant and surrounding tissues
3=Severe redness and swelling over implant and surrounding tissues

| Visible Tissue Responses to Implanted Test Materials | | | | | |
|---|---|---|---|---|---|
| Test materials | Animal # | \multicolumn{4}{c}{The score of tissue responses} |
| | | 1 hour | 24 hours | 72 hours | 144 hours |
| A | 1 | 0 | 0 | 0 | 0 |
| B | 1 | 0 | 0 | 0 | 0 |
| B | 2 | 0 | 0 | 0 | 0 |
| C | 1 | 0 | 0 | 0 | 0 |
| C | 2 | 0 | 0 | 0 | 0 |
| D | 1 | 0 | 0 | 0 | 0 |
| D | 2 | 0 | 0 | 0 | 0 |
| E | 1 | 0 | 0 | 0 | 0 |
| E | 2 | 0 | 0 | 0 | 0 |

No externally visible inflammatory response or other adverse tissue reactions

C. Animal weights:

The weights of animals before and 30 days after implantation were measured. The test materials had no obvious effect on the growth of the test animals.

D. Antibody Titers:

| Test Materials | Antibody titration | Means | Gel Surf. Area | Stand. Surf. Area |
|---|---|---|---|---|
| 1 | 148,78,100 | 109 ± 36 | 16.17 cm$^2$ | 0.28 cm$^2$ |
| 2 | 86,32,42 | 53 ± 29 | 12.86 cm$^2$ | 0.28 cm$^2$ |
| 3 | 48,50,108 | 69 ± 34 | 14.56 cm$^2$ | 0.28 cm$^2$ |

Conclusion:

Very low antibody titers were seen in animals injected with any of the 3 testing materials. After normalization with surface area, the titer values are completely negligible. Therefore, we conclude that all three testing polysaccharide materials are non-immunogenic.

Appendix A

Enzyme Linked Immunosorbent Assay For Test Material #1, #2, and #3

Solution required:
Test serum (diluted 1:10 with PBS)
Pre-immune serum (diluted 1:10 with PBS)
Antigens (test materials #1, #2 and #3)
PBS
Washing buffer: PBS/0.05% Tween 20
Blocking solution: PBS/1.0% BSA
Antibody: Protein A conjugated with horseradish peroxidase (HRP) (Accurate Chem & Sci #BYA 8605-1) in PBS (10 mM pH 7.4)
Citrate buffer: Distilled water 100 ml
1.42 g NaH2PO4 (or 1.63 g of monohydrate)
1.05 g citric acid (1.15 g of monohydrate)
Substrate for horseradish peroxidase (HRP)*
15 mg o-phenylenediamine (abbreviated as OPD, sigma #P1526)
25 ml citrate buffer
25 ul 30% H2O2

*This substrate must be made up fresh each time prior to the assay.

Equipment required:
  Octavac filter strip system (Fisher)
  96-well strip plates (Fisher #07-200-359)
  filter strip spacer (Fisher #07-200-363)
  Centrifuge
  Standard 96-well plate centrifuge adapter
Method:
  1. 10 ul of test materials and 90 ul of PBS will be added in 96-well strip plate. This provides about 5 ug of antigen per well. (100 ul PBS will be added to control wells).
  2. Remove solution by centrifugation (500×g, 10 minutes). 100 ul of PBS will be added to each well. After 10 minute incubation in room temperature, solution will then be removed by centrifugation. Followed with 2 more washes with PBS.
  3 Add 200 ul of blocking solution to each well (including control wells). Incubate at 37° C. for one hour.
  4. Wash each well 1× with PBS/Tween 20 as described in step 2, then 2× with PBS.
  5. Add series diluted serum (100 ul/well) to each wells using PBS as diluent. Incubate for one hour at 37° C.
  6. Wash each well 1× with PBS/Tween 20, then 2× with PBS.
  7. Add 100 ul of HRP conjugated protein A at 37° C. for 1 hours.
  8. Wash each well 1× with PBS/Tween 20, then 2× with PBS.
  9. Add 200 ul of substrate (OPD, sigma #P1526) to each well at 37° C. for 30 minutes.
  10. Read results (absorbance at 450 nm), compare color with preimmune serum.

| Well Number | Treatment Antibody | Antigen |
| --- | --- | --- |
| 1,2 | BSA | No (PBS) |
| 3,4 | BSA | Rabbit anti-BSA (1:10) |
| 5,6 | Yes | Control serum (1:10) |
| 7,8 | Yes | Test serum (1:10) |
| 9,10 | Yes | Test serum (1:20) |
| 11,12 | Yes | Test serum (1:40) |

EXAMPLE 41

We performed sterility test on hyaluronate microspheres and the results demonstrate that this polysaccharide does not support growth of any bacteria or fungi on its surface or in the material matrix. Moreover, pre-sterilized (i.e., non-autoclaving) gels were also negative for bacteria growth. We conclude that using polysaccharides such as hyaluronate for implants should limit the occurrence of biomaterial associated infections, a common complication that often results in implant/device failure.

We also tested in-vitro cytotoxicity and hemolysis on hyaluronate gels. The results showed the materials are not toxic to the cells, which can be expected since most polysaccharides are extracted from living organisms.

Purpose: The purpose of this experiment is to test the sterility of hyaluronate beads both before and after autoclaving.
Procedure:
  1. Submitted one syringe of Pre-Autoclaved hyaluronate beads and one syringe of Post-Autoclaved hyaluronate beads to the microbiology lab for sterility testing.
Note: Each syringe contains 3 cc of cross-linked hyaluronate beads.
Results: Both samples were negative for growth.

Direct Transfer Procedure:
  1. Under a laminar flow hood, expel half the contents of the test syringe into a 25×200 mm test tube containing a minimum remaining half into a test tube containing a minimum of 40 ml of sterile Trypticase Soy Broth (TSB).
  2. Incubate product samples in FTM at 30–35° C. for 14 days, and those in TSB at 20–25° C. for 14 days.
  3. After 14 days, check for any signs of turbidity which would indicate bacterial or fungal growth.
Results:
  No turbidity was found in the "Before" or "After" samples. This means that no bacteria or fungi were found in the samples. Therefore, the Hyaluronate Before and the Hyaluronate After can be considered sterile.
Cytotoxicity and Hemolysis Testing
Purpose: The purpose of this experiment is to test hyaluronate gel for cytotoxicity and heolysis.
Procedure:
  1. Prepared syringes, each containing 4 ml of 45–90 micron hyaluronate gel.
  2. Submitted the syringes to the Microbiolotu Lab for Cytotoxicity and hemolysis testing.
Cytotoxicity (Agar Diffusion Method)
  1. Absorbant discs were saturated with the test sample and allowed to drain for approximately five minutes. The discs were transferred to the surface of the agar overlaying the test cell monolayers. The test sample showed no cytotoxic reactivity and met the requirements of the agar diffusion cytotoxicity test.
Hemolysis
  2. The test procedure was modified slightly due to the viscous nature of the test sample 10 ml of the suspension was transferred to a sterile test tube. 25 ml of sterile saline solution was added to this tube to bring the total volume to 35 ml which was then extracted at 70° C. for 24 hours per ML-009. Testing from this point won was per ML-009. The sample had a mean hemolysis value of 1.99%, which meets the requirements of the test.

EXAMPLE 42

To qualify as an implant, the implant material must contain very low endotoxin level (<20 EU for one implant device or <5 EU/Kg bodyweight per hour for injection drug, as required by FDA). The raw materials or components of an implant must therefore have a very low level of endotoxin, to avoid expensive depyrogenation steps We have done endotoxin screening tests on many different polysaccharides raw materials as well as on all crosslinked implantable gels including (1) hydroxypropyl methyl cellulose, (2) inulin, (3) alginates with different formulations, (4) chondroitin sulfate, (5) sodium hyaluronates from different suppliers (7) sephadex with various sizes and different rigidities. The results show either no or very low endotoxin level, which suggests that the polysaccharides are good candidates for implant materials.

EXAMPLE 43

We performed in vitro cell culture studies to test whether crosslinked hyaluronate microspheres from two different sources support growth of human fibroblasts. The fibroblast plays an essential role in wound healing and tissue remodeling processes. Briefly, it produces enzymes to digest dead tissue, generate new collagen and other extracellulaar matrix proteins to reconstruct new tissue, and coordinates many events during inflammation and angiogenesis to ensure smooth remodeling. Implant materials which are compatible with fibroblasts should assist healing. Our studies showed hyaluronate support a normal growth of fibroblasts.

Purpose: The purpose of this experiment is to see if fibroblasts will attach to the Hyaluronate Beads on both Tissue Culture and Non-Tissue Culture Treated Well Plates.

Procedure:
1. Coated two wells of Hyaluronate Beads from source #1 on both Tissue Culture and Non-Tissue Culture Treated Well Plates.
2. Coated two wells of Hyaulronate Beads from source #2 on both Tissue Culture and Non-Tissue Culture Treated Well Plates.
3. Allowed to dry overnight.
4. Placed 100,000 cells in MEM Incomplete Media+L-glutamine in each well.
5. Allowed to dry overnight.

Results:
Well Plates were examined under the microscope.
Tissue Culture Treated Well Plate:
For hyaluronate beads from both sources, the cells attached to the entire surface of the beads and the well.
Non-Tissue Culture Treated Well Plate:
For hyaluronate beads from both sources, the cells were attached to the beads only.
Summary: The cells attached to the beads on both the Tissue Culture Treated and Non-Tissue Culture Treated Well Plates.

EXAMPLE 44

We performed extrusion tests on many different crosslinked polysaccharide gels either manually (hand extrusion) or by an Instron machine. By controlling softness and size range of the particles, all polysaccharides can be extruded easily through small gauge needles (e.g., 22 gauge). The elastoviscous property of most polysaccharide materials warrants them as an excellent candidate for injectable implants.

We also injected different polysaccharide gels into pig bladders and pig urethras. By comparing the results with collagen injection, we found many polysaccharides provided equal or even better integrity as well as stability (i.e., overall bulking effects) within mucous tissue. We conclude that using crosslinked polysaccharides for soft tissue augmentation is surprisingly effective.

Procedure:
1. Placed 0.4 g of beads in a 10 cc syringe.
2. Added 10 ml of PBS to each syringe and mixed thoroughly.
3. Turned each syringe plunger side down and allowed to sit.
   1. Sephadex G-50-50
   2. Sephadex G-75-50
   3. Sephadex G-200-50
   4. Sephadex G-200-120
   5. Alginate
   6. Chondoritin Sulfate A
   7. Hyaluronate Observations:
Two of the four syringes that were made had separated into a liquid layer and a bead layer.
   Sephadex G-50-50 5 cc beads 5 cc liquid
   Sephadex G-75-50 6 cc beads 4 cc liquid
   Sephadex G-200-50 10 cc beads
   Sephadex G-200-120 10 cc beads Procedure:
4. Extruded the liquid layer from the syringes that had separated.
5. Attached 22 gauge needle.
6. Injected the sample into a pig bladder and a pig urethra.

Results:
Collagen—Easily extruded through the needle and into the tissues. Soft and mushy once inside the tissues. Did not maintain shape. Spread out over time. Looks like fat.
G200-120—Easily extruded through the needle and into the tissues. Soft once inside the tissues. Maintained shape. Similar to Collagen.
G-50-50—Easily extruded through the needle and into the tissues. Very hard once inside the tissues. Maintained shape very well. Like a hard tumor.
Alginate—Fairly difficult to extrude into the tissues. Hard once inside the tissues. Maintained shape well. Very much like the Sephadex 50-50, but not quite as hard.
G-200-50—Easily extruded through the needle and into the tissues. Soft inside the tissues. Maintained shape with slight spread overtime. Similar to Collagen, but maintained shape better.
Hyaluronate—Easily extruded through the needle and into the tissues. Soft once inside the tissues. Maintained shaped with slight spread overtime. Similar to Collagen, but maintained shape better.
G-75-50—Easily extruded through the needle and into the tissues. Hard once inside the tissues. Maintained shape well. Similar to Sephadex G-50-50, but not quite as hard.
Chondroitin Sulfate A—Easily extruded through the needle and into the tissues. Soft once inside the tissues. Maintained shape with a slight spread over time. Similar to Collagen, but firmer and held shape better.

Summary of Bladder Injection Data

| Sample | Extrudability thru 22 Gauge | Firmness | Stability |
| --- | --- | --- | --- |
| Collagen | Easily | Very Soft | Spread out overtime |
| Sephadex G-50-50 | Easily | Very Hard | Maintained shape |
| Sephadex G-75-50 | Easily | Hard | Maintained shape |
| Sephadex G-200-50 | Easily | Soft | Slight spread overtime |
| Sephadex G-200-120 | Easily | Soft | Maintained shape |
| Alginate | Difficult | Hard | Maintained shape |
| Hyaluronate | Easily | Soft | Slight spread overtime |
| Chondroitin Sulfate A | Easily | Soft | Slight spread overtime |

Samples Ranked from Hardest to Softest
1. Sephadex G-50-50
2. Alginate
3. Sephadex G-75-50
4. Hyaluronate
5. Chondroitin Sulfate A
6. Collagen*
6. Sephadex G-200-120*
6. Sephadex G-200-50*
*All very similar Procedure:
7. Cut each injection site open to see the texture of the beads once inside the tissues.

Observations: When the injection site was cut open with a scalpel, each sample came out in a paste-like gel.

Purpose: To inject beads into a pig bladder and a pig urethra while observing the ease of extrudability and whether or not the beads remain in place once inside the bladder and urethra tissues.

Procedure:
1. Placed 0.4 g of beads in a 10 cc syringe.
2. Added 10 ml of PBS to each syringe and mixed thoroughly.
3. Turned each syringe plunger side down and allowed to sit overnight.
   The four syringes made are as follows:
   1. Sephadex G-50-50
   2. Sephadex G-200-50
   3. Sephadex G-200-120
   4. Sepharose CL-2B-300
4. Extruded the liquid layer from each of the four syringes.
5. Attached 22 gauge needle.
6. Injected into pig bladder and urethra.
7. Additionally collagen was injected into the pig bladder and urethra also.

Results:

Collagen—Easily extruded through the needle and into the tissues. Remained in place once inside the tissues. Formed a soft and mushy bump where injected. It was also very soft and pliable.

The first injection into the bladder resulted in a bleb (blister like pustule). This was because the injection was made too close to the surface. The second injection into the bladder was deep enough into the tissues so as not to cause a bleb, but a visible lump never appeared in the tissue. When injected into the urethra another bleb formed. Also the collagen would start shooting out of hole in which the needle was inserted. ps G-50-50 Easily extruded into the bladder and urethra. Stayed in place once injected into the tissues. Formed an extremely hard bump where injected. The bump could not be moved around or squeezed.

Sephadex G-200-50

Easily extruded into the tissues. Remained in place at first, but slowly began to dissipate. At first formed a firm bump, but did not hold shape with time. Even though it was firm it was not nearly as firm as the Sephadex G-50-50 and with time it became as soft and pliable as the collagen.

Sephadex G-200-120

Easily extruded into the tissues.

Remained in place after injection.

Formed a hard ball inside the tissue. This ball was harder than the G-200-50, but not as hard as the G-50-50.

First injection into the urethra was deep enough to form a visible knot without bleeding. The knot retained its shape well.

Chondroitin Sulfate A

Easily extruded into the tissues.

Remained in place once inside the tissues.

Formed a firm knot at first, but lost its firmness overtime.

| Sample | INJECTIONS Extrudability thru 22 Gauge | Stability | Firmness |
|---|---|---|---|
| Collagen | Easily | Remained in place | Soft and pliable |
| Sephadex G-50-50 | Easily | Remained in place | Very hard knot |
| Sephadex G-200-50 | Easily | Dissipated with time | Firm at first, but soft overtime |
| Sephadex G-200-120 | Easily | Remained in place | Hard knot formed |
| Hyaluronte (Lifecore) | Unable in tissues | n/a | n/a |
| Chondroitin Sulfate A | Easily | Remained in place | Firm knot formed |
| Alginate (Sigma) | Easily | Remained in place | Firm at first, but soft overtime |

Purpose: To swell Sephadex beads and then test their extrudability through a 22G1 needle on the Instron machine.

Procedure:
1. Placed 0.5 g of beads in small beaker.
2. Added 30 ml of PBS to the beads.
3. Allowed beads to swell overnight.
   The following beads were used:
   Sephadex G-50-50
   Sephadex G-75-50
   Sephadex G-200-50
   Sephadex G-200-120
4. Packed the beads in 3 cc syringes. Three syringes were made for each type of beads.
5. Tested each syringe on the Instron machine using a 22G1 needle. The average load at maximum load and the average load between limits were was 14.41 lbs. and 0.6584 lbs. for the G-50-50; 5.632 and 0.5047 for G-75-50; 0.9315 and 0.3349 for G-200-50; and 0.9450 and 0.4018 for G-200-120. The purpose of this experiment was to test the amount of force needed to extrude Pre-Autoclaved Hyaluronate Beads and Post-Autoclaved Hyaluronate Beads through a syringe.

Procedure:
Tested each syringe on the Instron using a 22G1 needle.

Results:

Pre-Autoclaved Hyaluronate Beads

Maximum Load: 4.333 lbs.

Average Load Between Limits 1: 0.3037 lbs.

(This is the average load from start to finish).

Post-Autoclaved Hyaluronate Beads

Maximum Load: 4.327 lbs.

Average Load Between Limits 1: 0.3010 lbs.

(This is the average load from start to finish).

Summary:

Autoclaving has no effect on the extrudability of the Hyaluronate Beads.

Although the present invention has been described in detail with respect to various embodiments thereof, it should be clearly understood that the same is by way of example and illustration only and is not to be taken by way of limitation, the spirit and scope of the present invention being limited only by the terms of the appended claims.

What is claimed is:

1. A method of soft tissue augmentation comprising administering to a patient in need of soft tissue augmentation an aqueous dispersion of crosslinked water-swellable polymer particles in an amount to effectively augment the affected tissue of the patient, wherein the particles are substantially homogeneous in size, wherein the particles are between about 10 micrometers in diameter and about 250 micrometers in diameter, and wherein at least 80% of the particles are spherical.

2. The method of claim 1, wherein the particles contain at least one water-soluble polymer selected from the group consisting of proteins, polysaccharides, peptidoglycans, glycoproteins, proteoglycans, celluloses, teichoic acids, lipopolysaccharides, and synthetic hydrophilic polymers, sodium alginate, poly(N-vinyl pyrrolidone), methyl cellulose, chitin, chitosan, agarose, dextrans, poly(vinyl alcohol), chondroitin sulfate, xanthans, dermatan sulfate, keratin sulfate, amylose, amylopectin, carrageenans, glycogen, starch, heparin sulfate, limit dextians and fragments thereof, emulsan, gellan, curdlan, hyaluronic acid, poly(ethylene oxide), bovine serum albumin, human gamma globulin, and mixtures thereof.

3. The method of claim 1, wherein the particles comprise at least one water-soluble polymer which is a polysaccharide.

4. The method of claim 3, wherein the polysaccharide is selected from the group consisting of hyaluronic acid, sodium alginate, chondroitin sulfate, celluloses, chitin, chitosan, agarose, dextrans, xanthans, dermatan sulfate, amylose, emulsan, gellan, curdlan, amylose, carrageenans, amylopectin, glycogen, starch, heparin sulfate, and limit dextrins or fragments thereof.

5. The method of claim 1, wherein the aqueous dispersion of crosslinked water-swellable polymer particles is administered to a patient in an amount effective to treat a defect selected from the group consisting of urinary incontinence, vesicoureteral reflux, glottic insufficiency, gastroesophageal reflux, and skin defects.

6. The method of claim 1, wherein the particles further comprise a bioactive agent.

7. A method of promoting tissue growth comprising administering to a patient in need of tissue growth an aqueous dispersion of crosslinked water-swellable polymer particles in an amount which provides a scaffold sufficient to promote tissue growth in the patient, wherein the particles are substantially homogeneous in size, wherein the particles are between about 10 micrometers in diameter and about 250 micrometers in diameter, and wherein at least 80% of the particles are spherical.

8. The method of claim 7, wherein the particles contain at least one water-soluble polymer selected from the group consisting of proteins, polysaccharides, peptidoglycans, glycoproteins, proteoglycans, celluloses, teichoic acids, lipopolysaccharides, and synthetic hydrophilic polymers, sodium alginate, poly(N-vinyl pyrrolidone), methyl cellulose, chitin, chitosan, agarose, dextrans, poly(vinyl alcohol), chondroitin sulfate, xanthans, dermatan sulfate, keratin sulfate, amylose, amylopectin, carrageenans, glycogen, starch, heparin sulfate, limit dextrans and fragments thereof, emulsan, gellan, curdlan, hyaluronic acid, poly(ethylene oxide), bovine serum albumin, human gamma globulin, and mixtures thereof.

9. The method of claim 7, wherein the particles comprise at least one water-soluble polymer which is a polysaccharide.

10. The method of claim 9, wherein the polysaccharide is selected from the group consisting of hyaluronic acid, sodium alginate, chondroitin sulfate, celluloses, chitin, chitosan, agarose, dextrans, xanthans, dermatan sulfate, amylose, emulsan, gellan, curdlan, amylose, carrageenans, amylopectin, glycogen, starch, heparin sulfate, and limit dextrins or fragments thereof.

11. The method of claim 7, wherein the aqueous dispersion of crosslinked water-swellable polymer particles is administered to a patient in an amount effective to promote cell growth of tissue in the breast, lip, penis, bone, cartilage, or tendon.

12. The method of claim 7, wherein the aqueous dispersion of water-swellable polymer particles is administered to a patient in an amount effective to promote wound healing.

13. The method of claim 7, wherein the particles further comprise a bioactive agent.

14. The method of claim 1, wherein the particles contain at least one water-soluble polymer selected from the group consisting of polysaccharides, peptidoglycans, glycoproteins, proteoglycans, celluloses, teichoic acids, lipopolysaccharides, and synthetic hydrophilic polymers, sodium alginate, poly(N-vinyl pyrrolidone), methyl cellulose, chitin, chitosan, agarose, dextrans, poly(vinyl alcohol), chondroitin sulfate, xanthans, dermatan sulfate, amylose, amylopectin, carrageenans, glycogen, starch, heparin sulfate, limit dextrins and fragments thereof, emulsan, gellan, curdlan, hyaluronic acid, poly(ethylene oxide), and mixtures thereof.

15. The method of claim 7, wherein the particles contain at least one water-soluble polymer selected from the group consisting of polysaccharides, peptidoglycans, glycoproteins, proteoglycans, celluloses, teichoic acids, lipopolysaccharides, and synthetic hydrophilic polymers, sodium alginate, poly(N-vinyl pyrrolidone), methyl cellulose, chitin, chitosan, agarose, dextrans, poly(vinyl alcohol), chondroitin sulfate, xanthans, dermatan sulfate, amylose, amylopectin, carrageenans, glycogen, starch, heparin sulfate, limit dextrins and fragments thereof, emulsan, gellan, curdlan, hyaluronic acid, poly(ethylene oxide), and mixtures thereof.

* * * * *